US012642993B2

(12) United States Patent
Miller et al.

(10) Patent No.: US 12,642,993 B2
(45) Date of Patent: Jun. 2, 2026

(54) HIGH INTENSITY THERAPEUTIC ULTRASOUND (HITU) HISTOTRIPSY SYSTEMS, METHODS AND TREATMENT NAVIGATION SOFTWARE

(71) Applicant: HistoSonics, Inc., Plymouth, MN (US)

(72) Inventors: Ryan M. Miller, Saline, MI (US); Vladimir Perovic, Belgrade (RS); Viktor Bollen, Chelsea, MI (US); Jonathan M. Cannata, Ann Arbor, MI (US); Alexander P. Duryea, Ann Arbor, MI (US)

(73) Assignee: HistoSonics, Inc., Plymouth, MN (US)

( * ) Notice: Subject to any disclaimer, the term of this patent is extended or adjusted under 35 U.S.C. 154(b) by 0 days.

(21) Appl. No.: 18/924,812

(22) Filed: Oct. 23, 2024

(65) Prior Publication Data

US 2025/0128096 A1 Apr. 24, 2025

Related U.S. Application Data

(60) Provisional application No. 63/592,327, filed on Oct. 23, 2023.

(51) Int. Cl.
*A61N 7/00* (2006.01)
*G16H 20/40* (2018.01)

(52) U.S. Cl.
CPC ............... *A61N 7/00* (2013.01); *G16H 20/40* (2018.01); *A61N 2007/0004* (2013.01); *A61N 2007/0039* (2013.01)

(58) Field of Classification Search
CPC .............. A61N 7/00; A61N 2007/0004; A61N 2007/0039; A61N 7/02; G16H 20/40
See application file for complete search history.

(56) References Cited

U.S. PATENT DOCUMENTS

| | | | |
|---|---|---|---|
| 3,243,497 A | 3/1966 | Kendall et al. | |
| 3,679,021 A | 7/1972 | Goldberg et al. | |
| 3,693,415 A | 9/1972 | Whittington | |
| 3,879,699 A | 4/1975 | Pepper | |

(Continued)

FOREIGN PATENT DOCUMENTS

| | | |
|---|---|---|
| AU | 2017222925 B2 | 11/2021 |
| AU | 2023231624 | 9/2024 |

(Continued)

OTHER PUBLICATIONS

Cannata et al.; U.S. Appl. No. 18/311,050 entitled "Histotripsy systems and methods," filed May 2, 2023.

(Continued)

*Primary Examiner* — Serkan Akar
(74) *Attorney, Agent, or Firm* — Shay Glenn LLP

(57) ABSTRACT
A histotripsy therapy system configured for the treatment of tissue is provided, which may include any number of features. Provided herein are systems and methods that provide efficacious non-invasive and minimally invasive therapeutic, diagnostic and research procedures. Treatment planning systems are also provided for preparing and implementing a digital treatment plan. The treatment planning can include dividing a target tissue volume into a plurality of treatment locations, and controlling the speed, and pattern of movement between these tissue locations.

14 Claims, 14 Drawing Sheets

(56) References Cited

U.S. PATENT DOCUMENTS

| | | |
|---|---|---|
| 4,016,749 A | 4/1977 | Wachter |
| 4,024,501 A | 5/1977 | Herring et al. |
| 4,051,394 A | 9/1977 | Tieden |
| 4,114,457 A | 9/1978 | Thun |
| 4,117,446 A | 9/1978 | Alais |
| 4,266,747 A | 5/1981 | Souder, Jr. et al. |
| 4,269,174 A | 5/1981 | Adair |
| 4,277,367 A | 7/1981 | Madsen et al. |
| 4,351,038 A | 9/1982 | Alais |
| 4,406,153 A | 9/1983 | Ophir et al. |
| 4,440,025 A | 4/1984 | Hayakawa et al. |
| 4,447,031 A | 5/1984 | Souder, Jr. et al. |
| 4,453,408 A | 6/1984 | Clayman |
| 4,483,343 A | 11/1984 | Beyer et al. |
| 4,483,345 A | 11/1984 | Miwa |
| 4,548,374 A | 10/1985 | Thompson et al. |
| 4,549,533 A | 10/1985 | Cain et al. |
| 4,550,606 A | 11/1985 | Drost |
| 4,551,794 A | 11/1985 | Sandell |
| 4,575,330 A | 3/1986 | Hull |
| 4,622,972 A | 11/1986 | Giebeler, Jr. |
| 4,625,731 A | 12/1986 | Quedens et al. |
| 4,641,378 A | 2/1987 | McConnell et al. |
| 4,669,483 A | 6/1987 | Hepp et al. |
| 4,689,986 A | 9/1987 | Carson et al. |
| 4,757,820 A | 7/1988 | Itoh |
| 4,791,915 A | 12/1988 | Barsotti et al. |
| 4,819,621 A | 4/1989 | Ueberle et al. |
| 4,829,491 A | 5/1989 | Saugeon et al. |
| 4,856,107 A | 8/1989 | Dory |
| 4,865,042 A | 9/1989 | Umemura et al. |
| 4,888,746 A | 12/1989 | Wurster et al. |
| 4,890,267 A | 12/1989 | Rudolph |
| 4,922,917 A | 5/1990 | Dory |
| 4,928,672 A | 5/1990 | Grasser et al. |
| 4,938,217 A | 7/1990 | Lele |
| 4,957,099 A | 9/1990 | Hassler |
| 4,973,980 A | 11/1990 | Howkins et al. |
| 4,984,575 A | 1/1991 | Uchiyama et al. |
| 4,991,151 A | 2/1991 | Dory |
| 4,995,012 A | 2/1991 | Dory |
| RE33,590 E | 5/1991 | Dory |
| 5,014,686 A | 5/1991 | Schafer |
| 5,065,751 A | 11/1991 | Wolf |
| 5,078,140 A | 1/1992 | Kwoh |
| 5,080,101 A | 1/1992 | Dory |
| 5,080,102 A | 1/1992 | Dory |
| 5,091,893 A | 2/1992 | Smith et al. |
| 5,092,336 A | 3/1992 | Fink |
| 5,097,709 A | 3/1992 | Masuzawa et al. |
| 5,111,822 A | 5/1992 | Dory |
| 5,143,073 A | 9/1992 | Dory |
| 5,143,074 A | 9/1992 | Dory |
| 5,150,711 A | 9/1992 | Dory |
| 5,158,070 A | 10/1992 | Dory |
| 5,158,071 A | 10/1992 | Umemura et al. |
| 5,163,421 A | 11/1992 | Bernstein et al. |
| 5,165,412 A | 11/1992 | Okazaki |
| 5,174,294 A | 12/1992 | Saito et al. |
| 5,195,509 A | 3/1993 | Rentschler et al. |
| 5,209,221 A | 5/1993 | Riedlinger |
| 5,215,680 A | 6/1993 | D'Arrigo |
| 5,219,401 A | 6/1993 | Cathignol et al. |
| 5,222,806 A | 6/1993 | Roberts |
| 5,230,340 A | 7/1993 | Rhyne |
| 5,295,484 A | 3/1994 | Marcus et al. |
| 5,316,000 A | 5/1994 | Chapelon et al. |
| 5,354,258 A | 10/1994 | Dory |
| 5,380,411 A | 1/1995 | Schlief |
| 5,393,296 A | 2/1995 | Rattner |
| 5,409,002 A | 4/1995 | Pell |
| 5,431,621 A | 7/1995 | Dory |
| 5,435,311 A | 7/1995 | Umemura et al. |
| 5,443,069 A | 8/1995 | Schaetzle |
| 5,450,305 A | 9/1995 | Boys et al. |
| 5,469,852 A | 11/1995 | Nakamura et al. |
| 5,474,071 A | 12/1995 | Chapelon et al. |
| 5,474,531 A | 12/1995 | Carter |
| 5,490,051 A | 2/1996 | Messana |
| 5,492,126 A | 2/1996 | Hennige et al. |
| 5,501,655 A | 3/1996 | Rolt et al. |
| 5,520,188 A | 5/1996 | Hennige et al. |
| 5,523,058 A | 6/1996 | Umemura et al. |
| 5,524,620 A | 6/1996 | Rosenschein |
| 5,524,875 A | 6/1996 | Thommen, Jr. |
| 5,540,909 A | 7/1996 | Schutt |
| 5,542,935 A | 8/1996 | Unger et al. |
| 5,558,092 A | 9/1996 | Unger et al. |
| 5,563,346 A | 10/1996 | Bartelt et al. |
| 5,566,675 A | 10/1996 | Li et al. |
| 5,573,497 A | 11/1996 | Chapelon |
| 5,580,575 A | 12/1996 | Unger et al. |
| 5,582,578 A | 12/1996 | Zhong et al. |
| 5,590,657 A | 1/1997 | Cain et al. |
| 5,601,526 A | 2/1997 | Chapelon et al. |
| 5,617,862 A | 4/1997 | Cole et al. |
| 5,648,098 A | 7/1997 | Porter |
| 5,665,054 A | 9/1997 | Dory |
| 5,666,954 A | 9/1997 | Chapelon et al. |
| 5,676,452 A | 10/1997 | Scholz |
| 5,676,692 A | 10/1997 | Sanghvi et al. |
| 5,678,554 A | 10/1997 | Hossack et al. |
| 5,683,064 A | 11/1997 | Copeland et al. |
| 5,694,936 A | 12/1997 | Fujimoto et al. |
| 5,695,460 A | 12/1997 | Siegel et al. |
| 5,717,657 A | 2/1998 | Ruffa |
| 5,720,287 A | 2/1998 | Chapelon et al. |
| 5,724,972 A | 3/1998 | Petrofsky |
| 5,743,863 A | 4/1998 | Chapelon |
| 5,753,929 A | 5/1998 | Bliss |
| 5,759,162 A | 6/1998 | Oppelt et al. |
| 5,766,138 A | 6/1998 | Rattner |
| 5,769,790 A | 6/1998 | Watkins et al. |
| 5,797,848 A | 8/1998 | Marian et al. |
| 5,800,365 A | 9/1998 | Zhong et al. |
| 5,820,623 A | 10/1998 | Ng |
| 5,823,962 A | 10/1998 | Schaetzle et al. |
| 5,827,204 A | 10/1998 | Grandia et al. |
| 5,836,896 A | 11/1998 | Rosenschein |
| 5,849,727 A | 12/1998 | Porter et al. |
| 5,873,902 A | 2/1999 | Sanghvi et al. |
| 5,879,314 A | 3/1999 | Peterson et al. |
| 5,928,169 A | 7/1999 | Schitzle et al. |
| 5,932,807 A | 8/1999 | Mallart |
| 5,947,904 A | 9/1999 | Hossack et al. |
| 6,001,069 A | 12/1999 | Tachibana et al. |
| 6,007,499 A | 12/1999 | Martin et al. |
| 6,022,309 A | 2/2000 | Celliers et al. |
| 6,036,667 A | 3/2000 | Manna et al. |
| 6,065,166 A | 5/2000 | Sharrock et al. |
| 6,088,613 A | 7/2000 | Unger |
| 6,093,883 A | 7/2000 | Sanghvi et al. |
| 6,113,558 A | 9/2000 | Rosenschein et al. |
| 6,126,607 A | 10/2000 | Whitmore, III et al. |
| 6,128,958 A | 10/2000 | Cain |
| 6,143,018 A | 11/2000 | Beuthan et al. |
| 6,165,144 A | 12/2000 | Talish et al. |
| 6,176,842 B1 | 1/2001 | Tachibana et al. |
| 6,296,619 B1 | 10/2001 | Brisken et al. |
| 6,308,585 B1 | 10/2001 | Nilsson et al. |
| 6,308,710 B1 | 10/2001 | Silva |
| 6,309,355 B1 | 10/2001 | Cain et al. |
| 6,318,146 B1 | 11/2001 | Madsen et al. |
| 6,321,109 B2 | 11/2001 | Ben-Haim et al. |
| 6,338,566 B1 | 1/2002 | Verdier |
| 6,344,489 B1 | 2/2002 | Spears |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,424,885 B1 | 7/2002 | Niemeyer et al. |
| 6,470,204 B1 | 10/2002 | Uzgiris et al. |
| 6,488,639 B1 | 12/2002 | Ribault et al. |
| 6,490,469 B2 | 12/2002 | Candy |
| 6,500,141 B1 | 12/2002 | Irion et al. |

(56) References Cited

U.S. PATENT DOCUMENTS

| | | | |
|---|---|---|---|
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,536,553 B1 | 3/2003 | Scanlon |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugharn, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,773,401 B1 | 8/2004 | Dreschel et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckal et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,175,599 B2 | 2/2007 | Hynynen et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,429,249 B1 | 9/2008 | Winder et al. |
| 7,431,704 B2 | 10/2008 | Babaev |
| 7,442,168 B2 | 10/2008 | Novak et al. |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 7,695,437 B2 | 4/2010 | Quistgaard et al. |
| 7,714,481 B2 | 5/2010 | Sakai |
| 7,771,359 B2 | 8/2010 | Adam |
| 7,967,763 B2 | 6/2011 | Deem et al. |
| 8,057,408 B2 | 11/2011 | Cain et al. |
| 8,295,912 B2 | 10/2012 | Gertner |
| 8,333,115 B1 | 12/2012 | Garvey et al. |
| 8,337,407 B2 | 12/2012 | Quistgaard et al. |
| 8,342,467 B2 | 1/2013 | Stachowski et al. |
| 8,376,970 B2 | 2/2013 | Babaev |
| 8,539,813 B2 | 9/2013 | Cain et al. |
| 8,568,339 B2 | 10/2013 | Rybyanets |
| 8,636,664 B2 | 1/2014 | Brannan |
| 8,715,187 B2 | 5/2014 | Landberg Davis et al. |
| 8,845,537 B2 | 9/2014 | Tanaka et al. |
| 8,932,239 B2 | 1/2015 | Sokka et al. |
| 9,028,434 B2 | 5/2015 | Tanaka |
| 9,049,783 B2 | 6/2015 | Teofilovic |
| 9,061,131 B2 | 6/2015 | Jahnke et al. |
| 9,144,694 B2 | 9/2015 | Cain |
| 9,220,476 B2 | 12/2015 | Coussios et al. |
| 9,228,730 B1 | 1/2016 | Inbody |
| 9,302,124 B2 | 4/2016 | Konofagou et al. |
| 9,457,201 B2 | 10/2016 | Hoelscher et al. |
| 9,526,923 B2 | 12/2016 | Jahnke et al. |
| 9,636,133 B2 | 5/2017 | Hall et al. |
| 9,642,634 B2 | 5/2017 | Cain et al. |
| 9,763,688 B2 | 9/2017 | Stulen et al. |
| 9,901,753 B2 | 2/2018 | Cain et al. |
| 9,943,708 B2 | 4/2018 | Roberts et al. |
| 10,022,107 B2 | 7/2018 | Thornton et al. |
| 10,046,179 B2 | 8/2018 | Oskar-Kohler |
| 10,046,181 B2 | 8/2018 | Barthe et al. |
| 10,058,352 B2 | 8/2018 | Carvell et al. |
| 10,071,266 B2 | 9/2018 | Cain |
| 10,130,828 B2 | 11/2018 | Vortman et al. |
| 10,219,815 B2 | 3/2019 | Maxwell et al. |
| 10,293,187 B2 | 5/2019 | Cannata et al. |
| 10,293,374 B2 | 5/2019 | Torashima et al. |
| 10,751,015 B2 | 8/2020 | Anderson et al. |
| 10,751,125 B2 | 8/2020 | Levy et al. |
| 10,765,892 B1 | 9/2020 | Vitek et al. |
| 10,772,646 B2 | 9/2020 | Lu et al. |
| 10,780,298 B2 | 9/2020 | Cain et al. |
| 10,791,991 B2 | 10/2020 | Burkett et al. |
| 10,799,209 B2 | 10/2020 | Lahti et al. |
| 10,806,421 B2 | 10/2020 | Keller |
| 10,820,813 B2 | 11/2020 | Alpert |
| 10,847,264 B2 | 11/2020 | Mansker et al. |
| 10,849,511 B2 | 12/2020 | Tochterman et al. |
| 10,869,603 B2 | 12/2020 | Millett et al. |
| 10,869,633 B2 | 12/2020 | Burkett |
| 10,869,648 B2 | 12/2020 | Hubbard et al. |
| 10,874,353 B2 | 12/2020 | Assif |
| 10,874,409 B2 | 12/2020 | Matsubara et al. |
| 10,878,586 B2 | 12/2020 | Brokman et al. |
| 10,888,232 B2 | 1/2021 | Anderson et al. |
| 10,893,808 B2 | 1/2021 | Dorando |
| 10,900,933 B2 | 1/2021 | Prus et al. |
| 10,905,394 B2 | 2/2021 | Stigall et al. |
| 10,912,463 B2 | 2/2021 | Davies et al. |
| 10,925,688 B2 | 2/2021 | Millett et al. |
| 10,927,003 B2 | 2/2021 | Millett et al. |
| 10,932,678 B2 | 3/2021 | Burkett |
| 10,939,826 B2 | 3/2021 | Glynn et al. |
| 10,942,022 B2 | 3/2021 | Johansson et al. |
| 10,973,419 B2 | 4/2021 | Cort |
| 10,993,618 B2 | 5/2021 | Mansker et al. |
| 10,993,628 B2 | 5/2021 | Tochterman |
| 10,993,694 B2 | 5/2021 | Meyer et al. |
| 11,000,185 B2 | 5/2021 | Stigall et al. |
| 11,006,840 B2 | 5/2021 | Stigall |
| 11,013,491 B2 | 5/2021 | Rice et al. |
| 11,020,087 B2 | 6/2021 | Hoffman |
| 11,020,089 B2 | 6/2021 | Corl |
| 11,026,591 B2 | 6/2021 | Burkett et al. |
| 11,040,140 B2 | 6/2021 | Unser et al. |
| 11,058,399 B2 | 7/2021 | Xu et al. |
| 11,071,522 B2 | 7/2021 | Hynynen et al. |
| 11,103,731 B2 | 8/2021 | Vortman et al. |
| 11,112,473 B2 | 9/2021 | Assif |
| 11,119,552 B2 | 9/2021 | Spencer et al. |
| 11,120,896 B2 | 9/2021 | Balignasay et al. |
| 11,123,019 B2 | 9/2021 | Merritt et al. |
| 11,123,575 B2 | 9/2021 | Vortman et al. |
| 11,135,454 B2 | 10/2021 | Xu et al. |
| 11,141,063 B2 | 10/2021 | Kemp et al. |

(56) References Cited

U.S. PATENT DOCUMENTS

| | | | |
|---|---|---|---|
| 11,141,131 B2 | 10/2021 | Stigall et al. |
| 11,160,513 B2 | 11/2021 | Anderson et al. |
| 11,205,507 B2 | 12/2021 | Anderson et al. |
| 11,219,748 B2 | 1/2022 | Burkett et al. |
| 11,224,349 B2 | 1/2022 | Davies et al. |
| 11,224,403 B2 | 1/2022 | Cori |
| 11,224,407 B2 | 1/2022 | Wrolstad et al. |
| 11,234,649 B2 | 2/2022 | Matsubara et al. |
| 11,246,533 B2 | 2/2022 | Henderson et al. |
| 11,246,565 B2 | 2/2022 | Corl |
| 11,253,225 B2 | 2/2022 | Hancock et al. |
| 11,260,160 B2 | 3/2022 | Matsubara et al. |
| 11,272,845 B2 | 3/2022 | Cheline et al. |
| 11,272,904 B2 | 3/2022 | Vortman et al. |
| 11,291,866 B2 | 4/2022 | Levy et al. |
| 11,298,030 B2 | 4/2022 | Davies et al. |
| 11,309,071 B2 | 4/2022 | Anderson |
| 11,311,271 B2 | 4/2022 | Stigall et al. |
| 11,324,410 B2 | 5/2022 | Burkett |
| 11,350,906 B2 | 6/2022 | Castella et al. |
| 11,350,954 B2 | 6/2022 | De Cicco et al. |
| 11,364,042 B2 | 6/2022 | Maxwell et al. |
| 11,369,346 B2 | 6/2022 | De Cicco et al. |
| 11,369,994 B2 | 6/2022 | Greenberg et al. |
| 11,395,638 B2 | 7/2022 | Shin et al. |
| 11,406,334 B2 | 8/2022 | Merritt |
| 11,406,355 B2 | 8/2022 | Hoffman et al. |
| 11,406,498 B2 | 8/2022 | Stigall et al. |
| 11,408,987 B2 | 8/2022 | Vignon et al. |
| 11,413,017 B2 | 8/2022 | Stigall et al. |
| 11,419,580 B2 | 8/2022 | Stigall et al. |
| 11,426,140 B2 | 8/2022 | Sudol et al. |
| 11,432,795 B2 | 9/2022 | Merritt |
| 11,432,900 B2 | 9/2022 | Rakic et al. |
| 11,446,000 B2 | 9/2022 | Minas et al. |
| 11,452,496 B2 | 9/2022 | Minas et al. |
| 11,452,506 B2 | 9/2022 | Perez et al. |
| 11,471,215 B2 | 10/2022 | Stigall et al. |
| 11,484,294 B2 | 11/2022 | Hancock et al. |
| 11,510,632 B2 | 11/2022 | Begin et al. |
| 11,517,291 B2 | 12/2022 | Kantor et al. |
| 11,520,874 B2 | 12/2022 | Kennedy et al. |
| 11,524,183 B1 | 12/2022 | Garcia Gutierrez et al. |
| 11,527,001 B2 | 12/2022 | Brokman et al. |
| 11,547,389 B2 | 1/2023 | Shin et al. |
| 11,553,889 B2 | 1/2023 | Spencer et al. |
| 11,554,386 B2 | 1/2023 | Pernot et al. |
| 11,559,207 B2 | 1/2023 | Stigall et al. |
| 11,567,153 B2 | 1/2023 | Stormont et al. |
| 11,576,649 B2 | 2/2023 | Cort |
| 11,576,652 B2 | 2/2023 | De Cicco et al. |
| 11,583,193 B2 | 2/2023 | Groenland et al. |
| 11,589,835 B2 | 2/2023 | Stigall et al. |
| 11,596,351 B2 | 3/2023 | Nair |
| 11,596,384 B2 | 3/2023 | Nair et al. |
| 11,596,385 B2 | 3/2023 | Stigall et al. |
| 11,596,387 B2 | 3/2023 | Song |
| 11,596,389 B2 | 3/2023 | Nair |
| 11,596,469 B2 | 3/2023 | Nair |
| 11,622,746 B2 | 4/2023 | Minas et al. |
| 11,638,576 B2 | 5/2023 | Groenland et al. |
| 11,647,989 B2 | 5/2023 | Hope Simpson et al. |
| 11,648,424 B2 | 5/2023 | Cannata et al. |
| 11,653,895 B2 | 5/2023 | Stigall et al. |
| 11,660,070 B2 | 5/2023 | Stigall et al. |
| 11,666,245 B2 | 6/2023 | Rajguru et al. |
| 11,666,307 B2 | 6/2023 | Unser |
| 11,672,433 B2 | 6/2023 | Park et al. |
| 11,672,552 B2 | 6/2023 | Pasquino et al. |
| 11,672,953 B2 | 6/2023 | May |
| 11,684,342 B2 | 6/2023 | Groenland et al. |
| 11,684,807 B2 | 6/2023 | Vortman et al. |
| 11,701,134 B2 | 7/2023 | Maxwell et al. |
| 11,707,207 B2 | 7/2023 | Stigall et al. |
| 11,707,254 B2 | 7/2023 | Tuillio et al. |
| 11,733,881 B2 | 8/2023 | Perez |
| 11,737,728 B2 | 8/2023 | Davies et al. |
| 11,744,527 B2 | 9/2023 | Scott et al. |
| 11,744,547 B2 | 9/2023 | Hynynen |
| 11,759,169 B2 | 9/2023 | Cori |
| 11,759,174 B2 | 9/2023 | Saroha et al. |
| 11,766,237 B2 | 9/2023 | Anderson |
| 11,771,370 B2 | 10/2023 | Hynynen |
| 11,771,405 B2 | 10/2023 | Rhodes |
| 11,771,869 B2 | 10/2023 | Cicco |
| 11,779,307 B2 | 10/2023 | Norris et al. |
| 11,806,167 B2 | 11/2023 | Burkett |
| 11,813,484 B2 | 11/2023 | Cannata et al. |
| 11,813,485 B2 | 11/2023 | Xu et al. |
| 11,819,712 B2 | 11/2023 | Cain et al. |
| 11,854,687 B2 | 12/2023 | Keller |
| 11,857,362 B2 | 1/2024 | Wrolstad et al. |
| 11,857,807 B2 | 1/2024 | Levy et al. |
| 11,864,918 B2 | 1/2024 | Burkett et al. |
| 11,872,412 B2 | 1/2024 | Vortman et al. |
| 11,879,973 B2 | 1/2024 | Prus et al. |
| 11,883,235 B2 | 1/2024 | Stigall et al. |
| 11,890,025 B2 | 2/2024 | Stigall et al. |
| 11,890,136 B2 | 2/2024 | Stigall et al. |
| 11,890,137 B2 | 2/2024 | Jenkins et al. |
| 11,950,954 B2 | 4/2024 | Hyun et al. |
| 11,963,822 B2 | 4/2024 | Wrolstad |
| 11,980,778 B2 | 5/2024 | Cannata et al. |
| 11,986,682 B2 | 5/2024 | Prus et al. |
| 11,992,366 B2 | 5/2024 | Stigall et al. |
| 12,035,919 B2 | 7/2024 | Unser |
| 12,036,066 B2 | 7/2024 | De Cicco et al. |
| 12,053,194 B2 | 8/2024 | Goertz et al. |
| 12,082,970 B2 | 9/2024 | Goodman |
| 12,096,949 B2 | 9/2024 | Fermi et al. |
| 12,097,072 B2 | 9/2024 | Stigall et al. |
| 12,112,850 B2 | 10/2024 | Kuo et al. |
| 12,115,007 B2 | 10/2024 | Merritt et al. |
| 12,144,677 B2 | 11/2024 | Corl |
| 12,150,661 B2 | 11/2024 | Maxwell et al. |
| 12,167,931 B2 | 12/2024 | Corl |
| 12,178,642 B2 | 12/2024 | Rajguru et al. |
| 12,178,643 B2 | 12/2024 | Stigall et al. |
| 12,186,130 B2 | 1/2025 | Davies |
| 12,220,259 B2 | 2/2025 | Burkett et al. |
| 12,232,907 B2 | 2/2025 | Chao et al. |
| 12,246,195 B2 | 3/2025 | Levy et al. |
| 12,257,461 B2 | 3/2025 | Son et al. |
| 12,263,035 B2 | 4/2025 | Stigall et al. |
| 12,295,600 B2 | 5/2025 | Stigall et al. |
| 12,303,327 B2 | 5/2025 | Stigall et al. |
| 12,343,198 B2 | 7/2025 | Laroya |
| 12,402,802 B2 | 9/2025 | Vitek et al. |
| 12,419,607 B2 | 9/2025 | Rajguru et al. |
| 12,440,188 B2 | 10/2025 | Chao et al. |
| 12,465,477 B2 | 11/2025 | Pasquino et al. |
| 12,490,936 B2 | 12/2025 | Corl |
| 2001/0039420 A1 | 11/2001 | Dory |
| 2001/0041163 A1 | 11/2001 | Sugita et al. |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2002/0145091 A1 | 10/2002 | Talish et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0169591 A1 | 9/2003 | Cochran |
| 2003/0181833 A1 | 9/2003 | Faragalla et al. |
| 2003/0199857 A1 | 10/2003 | Eizenhofer |
| 2003/0221561 A1 | 12/2003 | Milo |
| 2003/0236539 A1 | 12/2003 | Rabiner et al. |
| 2004/0127815 A1 | 7/2004 | Marchitto et al. |
| 2004/0138563 A1 | 7/2004 | Moehring et al. |
| 2004/0162571 A1 | 8/2004 | Rabiner et al. |
| 2004/0164213 A1 | 8/2004 | Stephan |
| 2004/0236248 A1 | 11/2004 | Svedman |
| 2004/0243021 A1 | 12/2004 | Murphy et al. |
| 2004/0249509 A1 | 12/2004 | Rogers et al. |

(56) References Cited

U.S. PATENT DOCUMENTS

| | | |
|---|---|---|
| 2004/0260214 A1 | 12/2004 | Echt et al. |
| 2005/0011296 A1 | 1/2005 | Koseki |
| 2005/0020945 A1 | 1/2005 | Tosaya et al. |
| 2005/0028289 A1 | 2/2005 | Hakamiun |
| 2005/0038339 A1 | 2/2005 | Chauhan et al. |
| 2005/0038361 A1 | 2/2005 | Zhong et al. |
| 2005/0121734 A1 | 6/2005 | Degertekin et al. |
| 2005/0152561 A1 | 7/2005 | Spencer |
| 2005/0154314 A1 | 7/2005 | Quistgaard |
| 2005/0154431 A1 | 7/2005 | Quistgaard et al. |
| 2005/0203399 A1 | 9/2005 | Vaezy et al. |
| 2005/0215901 A1 | 9/2005 | Anderson et al. |
| 2005/0234438 A1 | 10/2005 | Mast et al. |
| 2005/0283098 A1 | 12/2005 | Conston et al. |
| 2006/0058678 A1 | 3/2006 | Vitek et al. |
| 2006/0060991 A1 | 3/2006 | Holsteyns et al. |
| 2006/0074303 A1 | 4/2006 | Chornenky et al. |
| 2006/0089636 A1 | 4/2006 | Christopherson et al. |
| 2006/0173321 A1 | 8/2006 | Kubota et al. |
| 2006/0173387 A1 | 8/2006 | Hansmann et al. |
| 2006/0184166 A1 | 8/2006 | Valle et al. |
| 2006/0206028 A1 | 9/2006 | Lee et al. |
| 2006/0229659 A1 | 10/2006 | Gifford et al. |
| 2006/0241466 A1 | 10/2006 | Ottoboni et al. |
| 2006/0241523 A1 | 10/2006 | Sinelnikov et al. |
| 2006/0241533 A1 | 10/2006 | Geller |
| 2006/0264760 A1 | 11/2006 | Liu et al. |
| 2006/0293598 A1 | 12/2006 | Fraser |
| 2006/0293630 A1 | 12/2006 | Manna et al. |
| 2007/0004984 A1 | 1/2007 | Crum et al. |
| 2007/0010805 A1 | 1/2007 | Fedewa et al. |
| 2007/0016039 A1 | 1/2007 | Vortman et al. |
| 2007/0044562 A1 | 3/2007 | Sarr |
| 2007/0065420 A1 | 3/2007 | Johnson |
| 2007/0083120 A1 | 4/2007 | Cain et al. |
| 2007/0140413 A1 | 6/2007 | Saracen |
| 2007/0161902 A1 | 7/2007 | Dan |
| 2007/0167764 A1 | 7/2007 | Hynynen |
| 2007/0205785 A1 | 9/2007 | Nilsson |
| 2007/0219448 A1 | 9/2007 | Seip et al. |
| 2007/0239001 A1 | 10/2007 | Mehl et al. |
| 2007/0270683 A1 | 11/2007 | Meloy |
| 2007/0293762 A1 | 12/2007 | Sawada et al. |
| 2008/0013593 A1 | 1/2008 | Kawabata |
| 2008/0033297 A1 | 2/2008 | Sliwa |
| 2008/0033417 A1 | 2/2008 | Nields et al. |
| 2008/0051656 A1 | 2/2008 | Vaezy et al. |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0154132 A1 | 6/2008 | Hall et al. |
| 2008/0167555 A1 | 7/2008 | Qian et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0269614 A1 | 10/2008 | Adachi et al. |
| 2008/0283303 A1 | 11/2008 | Cote |
| 2008/0300485 A1 | 12/2008 | Liu et al. |
| 2008/0312561 A1 | 12/2008 | Chauhan |
| 2008/0319376 A1 | 12/2008 | Wilcox et al. |
| 2009/0012514 A1 | 1/2009 | Moonen et al. |
| 2009/0030339 A1 | 1/2009 | Cheng et al. |
| 2009/0036773 A1 | 2/2009 | Lau et al. |
| 2009/0112098 A1 | 4/2009 | Vaezy et al. |
| 2009/0171254 A1 | 7/2009 | Kushculey et al. |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2009/0230823 A1 | 9/2009 | Kushculey et al. |
| 2009/0254008 A1 | 10/2009 | Shields, Jr. |
| 2009/0287083 A1 | 11/2009 | Kushculey et al. |
| 2009/0306502 A1 | 12/2009 | Lacoste |
| 2010/0011845 A1 | 1/2010 | Laugharn et al. |
| 2010/0042020 A1 | 2/2010 | Ben-Ezra |
| 2010/0056924 A1 | 3/2010 | Powers |
| 2010/0059264 A1 | 3/2010 | Hasegawa et al. |
| 2010/0069797 A1 | 3/2010 | Cain et al. |
| 2010/0125225 A1 | 5/2010 | Gelbart et al. |
| 2010/0152624 A1 | 6/2010 | Tanis et al. |
| 2010/0163694 A1 | 7/2010 | Fadler et al. |
| 2010/0204578 A1 | 8/2010 | Schmidt et al. |
| 2010/0251823 A1 | 10/2010 | Adachi et al. |
| 2010/0255623 A1 | 10/2010 | Huang |
| 2010/0261994 A1 | 10/2010 | Davalos et al. |
| 2010/0274136 A1 | 10/2010 | Cerofolini |
| 2010/0280374 A1 | 11/2010 | Roberts et al. |
| 2010/0286518 A1 | 11/2010 | Lee et al. |
| 2010/0286519 A1 | 11/2010 | Lee et al. |
| 2010/0298744 A1 | 11/2010 | Altshuler et al. |
| 2010/0305432 A1 | 12/2010 | Duhay et al. |
| 2010/0317971 A1 | 12/2010 | Fan et al. |
| 2010/0318002 A1 | 12/2010 | Prus et al. |
| 2011/0072970 A1 | 3/2011 | Slobodzian et al. |
| 2011/0112400 A1 | 5/2011 | Emery et al. |
| 2011/0118600 A1 | 5/2011 | Gertner |
| 2011/0118602 A1 | 5/2011 | Weng et al. |
| 2011/0144490 A1 | 6/2011 | Davis et al. |
| 2011/0144545 A1 | 6/2011 | Fan et al. |
| 2011/0172529 A1 | 7/2011 | Gertner |
| 2011/0178444 A1 | 7/2011 | Slayton et al. |
| 2011/0208059 A1 | 8/2011 | Cerofolini |
| 2011/0245671 A1 | 10/2011 | Sato |
| 2011/0251528 A1 | 10/2011 | Canney et al. |
| 2011/0257524 A1 | 10/2011 | Gertner |
| 2011/0257561 A1 | 10/2011 | Gertner et al. |
| 2011/0263967 A1 | 10/2011 | Bailey et al. |
| 2011/0270136 A1 | 11/2011 | Vitek et al. |
| 2011/0302719 A1 | 12/2011 | Schwirian et al. |
| 2011/0319765 A1 | 12/2011 | Gertner |
| 2011/0319927 A1 | 12/2011 | Nita |
| 2012/0029337 A1 | 2/2012 | Aoyagi |
| 2012/0029353 A1 | 2/2012 | Slayton et al. |
| 2012/0029393 A1 | 2/2012 | Lee |
| 2012/0046592 A1 | 2/2012 | Albright et al. |
| 2012/0059264 A1 | 3/2012 | Hope Simpson et al. |
| 2012/0059285 A1 | 3/2012 | Soltani et al. |
| 2012/0065492 A1 | 3/2012 | Gertner et al. |
| 2012/0065493 A1 | 3/2012 | Gertner |
| 2012/0065494 A1 | 3/2012 | Gertner et al. |
| 2012/0092724 A1 | 4/2012 | Pettis |
| 2012/0111339 A1 | 5/2012 | Barthe et al. |
| 2012/0130288 A1 | 5/2012 | Holland et al. |
| 2012/0136279 A1 | 5/2012 | Tanaka et al. |
| 2012/0158013 A1 | 6/2012 | Stefanchik et al. |
| 2012/0172720 A1 | 7/2012 | Asami et al. |
| 2012/0189998 A1 | 7/2012 | Kruecker et al. |
| 2012/0215157 A1 | 8/2012 | Berryman et al. |
| 2012/0232388 A1 | 9/2012 | Curra et al. |
| 2012/0253176 A1 | 10/2012 | Dumoulin |
| 2012/0259250 A1 | 10/2012 | Sapozhnikov et al. |
| 2012/0271167 A1 | 10/2012 | Holland et al. |
| 2012/0271223 A1 | 10/2012 | Khanna |
| 2012/0281902 A1 | 11/2012 | Oikawa et al. |
| 2013/0051178 A1 | 2/2013 | Rybyanets |
| 2013/0053691 A1 | 2/2013 | Kawabata et al. |
| 2013/0090579 A1 | 4/2013 | Cain et al. |
| 2013/0102932 A1 | 4/2013 | Cain et al. |
| 2013/0144165 A1 | 6/2013 | Ebbini et al. |
| 2013/0172739 A1 | 7/2013 | Paladini |
| 2013/0190623 A1 | 7/2013 | Bertolina et al. |
| 2013/0190661 A1 | 7/2013 | Wing et al. |
| 2013/0255426 A1 | 10/2013 | Kassow et al. |
| 2013/0257224 A1 | 10/2013 | Wodnicki et al. |
| 2013/0261467 A1 | 10/2013 | Dausch et al. |
| 2013/0267853 A1 | 10/2013 | Dausch et al. |
| 2013/0303906 A1 | 11/2013 | Cain et al. |
| 2014/0005521 A1 | 1/2014 | Kohler et al. |
| 2014/0030806 A1 | 1/2014 | Dudley et al. |
| 2014/0039358 A1 | 2/2014 | Zhou et al. |
| 2014/0046181 A1 | 2/2014 | Benchimol et al. |

(56) References Cited

U.S. PATENT DOCUMENTS

| | | |
|---|---|---|
| 2014/0058293 A1 | 2/2014 | Hynynen et al. |
| 2014/0058294 A1 | 2/2014 | Gross et al. |
| 2014/0073995 A1 | 3/2014 | Teofilovic et al. |
| 2014/0074076 A1 | 3/2014 | Gertner |
| 2014/0088613 A1 | 3/2014 | Seo et al. |
| 2014/0100459 A1 | 4/2014 | Xu et al. |
| 2014/0112107 A1 | 4/2014 | Guo et al. |
| 2014/0128734 A1 | 5/2014 | Genstler et al. |
| 2014/0180072 A1 | 6/2014 | Davies |
| 2014/0180273 A1 | 6/2014 | Nair |
| 2014/0200489 A1 | 7/2014 | Behar et al. |
| 2014/0243664 A1 | 8/2014 | El-Sayed et al. |
| 2014/0288428 A1 | 9/2014 | Rothberg et al. |
| 2014/0316269 A1 | 10/2014 | Zhang et al. |
| 2014/0324034 A1 | 10/2014 | Assaf et al. |
| 2014/0330124 A1 | 11/2014 | Carol |
| 2014/0378832 A1 | 12/2014 | Sanghvi et al. |
| 2014/0378964 A1 | 12/2014 | Pearson |
| 2015/0011875 A1 | 1/2015 | Noordhoek et al. |
| 2015/0063668 A1 | 3/2015 | You et al. |
| 2015/0073261 A1 | 3/2015 | Kohler et al. |
| 2015/0080926 A1 | 3/2015 | Emery |
| 2015/0148659 A1 | 5/2015 | Vahala |
| 2015/0151141 A1 | 6/2015 | Arnal et al. |
| 2015/0190121 A1 | 7/2015 | Slayton et al. |
| 2015/0190659 A1 | 7/2015 | Kolher |
| 2015/0196239 A1 | 7/2015 | Meehan et al. |
| 2015/0224347 A1 | 8/2015 | Barthe et al. |
| 2015/0257779 A1 | 9/2015 | Sinelnikov et al. |
| 2015/0258352 A1 | 9/2015 | Lin et al. |
| 2015/0265243 A1 | 9/2015 | Kelly |
| 2015/0273246 A1 | 10/2015 | Darlington et al. |
| 2015/0297177 A1 | 10/2015 | Boctor et al. |
| 2016/0004933 A1 | 1/2016 | Hu et al. |
| 2016/0038665 A1 | 2/2016 | Schaefer et al. |
| 2016/0114194 A1 | 4/2016 | Gertner |
| 2016/0120572 A1 | 5/2016 | Lee |
| 2016/0135782 A1 | 5/2016 | Chen et al. |
| 2016/0151618 A1 | 6/2016 | Powers et al. |
| 2016/0184614 A1 | 6/2016 | Matula et al. |
| 2016/0206341 A1 | 7/2016 | Slayton |
| 2016/0206867 A1 | 7/2016 | Hossack et al. |
| 2016/0249859 A1 | 9/2016 | Babkin et al. |
| 2016/0287909 A1 | 10/2016 | Maxwell et al. |
| 2016/0303166 A1 | 10/2016 | Katz et al. |
| 2016/0331583 A1 | 11/2016 | Geringer |
| 2016/0331585 A1 | 11/2016 | Kim |
| 2016/0339273 A1 | 11/2016 | Al Mayiah |
| 2016/0345938 A1 | 12/2016 | Tanter et al. |
| 2016/0354087 A1 | 12/2016 | Noonan et al. |
| 2016/0361574 A1 | 12/2016 | Barthe et al. |
| 2017/0000376 A1 | 1/2017 | Partanen et al. |
| 2017/0042521 A1 | 2/2017 | Popovic et al. |
| 2017/0049463 A1 | 2/2017 | Popovic et al. |
| 2017/0071515 A1 | 3/2017 | Chevillet et al. |
| 2017/0072227 A1 | 3/2017 | Khokhlova et al. |
| 2017/0072228 A1 | 3/2017 | Wang et al. |
| 2017/0079519 A1 | 3/2017 | Sung et al. |
| 2017/0100145 A1 | 4/2017 | Khoklova et al. |
| 2017/0120080 A1 | 5/2017 | Phillips et al. |
| 2017/0165046 A1 | 6/2017 | Johnson et al. |
| 2017/0183062 A1 | 6/2017 | Lee |
| 2017/0197099 A1 | 7/2017 | Ruebel et al. |
| 2017/0232277 A1 | 8/2017 | Hall et al. |
| 2017/0263846 A1 | 9/2017 | Nakamura et al. |
| 2017/0281983 A1 | 10/2017 | Marquet et al. |
| 2017/0326589 A1 | 11/2017 | Sudol |
| 2018/0000444 A1 | 1/2018 | Dayton et al. |
| 2018/0008787 A1 | 1/2018 | Schriver et al. |
| 2018/0028841 A1 | 2/2018 | Konofagou et al. |
| 2018/0064412 A1 | 3/2018 | Messas et al. |
| 2018/0161086 A1 | 6/2018 | Davalos et al. |
| 2018/0169444 A1 | 6/2018 | Averkiou et al. |
| 2018/0206816 A1 | 7/2018 | Prus et al. |
| 2018/0207029 A1 | 7/2018 | Herekar et al. |
| 2018/0236271 A1 | 8/2018 | Tanter et al. |
| 2018/0317884 A1 | 11/2018 | Chapelon et al. |
| 2018/0374471 A1 | 12/2018 | Dirksen et al. |
| 2019/0000422 A1 | 1/2019 | West et al. |
| 2019/0023804 A1 | 1/2019 | Onik et al. |
| 2019/0082998 A1 | 3/2019 | Nowroozi et al. |
| 2019/0105113 A1 | 4/2019 | Popovic et al. |
| 2019/0275353 A1 | 9/2019 | Cannata et al. |
| 2019/0282294 A1 | 9/2019 | Davalos et al. |
| 2019/0314045 A1 | 10/2019 | Cunitz et al. |
| 2019/0320904 A1 | 10/2019 | Mei |
| 2019/0323086 A1 | 10/2019 | Leuthardt et al. |
| 2019/0328500 A1 | 10/2019 | Cichon et al. |
| 2020/0010575 A1 | 1/2020 | Hode et al. |
| 2020/0037990 A1 | 2/2020 | Qiao et al. |
| 2020/0055085 A1 | 2/2020 | Taffler |
| 2020/0078608 A1 | 3/2020 | Maxwell et al. |
| 2020/0107843 A1 | 4/2020 | Goertz et al. |
| 2020/0164231 A1* | 5/2020 | Cannata ................ A61B 34/30 |
| 2020/0182989 A1 | 6/2020 | Freeman et al. |
| 2020/0194117 A1 | 6/2020 | Krieger et al. |
| 2020/0253550 A1 | 8/2020 | Nair |
| 2020/0254285 A1 | 8/2020 | Jang et al. |
| 2020/0260964 A1 | 8/2020 | Collins et al. |
| 2020/0282239 A1 | 9/2020 | Beder et al. |
| 2020/0289080 A1 | 9/2020 | Yang et al. |
| 2020/0305842 A1 | 10/2020 | Rosenzweig et al. |
| 2020/0308785 A1 | 10/2020 | Sennhauser |
| 2020/0323515 A1 | 10/2020 | Levy |
| 2020/0330039 A1 | 10/2020 | Burkett et al. |
| 2020/0330075 A1 | 10/2020 | O'Reilly et al. |
| 2020/0346044 A1 | 11/2020 | Woodcare et al. |
| 2020/0353293 A1 | 11/2020 | Khokhlova et al. |
| 2020/0367835 A1 | 11/2020 | Anderson |
| 2020/0375576 A1 | 12/2020 | Moulton |
| 2020/0405258 A1 | 12/2020 | Dayton et al. |
| 2020/0405259 A1 | 12/2020 | Merritt |
| 2021/0000541 A1 | 1/2021 | Levy et al. |
| 2021/0009936 A1 | 1/2021 | Kamen et al. |
| 2021/0022703 A1 | 1/2021 | Nair |
| 2021/0022714 A1 | 1/2021 | Zagrodsky et al. |
| 2021/0100527 A1 | 4/2021 | Martin |
| 2021/0108866 A1 | 4/2021 | Lucht et al. |
| 2021/0161398 A1 | 6/2021 | Millett et al. |
| 2021/0169515 A1 | 6/2021 | Pahk et al. |
| 2021/0170204 A1 | 6/2021 | Vortman et al. |
| 2021/0170205 A1 | 6/2021 | Vortman et al. |
| 2021/0187331 A1 | 6/2021 | Zadicario et al. |
| 2021/0196295 A1 | 7/2021 | Goudot et al. |
| 2021/0220607 A1 | 7/2021 | Sasamine et al. |
| 2021/0330294 A1 | 10/2021 | Hynynen et al. |
| 2021/0353161 A1 | 11/2021 | Merritt et al. |
| 2021/0386451 A1 | 12/2021 | Escudero et al. |
| 2021/0401366 A1 | 12/2021 | Weiss et al. |
| 2021/0401400 A1 | 12/2021 | Sheehan et al. |
| 2022/0008036 A1 | 1/2022 | Gulsen et al. |
| 2022/0022845 A1 | 1/2022 | Cort |
| 2022/0031287 A1 | 2/2022 | Ebbini et al. |
| 2022/0043143 A1 | 2/2022 | Prus et al. |
| 2022/0059227 A1 | 2/2022 | Park et al. |
| 2022/0079563 A1 | 3/2022 | Kemp |
| 2022/0087640 A1 | 3/2022 | Minas et al. |
| 2022/0110809 A1 | 4/2022 | Grindstaff et al. |
| 2022/0166462 A1 | 5/2022 | Deurenberg et al. |
| 2022/0167920 A1 | 6/2022 | Margolis |
| 2022/0168470 A1 | 6/2022 | Ricotti et al. |
| 2022/0196771 A1 | 6/2022 | Zur et al. |
| 2022/0202483 A1 | 6/2022 | Gertner |
| 2022/0203139 A1 | 6/2022 | Shapira |
| 2022/0219019 A1 | 7/2022 | Xu et al. |
| 2022/0233890 A1 | 7/2022 | Hynynen et al. |
| 2022/0240890 A1 | 8/2022 | Hancock et al. |
| 2022/0257329 A1 | 8/2022 | Stigall et al. |
| 2022/0280233 A1 | 9/2022 | Park et al. |
| 2022/0280367 A1 | 9/2022 | Diodato et al. |
| 2022/0296211 A1 | 9/2022 | Saroha et al. |
| 2022/0338750 A1 | 10/2022 | Allen et al. |
| 2022/0346756 A1 | 11/2022 | Chen |
| 2022/0370025 A1 | 11/2022 | Regensburger et al. |

(56)     References Cited

U.S. PATENT DOCUMENTS

| | | |
|---|---|---|
| 2022/0386970 A1 | 12/2022 | Merritt |
| 2022/0395333 A1 | 12/2022 | Merritt et al. |
| 2022/0409171 A1 | 12/2022 | Sudol et al. |
| 2022/0409858 A1 | 12/2022 | Lin |
| 2023/0000466 A1 | 1/2023 | Levy et al. |
| 2023/0000469 A1 | 1/2023 | Prus et al. |
| 2023/0008714 A1 | 1/2023 | Rajguru et al. |
| 2023/0012365 A1 | 1/2023 | Alpert et al. |
| 2023/0024998 A1 | 1/2023 | Greenberg |
| 2023/0031859 A1 | 2/2023 | Davies et al. |
| 2023/0037603 A1 | 2/2023 | Pombo et al. |
| 2023/0038498 A1 | 2/2023 | Xu et al. |
| 2023/0038543 A1 | 2/2023 | Minas et al. |
| 2023/0042834 A1 | 2/2023 | Henderson et al. |
| 2023/0045488 A1 | 2/2023 | Rajguru et al. |
| 2023/0048979 A1 | 2/2023 | Lindenmoyer et al. |
| 2023/0061534 A1 | 3/2023 | Stopek |
| 2023/0073447 A1 | 3/2023 | Minas et al. |
| 2023/0100912 A1 | 3/2023 | Amar et al. |
| 2023/0112722 A1 | 4/2023 | Hoffman et al. |
| 2023/0114972 A1 | 4/2023 | Bigham et al. |
| 2023/0121688 A1 | 4/2023 | Begin et al. |
| 2023/0126520 A1 | 4/2023 | Lenich et al. |
| 2023/0145064 A1 | 5/2023 | Vortman et al. |
| 2023/0181140 A1 | 6/2023 | Cohen et al. |
| 2023/0181156 A1 | 6/2023 | Cohen et al. |
| 2023/0190119 A1 | 6/2023 | Groenland et al. |
| 2023/0190215 A1 | 6/2023 | Nachtomy et al. |
| 2023/0190224 A1 | 6/2023 | Rajguru et al. |
| 2023/0190225 A1 | 6/2023 | Cohen et al. |
| 2023/0190226 A1 | 6/2023 | Rajguru et al. |
| 2023/0190227 A1 | 6/2023 | Cohen et al. |
| 2023/0190228 A1 | 6/2023 | Cohen et al. |
| 2023/0190229 A1 | 6/2023 | Cohen et al. |
| 2023/0190230 A1 | 6/2023 | Yang et al. |
| 2023/0191162 A1 | 6/2023 | Yau et al. |
| 2023/0196569 A1 | 6/2023 | Cohen et al. |
| 2023/0200899 A1 | 6/2023 | Nair |
| 2023/0201553 A1 | 6/2023 | Levy et al. |
| 2023/0218230 A1 | 7/2023 | Wu et al. |
| 2023/0218262 A1 | 7/2023 | Boutelle et al. |
| 2023/0218266 A1 | 7/2023 | Stigall et al. |
| 2023/0218269 A1 | 7/2023 | Alpert et al. |
| 2023/0218930 A1 | 7/2023 | Stopek et al. |
| 2023/0240615 A1 | 8/2023 | May et al. |
| 2023/0240647 A1 | 8/2023 | Minas et al. |
| 2023/0240663 A1 | 8/2023 | Lafond et al. |
| 2023/0240792 A1 | 8/2023 | Rakic et al. |
| 2023/0255597 A1 | 8/2023 | O'Reilly et al. |
| 2023/0260601 A1 | 8/2023 | Abel et al. |
| 2023/0263507 A1 | 8/2023 | Groenland et al. |
| 2023/0270388 A1 | 8/2023 | Richardson et al. |
| 2023/0293148 A1 | 9/2023 | Stigall et al. |
| 2023/0293149 A1 | 9/2023 | Stigall et al. |
| 2023/0309859 A1 | 10/2023 | Sreedhar et al. |
| 2023/0310899 A1 | 10/2023 | Hall et al. |
| 2023/0310900 A1 | 10/2023 | Cannata et al. |
| 2023/0320600 A1 | 10/2023 | Tochterman et al. |
| 2023/0321327 A1 | 10/2023 | Maxwell et al. |
| 2023/0321398 A1 | 10/2023 | May |
| 2023/0329559 A1 | 10/2023 | Xu et al. |
| 2023/0333617 A1 | 10/2023 | Spencer et al. |
| 2023/0334659 A1 | 10/2023 | Marama et al. |
| 2023/0334677 A1 | 10/2023 | Sturm |
| 2023/0338010 A1 | 10/2023 | Sturm |
| 2023/0372025 A1 | 11/2023 | Van der Zaag et al. |
| 2023/0381544 A1 | 11/2023 | Penot et al. |
| 2023/0389891 A1 | 12/2023 | Cohen et al. |
| 2023/0398381 A1 | 12/2023 | Vitek et al. |
| 2024/0000422 A1 | 1/2024 | Cort |
| 2024/0000426 A1 | 1/2024 | Davies et al. |
| 2024/0001157 A1 | 1/2024 | Cannata et al. |
| 2024/0001158 A1 | 1/2024 | Cannata et al. |
| 2024/0023928 A1 | 1/2024 | Di Tullio et al. |
| 2024/0023930 A1 | 1/2024 | Anderson |
| 2024/0023941 A1 | 1/2024 | Rhodes |
| 2024/0024705 A1 | 1/2024 | Xu et al. |
| 2024/0033542 A1 | 2/2024 | Cain et al. |
| 2024/0065632 A1 | 2/2024 | Burkett |
| 2024/0081754 A1 | 3/2024 | Regensburger et al. |
| 2024/0138807 A1 | 5/2024 | Minas |
| 2024/0139552 A1 | 5/2024 | Duryea et al. |
| 2024/0139553 A1 | 5/2024 | Miller et al. |
| 2024/0149078 A1 | 5/2024 | Duryea et al. |
| 2024/0165666 A1 | 5/2024 | Hynynen et al. |
| 2024/0188929 A1 | 6/2024 | Minas et al. |
| 2024/0188931 A1 | 6/2024 | Ossmann et al. |
| 2024/0189267 A1 | 6/2024 | Bogott et al. |
| 2024/0189627 A1 | 6/2024 | Bogott et al. |
| 2024/0189628 A1 | 6/2024 | Grumbir et al. |
| 2024/0207654 A1 | 6/2024 | Xu et al. |
| 2024/0225592 A1 | 7/2024 | May et al. |
| 2024/0245374 A1 | 7/2024 | Jenkins et al. |
| 2024/0245390 A1 | 7/2024 | Winkler Brown et al. |
| 2024/0245465 A1 | 7/2024 | Jenkins et al. |
| 2024/0269491 A1 | 8/2024 | Xu et al. |
| 2024/0285249 A1 | 8/2024 | May |
| 2024/0285978 A1 | 8/2024 | Xu et al. |
| 2024/0299092 A1 | 9/2024 | Boinagrov et al. |
| 2024/0307027 A1 | 9/2024 | Minas |
| 2024/0307708 A1 | 9/2024 | Cannata et al. |
| 2024/0315713 A1 | 9/2024 | Maxwell et al. |
| 2024/0316367 A1 | 9/2024 | Cannata et al. |
| 2024/0335680 A1 | 10/2024 | Achrol et al. |
| 2024/0341732 A1 | 10/2024 | Hoffman et al. |
| 2024/0350118 A1 | 10/2024 | Jenkins et al. |
| 2024/0350153 A1 | 10/2024 | Cannata et al. |
| 2024/0350207 A1 | 10/2024 | Stopek |
| 2024/0374242 A1 | 11/2024 | Merritt et al. |
| 2024/0399174 A1 | 12/2024 | Cannata et al. |
| 2024/0408416 A1 | 12/2024 | Cannata et al. |
| 2025/0018227 A1 | 1/2025 | Son et al. |
| 2025/0040912 A1 | 2/2025 | Levy et al. |
| 2025/0041577 A1 | 2/2025 | Shapira et al. |
| 2025/0072872 A1 | 3/2025 | Nachtomy et al. |
| 2025/0160786 A1 | 5/2025 | Zagrodsky et al. |
| 2025/0186808 A1 | 6/2025 | Cannata et al. |
| 2025/0249289 A1 | 8/2025 | Miller et al. |
| 2025/0256132 A1 | 8/2025 | Xu et al. |
| 2025/0263798 A1 | 8/2025 | Achrol et al. |
| 2025/0320390 A1 | 10/2025 | Shachaf et al. |
| 2025/0344999 A1 | 11/2025 | Wu et al. |
| 2025/0349023 A1 | 11/2025 | Rajguru et al. |

FOREIGN PATENT DOCUMENTS

| | | |
|---|---|---|
| AU | 2021406651 B2 | 4/2025 |
| AU | 2022215411 B2 | 5/2025 |
| BR | 112018017326 B1 | 12/2022 |
| BR | 102023017634 A2 | 1/2025 |
| CA | 3073552 A1 | 3/2019 |
| CA | 3101381 A1 | 11/2019 |
| CA | 3055856 A1 | 4/2020 |
| CA | 3130859 A1 | 10/2020 |
| CA | 3153080 A1 | 4/2021 |
| CA | 2910561 C | 7/2021 |
| CA | 2908740 C | 10/2021 |
| CA | 2980976 C | 3/2023 |
| CA | 2840014 C | 8/2023 |
| CN | 1669672 A | 9/2005 |
| CN | 1732031 A | 2/2006 |
| CN | 201197744 Y | 2/2009 |
| CN | 102292123 A | 12/2011 |
| CN | 102481164 A | 5/2012 |
| CN | 102665585 A | 9/2012 |
| CN | 103537016 A | 1/2014 |
| CN | 103648361 A | 3/2014 |
| CN | 103812477 A | 5/2014 |
| CN | 104013444 A | 9/2014 |
| CN | 104135938 A | 11/2014 |
| CN | 104208822 A | 12/2014 |
| CN | 106999076 B | 8/2017 |
| CN | 109185113 A | 1/2019 |
| CN | 109689160 A | 4/2019 |

(56) References Cited

FOREIGN PATENT DOCUMENTS

| | | | |
|---|---|---|---|
| CN | 208725992 | U | 4/2019 |
| CN | 111565642 | A | 8/2020 |
| CN | 111655337 | A | 9/2020 |
| CN | 111699022 | A | 9/2020 |
| CN | 111712300 | A | 9/2020 |
| CN | 111712301 | A | 9/2020 |
| CN | 106999053 | B | 10/2020 |
| CN | 107660137 | B | 10/2020 |
| CN | 111757769 | A | 10/2020 |
| CN | 112204412 | A | 1/2021 |
| CN | 112236195 | A | 1/2021 |
| CN | 106661535 | B | 3/2021 |
| CN | 112533673 | A | 3/2021 |
| CN | 112566694 | A | 3/2021 |
| CN | 106999054 | B | 5/2021 |
| CN | 106793997 | B | 6/2021 |
| CN | 107530049 | B | 6/2021 |
| CN | 112912011 | A | 6/2021 |
| CN | 112912012 | A | 6/2021 |
| CN | 112912013 | A | 6/2021 |
| CN | 112969413 | A | 6/2021 |
| CN | 112996445 | A | 6/2021 |
| CN | 113167877 | A | 7/2021 |
| CN | 113196080 | A | 7/2021 |
| CN | 109196369 | B | 8/2021 |
| CN | 109200484 | B | 8/2021 |
| CN | 113316419 | A | 8/2021 |
| CN | 113329788 | A | 8/2021 |
| CN | 109640830 | B | 10/2021 |
| CN | 113473917 | A | 10/2021 |
| CN | 113507946 | A | 10/2021 |
| CN | 113518588 | A | 10/2021 |
| CN | 113705586 | A | 11/2021 |
| CN | 110662575 | B | 12/2021 |
| CN | 113905666 | A | 1/2022 |
| CN | 114222536 | A | 3/2022 |
| CN | 114366154 | A | 4/2022 |
| CN | 114423362 | A | 4/2022 |
| CN | 110248606 | B | 6/2022 |
| CN | 115227992 | A | 10/2022 |
| CN | 109843181 | B | 11/2022 |
| CN | 115461000 | A | 12/2022 |
| CN | 115515504 | A | 12/2022 |
| CN | 109091768 | B | 3/2023 |
| CN | 115779285 | A | 3/2023 |
| CN | 115779287 | A | 3/2023 |
| CN | 115813438 | A | 3/2023 |
| CN | 111032157 | B | 4/2023 |
| CN | 115916035 | A | 4/2023 |
| CN | 110958858 | B | 5/2023 |
| CN | 116172611 | A | 5/2023 |
| CN | 111655337 | B | 6/2023 |
| CN | 109416908 | B | 7/2023 |
| CN | 116507295 | A | 7/2023 |
| CN | 107529989 | B | 8/2023 |
| CN | 111372522 | B | 8/2023 |
| CN | 116617589 | A | 8/2023 |
| CN | 112236195 | B | 9/2023 |
| CN | 114555247 | B | 9/2023 |
| CN | 116744856 | A | 9/2023 |
| CN | 116761554 | A | 9/2023 |
| CN | 109416907 | B | 10/2023 |
| CN | 117321444 | A | 12/2023 |
| CN | 117500437 | A | 2/2024 |
| CN | 117580499 | A | 2/2024 |
| CN | 111212606 | B | 3/2024 |
| CN | 113490459 | B | 5/2024 |
| CN | 118414127 | A | 7/2024 |
| CN | 112601498 | B | 9/2024 |
| CN | 118678921 | A | 9/2024 |
| CN | 113271866 | B | 10/2024 |
| CN | 112603273 | B | 12/2024 |
| CN | 112639754 | B | 12/2024 |
| CN | 119367006 | A | 1/2025 |
| CN | 112704620 | B | 2/2025 |
| CN | 114287963 | B | 2/2025 |
| CN | 110410498 | B | 3/2025 |
| CN | 112426634 | B | 3/2025 |
| CN | 309226917 | S | 4/2025 |
| CN | 309226918 | S | 4/2025 |
| CN | 112545816 | B | 5/2025 |
| CN | 112546464 | B | 6/2025 |
| CN | 112618971 | B | 6/2025 |
| CN | 113040905 | B | 6/2025 |
| CN | 309337123 | S | 6/2025 |
| CN | 309353839 | S | 6/2025 |
| CN | 309353840 | S | 6/2025 |
| CN | 114340682 | B | 7/2025 |
| CN | 115515567 | B | 7/2025 |
| CN | 223054702 | U | 7/2025 |
| CN | 223081906 | U | 7/2025 |
| CN | 112546465 | B | 8/2025 |
| CN | 309451067 | S | 8/2025 |
| CN | 309457819 | S | 8/2025 |
| CN | 309457820 | S | 8/2025 |
| CN | 309464789 | S | 8/2025 |
| CN | 111991712 | B | 9/2025 |
| CN | 223323919 | U | 9/2025 |
| CN | 112494106 | B | 10/2025 |
| CN | 114638798 | B | 10/2025 |
| CN | 223504729 | U | 11/2025 |
| DE | 3220751 | A1 | 12/1983 |
| DE | 3544628 | A1 | 6/1987 |
| DE | 3817094 | A1 | 11/1989 |
| DE | 4012760 | A1 | 5/1992 |
| DE | 602020055151 | T2 | 7/2025 |
| DE | 602022018890 | T2 | 8/2025 |
| DE | 602020058523 | T2 | 9/2025 |
| DE | 602020059056 | T2 | 9/2025 |
| DE | 602022021590 | T2 | 9/2025 |
| DE | 112023005080 | T5 | 10/2025 |
| DE | 602017092008 | T2 | 10/2025 |
| DE | 602022022517 | T2 | 10/2025 |
| EP | 0017382 | A1 | 10/1980 |
| EP | 0320303 | A2 | 6/1989 |
| EP | 0332871 | A2 | 9/1989 |
| EP | 0384831 | A2 | 8/1990 |
| EP | 0619156 | A1 | 10/1994 |
| EP | 0755653 | A1 | 1/1997 |
| EP | 1374785 | A1 | 1/2004 |
| EP | 1504713 | A1 | 2/2005 |
| EP | 1566201 | A2 | 8/2005 |
| EP | 2397188 | A1 | 12/2011 |
| EP | 2934308 | B1 | 10/2015 |
| EP | 2934309 | B1 | 10/2015 |
| EP | 3097180 | B1 | 11/2016 |
| EP | 3100767 | B1 | 11/2019 |
| EP | 2759003 | B1 | 8/2020 |
| EP | 3558457 | A4 | 8/2020 |
| EP | 3700629 | A1 | 9/2020 |
| EP | 3218829 | B1 | 10/2020 |
| EP | 3229688 | B1 | 10/2020 |
| EP | 2887989 | B1 | 2/2021 |
| EP | 3777689 | A1 | 2/2021 |
| EP | 2938253 | B1 | 3/2021 |
| EP | 3076864 | B1 | 3/2021 |
| EP | 2802276 | B1 | 4/2021 |
| EP | 2809221 | B1 | 4/2021 |
| EP | 3801761 | A1 | 4/2021 |
| EP | 3801762 | A2 | 4/2021 |
| EP | 3801763 | A1 | 4/2021 |
| EP | 2967369 | B1 | 5/2021 |
| EP | 2967488 | B1 | 6/2021 |
| EP | 3184048 | B1 | 6/2021 |
| EP | 2967370 | B1 | 9/2021 |
| EP | 3482390 | B1 | 9/2021 |
| EP | 3870067 | A1 | 9/2021 |
| EP | 3870069 | A1 | 9/2021 |
| EP | 3876843 | A1 | 9/2021 |
| EP | 2931130 | B1 | 10/2021 |
| EP | 2934304 | B1 | 10/2021 |
| EP | 3887843 | A1 | 10/2021 |
| EP | 3888534 | A1 | 10/2021 |
| EP | 3895604 | A1 | 10/2021 |

(56) References Cited

FOREIGN PATENT DOCUMENTS

| | | | |
|---|---|---|---|
| EP | 3897391 | A1 | 10/2021 |
| EP | 3229672 | B1 | 11/2021 |
| EP | 3902603 | A1 | 11/2021 |
| EP | 3903672 | A1 | 11/2021 |
| EP | 2964096 | B1 | 12/2021 |
| EP | 3930776 | A1 | 1/2022 |
| EP | 3545829 | B1 | 3/2022 |
| EP | 3959530 | A2 | 3/2022 |
| EP | 3060129 | B1 | 4/2022 |
| EP | 3986296 | A1 | 4/2022 |
| EP | 3988167 | A1 | 4/2022 |
| EP | 2914166 | B1 | 5/2022 |
| EP | 3229674 | B1 | 5/2022 |
| EP | 2779907 | B1 | 6/2022 |
| EP | 3102098 | B1 | 6/2022 |
| EP | 2965263 | B1 | 7/2022 |
| EP | 2726152 | B1 | 8/2022 |
| EP | 4042936 | A1 | 8/2022 |
| EP | 3298959 | B2 | 9/2022 |
| EP | 2931131 | B1 | 11/2022 |
| EP | 2938268 | B1 | 11/2022 |
| EP | 3581103 | B1 | 11/2022 |
| EP | 4087492 | A1 | 11/2022 |
| EP | 4093470 | A1 | 11/2022 |
| EP | 3091905 | B1 | 12/2022 |
| EP | 4098203 | A1 | 12/2022 |
| EP | 2950737 | B1 | 1/2023 |
| EP | 3057496 | B1 | 1/2023 |
| EP | 4114274 | A1 | 1/2023 |
| EP | 4117534 | A1 | 1/2023 |
| EP | 2869804 | B1 | 2/2023 |
| EP | 2938265 | B1 | 2/2023 |
| EP | 3024403 | B1 | 3/2023 |
| EP | 4138672 | A1 | 3/2023 |
| EP | 4151156 | A1 | 3/2023 |
| EP | 2938271 | B1 | 4/2023 |
| EP | 4161360 | A1 | 4/2023 |
| EP | 4179995 | A2 | 5/2023 |
| EP | 3171764 | B1 | 6/2023 |
| EP | 4201342 | A1 | 6/2023 |
| EP | 2931132 | B1 | 7/2023 |
| EP | 3229695 | B1 | 7/2023 |
| EP | 4209178 | A1 | 7/2023 |
| EP | 4209179 | A1 | 7/2023 |
| EP | 4226864 | A1 | 8/2023 |
| EP | 4230121 | A2 | 8/2023 |
| EP | 4230146 | A1 | 8/2023 |
| EP | 4233972 | A2 | 8/2023 |
| EP | 2866733 | B1 | 9/2023 |
| EP | 3870069 | B1 | 9/2023 |
| EP | 4247489 | A1 | 9/2023 |
| EP | 3484371 | B1 | 10/2023 |
| EP | 3658037 | B1 | 10/2023 |
| EP | 3685874 | B1 | 10/2023 |
| EP | 3870070 | B1 | 10/2023 |
| EP | 4257151 | A1 | 10/2023 |
| EP | 2938255 | B1 | 11/2023 |
| EP | 3229906 | B1 | 11/2023 |
| EP | 3764914 | B1 | 11/2023 |
| EP | 3903672 | B1 | 11/2023 |
| EP | 4272654 | A2 | 11/2023 |
| EP | 4275609 | A2 | 11/2023 |
| EP | 3316804 | B1 | 12/2023 |
| EP | 3519109 | B1 | 12/2023 |
| EP | 3166479 | B1 | 1/2024 |
| EP | 3537984 | B1 | 1/2024 |
| EP | 3908195 | B1 | 2/2024 |
| EP | 3182920 | B1 | 3/2024 |
| EP | 3174643 | B1 | 4/2024 |
| EP | 3814917 | B1 | 4/2024 |
| EP | 4349283 | A1 | 4/2024 |
| EP | 3681419 | B1 | 5/2024 |
| EP | 4368118 | A2 | 5/2024 |
| EP | 2804525 | B1 | 6/2024 |
| EP | 4380667 | A2 | 6/2024 |
| EP | 4385428 | A1 | 6/2024 |
| EP | 4459545 | A1 | 6/2024 |
| EP | 3324836 | B1 | 9/2024 |
| EP | 3624732 | B1 | 11/2024 |
| EP | 4289415 | A4 | 1/2025 |
| EP | 4406484 | B1 | 1/2025 |
| EP | 3190958 | B1 | 2/2025 |
| EP | 4282471 | B1 | 3/2025 |
| EP | 3277378 | B1 | 5/2025 |
| EP | 4574206 | A1 | 6/2025 |
| EP | 4041463 | B1 | 8/2025 |
| EP | 3986296 | B1 | 9/2025 |
| EP | 4275744 | B1 | 10/2025 |
| EP | 4633490 | A1 | 10/2025 |
| ES | 2774069 | T3 | 7/2020 |
| ES | 2819552 | T3 | 4/2021 |
| ES | 2829822 | T3 | 6/2021 |
| ES | 2998435 | T3 | 2/2025 |
| ES | 3005837 | T3 | 3/2025 |
| GB | 2099582 | A | 12/1982 |
| HK | 1245715 | B | 1/2021 |
| IL | 254768 | A | 5/2021 |
| IL | 261285 | B | 2/2022 |
| IN | 202117039853 | A | 12/2021 |
| IN | 387413 | B | 1/2022 |
| IN | 445766 | B | 8/2023 |
| JP | 60-80779 | A | 5/1985 |
| JP | 61-196718 | A | 8/1986 |
| JP | S62144641 | A | 6/1987 |
| JP | H02104343 | A | 4/1990 |
| JP | 02-215451 | A | 8/1990 |
| JP | H0422351 | A | 1/1992 |
| JP | 06-197907 | A | 7/1994 |
| JP | 07-504339 | A | 5/1995 |
| JP | H07213527 | A | 8/1995 |
| JP | H07284499 | A | 10/1995 |
| JP | 08-84740 | A | 4/1996 |
| JP | 06-304178 | A | 5/1996 |
| JP | 08-131454 | A | 5/1996 |
| JP | 09-55571 | A | 2/1997 |
| JP | H10305041 | A | 11/1998 |
| JP | 10-512477 | A | 12/1998 |
| JP | 2000300559 | A | 10/2000 |
| JP | 2003510159 | A | 3/2003 |
| JP | 2004505660 | A | 2/2004 |
| JP | 2004249106 | A | 9/2004 |
| JP | 2005167058 | A | 6/2005 |
| JP | 2006511265 | A | 4/2006 |
| JP | 2007144225 | A | 6/2007 |
| JP | 2007520307 | A | 7/2007 |
| JP | 2008049199 | A | 3/2008 |
| JP | 2010019554 | A | 1/2010 |
| JP | 2010029650 | A | 2/2010 |
| JP | 2010204068 | A | 9/2010 |
| JP | 2013538097 | A | 10/2013 |
| JP | 2004512502 | A | 4/2014 |
| JP | 2014204876 | A | 10/2014 |
| JP | 2015002983 | A | 1/2015 |
| JP | 2015519970 | A | 7/2015 |
| JP | 2016508808 | A | 3/2016 |
| JP | 2017/506542 | A | 3/2017 |
| JP | 2017506538 | A | 3/2017 |
| JP | 2019051295 | A | 4/2019 |
| JP | 2020525167 | A | 8/2020 |
| JP | 2020525168 | A | 8/2020 |
| JP | 2020525169 | A | 8/2020 |
| JP | 6785554 | B2 | 10/2020 |
| JP | 6789944 | B2 | 11/2020 |
| JP | 2020534077 | A | 11/2020 |
| JP | 2020195788 | A | 12/2020 |
| JP | 2020535895 | A | 12/2020 |
| JP | 6832958 | B2 | 2/2021 |
| JP | 6835719 | B2 | 2/2021 |
| JP | 6838057 | B2 | 3/2021 |
| JP | 6849592 | B2 | 3/2021 |
| JP | 2021510104 | A | 4/2021 |
| JP | 6896719 | B2 | 6/2021 |
| JP | 6934933 | B2 | 9/2021 |
| JP | 6951560 | B2 | 10/2021 |

(56) References Cited

FOREIGN PATENT DOCUMENTS

| | | | |
|---|---|---|---|
| JP | 6979633 | B2 | 12/2021 |
| JP | 6980696 | B2 | 12/2021 |
| JP | 7012726 | B2 | 1/2022 |
| JP | 2022500092 | A | 1/2022 |
| JP | 2022500093 | A | 1/2022 |
| JP | 2022501080 | A | 1/2022 |
| JP | 2022504159 | A | 1/2022 |
| JP | 2022509389 | A | 1/2022 |
| JP | 2022509391 | A | 1/2022 |
| JP | 2022509392 | A | 1/2022 |
| JP | 2022509393 | A | 1/2022 |
| JP | 2022509395 | A | 1/2022 |
| JP | 2022509401 | A | 1/2022 |
| JP | 2022509453 | A | 1/2022 |
| JP | 2022510217 | A | 1/2022 |
| JP | 7019679 | B2 | 2/2022 |
| JP | 7026118 | B2 | 2/2022 |
| JP | 2022514272 | A | 2/2022 |
| JP | 2022515488 | A | 2/2022 |
| JP | 2022516078 | A | 2/2022 |
| JP | 7053500 | B2 | 4/2022 |
| JP | 2022526104 | A | 5/2022 |
| JP | 2022527043 | A | 5/2022 |
| JP | 2022095785 | A | 6/2022 |
| JP | 7171645 | B2 | 11/2022 |
| JP | 7171663 | B2 | 11/2022 |
| JP | 7175640 | B2 | 11/2022 |
| JP | 2022546288 | A | 11/2022 |
| JP | 7187715 | B2 | 12/2022 |
| JP | 2022551875 | A | 12/2022 |
| JP | 2022552229 | A | 12/2022 |
| JP | 7201819 | B2 | 1/2023 |
| JP | 7232204 | B2 | 3/2023 |
| JP | 7239466 | B2 | 3/2023 |
| JP | 7265525 | B2 | 4/2023 |
| JP | 2023071859 | A | 5/2023 |
| JP | 7292448 | B2 | 6/2023 |
| JP | 7299992 | B2 | 6/2023 |
| JP | 2023085350 | A | 6/2023 |
| JP | 7302936 | B2 | 7/2023 |
| JP | 7304344 | B2 | 7/2023 |
| JP | 7321162 | B2 | 8/2023 |
| JP | 7325430 | B2 | 8/2023 |
| JP | 7335367 | B2 | 8/2023 |
| JP | 2023116673 | A | 8/2023 |
| JP | 7340594 | B2 | 9/2023 |
| JP | 7346293 | B2 | 9/2023 |
| JP | 7351972 | B2 | 9/2023 |
| JP | 7352561 | B2 | 9/2023 |
| JP | 2023123676 | A | 9/2023 |
| JP | 2023134811 | A | 9/2023 |
| JP | 7358391 | B2 | 10/2023 |
| JP | 7359765 | B2 | 10/2023 |
| JP | 7370386 | B2 | 10/2023 |
| JP | 2023162327 | A | 11/2023 |
| JP | 2024010135 | A | 1/2024 |
| JP | 2024020483 | A | 2/2024 |
| JP | 7479288 | B2 | 5/2024 |
| JP | 7479351 | B2 | 5/2024 |
| JP | 7485383 | B2 | 5/2024 |
| JP | 7530561 | B2 | 8/2024 |
| JP | 7542708 | B2 | 8/2024 |
| JP | 2024161427 | A | 11/2024 |
| JP | 7612816 | B2 | 1/2025 |
| JP | 2025013082 | A | 1/2025 |
| JP | 7641600 | B2 | 3/2025 |
| JP | 7643694 | B2 | 3/2025 |
| JP | 2025031814 | A | 3/2025 |
| KR | 102574559 | B1 | 9/2023 |
| KR | 102764982 | B1 | 2/2025 |
| KR | 20250019597 | A | 2/2025 |
| KR | 20250022640 | A | 2/2025 |
| KR | 20250022641 | A | 2/2025 |
| KR | DM226835001 | S1 | 4/2025 |
| KR | 102854907 | B1 | 9/2025 |
| RU | 2589641 | C1 | 7/2016 |
| RU | 2839094 | C2 | 4/2025 |
| TW | 201729929 | A | 9/2017 |
| WO | WO94/06355 | A1 | 3/1994 |
| WO | WO02/32506 | A1 | 4/2002 |
| WO | WO2005/018469 | A1 | 3/2005 |
| WO | WO2008/051484 | A2 | 5/2008 |
| WO | WO2011/040054 | A1 | 7/2011 |
| WO | WO2011/092683 | A1 | 8/2011 |
| WO | WO2011/154654 | A2 | 12/2011 |
| WO | WO2014/008594 | A1 | 1/2014 |
| WO | WO2014/071386 | A1 | 5/2014 |
| WO | WO2015/000953 | A1 | 1/2015 |
| WO | WO2015/031532 | A1 | 3/2015 |
| WO | WO2015/153909 | A2 | 10/2015 |
| WO | WO2016/099279 | A1 | 6/2016 |
| WO | WO2018/149671 | A1 | 8/2018 |
| WO | WO2018/208189 | A1 | 11/2018 |
| WO | WO2019/081329 | A1 | 5/2019 |
| WO | WO2019/117926 | A1 | 6/2019 |
| WO | WO2019/122941 | A1 | 6/2019 |
| WO | WO2019/148154 | A1 | 8/2019 |
| WO | WO2020/074615 | A1 | 4/2020 |
| WO | WO2020/087049 | A1 | 4/2020 |
| WO | WO2020/112688 | A1 | 6/2020 |
| WO | WO2020/217098 | A2 | 10/2020 |
| WO | WO2020/237382 | A1 | 12/2020 |
| WO | WO2020/245660 | A1 | 12/2020 |
| WO | WO2021/014221 | A1 | 1/2021 |
| WO | WO2021/032887 | A1 | 2/2021 |
| WO | WO2021/069216 | A1 | 4/2021 |
| WO | WO2021/069971 | A1 | 4/2021 |
| WO | WO2021/089810 | A1 | 5/2021 |
| WO | WO2021/105358 | A1 | 6/2021 |
| WO | WO2021/115958 | A1 | 6/2021 |
| WO | WO2021/116763 | A1 | 6/2021 |
| WO | WO2021/122253 | A1 | 6/2021 |
| WO | WO2021/123905 | A2 | 6/2021 |
| WO | WO2021/123906 | A1 | 6/2021 |
| WO | WO2021/140042 | A1 | 7/2021 |
| WO | WO2021/142090 | A1 | 7/2021 |
| WO | WO2021/170510 | A1 | 9/2021 |
| WO | WO2021/175626 | A1 | 9/2021 |
| WO | WO2021/176275 | A1 | 9/2021 |
| WO | WO2021/178961 | A1 | 9/2021 |
| WO | WO2021/180501 | A1 | 9/2021 |
| WO | WO2021/180550 | A1 | 9/2021 |
| WO | WO2021/213927 | A1 | 10/2021 |
| WO | WO2021/249936 | A1 | 12/2021 |
| WO | WO2021/258007 | A1 | 12/2021 |
| WO | WO2022/013266 | A1 | 1/2022 |
| WO | WO2022/040493 | A1 | 2/2022 |
| WO | WO2022/047193 | A8 | 3/2022 |
| WO | WO2022/056394 | A1 | 3/2022 |
| WO | WO2022/069254 | A1 | 4/2022 |
| WO | WO2022/069303 | A2 | 4/2022 |
| WO | WO2022/069327 | A2 | 4/2022 |
| WO | WO2022/078744 | A1 | 4/2022 |
| WO | WO2022/097138 | A1 | 5/2022 |
| WO | WO2022/104683 | A1 | 5/2022 |
| WO | WO2022/106891 | A1 | 5/2022 |
| WO | WO2022/152724 | A1 | 7/2022 |
| WO | WO2022/152827 | A1 | 7/2022 |
| WO | WO2022/152828 | A1 | 7/2022 |
| WO | WO2022/228922 | A1 | 11/2022 |
| WO | WO2022/238058 | A1 | 11/2022 |
| WO | WO2022/238092 | A1 | 11/2022 |
| WO | WO2022/238229 | A1 | 11/2022 |
| WO | WO2022/238274 | A1 | 11/2022 |
| WO | WO2022/238276 | A1 | 11/2022 |
| WO | WO2022/238392 | A1 | 11/2022 |
| WO | WO2022/247242 | A1 | 12/2022 |
| WO | WO2022/258561 | A1 | 12/2022 |
| WO | WO2023/274899 | A1 | 1/2023 |
| WO | WO2023/275617 | A2 | 1/2023 |
| WO | WO2023/275771 | A1 | 1/2023 |
| WO | WO2023/012516 | A2 | 2/2023 |
| WO | WO2023/036742 | A1 | 3/2023 |
| WO | WO2023/052278 | A1 | 4/2023 |

(56) References Cited

FOREIGN PATENT DOCUMENTS

| | | | |
|---|---|---|---|
| WO | WO2023/084307 A1 | 5/2023 |
| WO | WO2023/104599 A1 | 6/2023 |
| WO | WO2023/104841 A1 | 6/2023 |
| WO | WO2023/105290 A1 | 6/2023 |
| WO | WO2023/110555 A1 | 6/2023 |
| WO | WO2023/110556 A1 | 6/2023 |
| WO | WO2023/110594 A1 | 6/2023 |
| WO | WO2023/110607 A1 | 6/2023 |
| WO | WO2023/117721 A1 | 6/2023 |
| WO | WO2023/117821 A1 | 6/2023 |
| WO | WO2023/117822 A1 | 6/2023 |
| WO | WO2023/118080 A1 | 6/2023 |
| WO | WO2023105288 A1 | 6/2023 |
| WO | WO2023/131566 A1 | 7/2023 |
| WO | WO2023/131574 A1 | 7/2023 |
| WO | WO2023/135024 A1 | 7/2023 |
| WO | WO2023/141653 A2 | 7/2023 |
| WO | WO2023/152639 A1 | 8/2023 |
| WO | WO2023/169967 A1 | 9/2023 |
| WO | WO2023/180811 A2 | 9/2023 |
| WO | WO2023/218428 A1 | 11/2023 |
| WO | WO2023/230053 A1 | 11/2023 |
| WO | WO2023/230054 A1 | 11/2023 |
| WO | WO2024/009143 A1 | 1/2024 |
| WO | WO2024/016088 A1 | 1/2024 |
| WO | WO2024/040185 A2 | 2/2024 |
| WO | WO2024/047580 A1 | 3/2024 |
| WO | WO2024/092272 A1 | 5/2024 |
| WO | WO2024/120659 A1 | 6/2024 |
| WO | WO2024/125872 A1 | 6/2024 |
| WO | WO2024/130252 A1 | 6/2024 |
| WO | WO2024/144897 A1 | 7/2024 |
| WO | WO2024/163876 A1 | 8/2024 |
| WO | WO2024/201441 A1 | 10/2024 |
| WO | WO2024/208895 A1 | 10/2024 |
| WO | WO2024/209347 A1 | 10/2024 |
| WO | WO2024/209348 A1 | 10/2024 |
| WO | WO2024/211441 A1 | 10/2024 |
| WO | WO2024/211443 A1 | 10/2024 |
| WO | WO2024/216282 A2 | 10/2024 |
| WO | WO2024/221001 A2 | 10/2024 |
| WO | WO2024/257021 A1 | 12/2024 |
| WO | WO2025/029064 A1 | 2/2025 |
| WO | WO2025/034028 A1 | 2/2025 |
| WO | WO2025/034029 A1 | 2/2025 |
| WO | WO2025/038127 A1 | 2/2025 |
| WO | WO2025/089446 A1 | 5/2025 |
| WO | WO2025/090924 A1 | 5/2025 |
| WO | WO2025129356 A1 | 6/2025 |
| WO | WO2025133076 A1 | 6/2025 |
| WO | WO2025137497 A1 | 6/2025 |
| WO | WO2025/160452 A1 | 7/2025 |
| WO | WO2025141544 A1 | 7/2025 |
| WO | WO2025141545 A1 | 7/2025 |
| WO | WO2025/175101 A1 | 8/2025 |
| WO | WO2025/199655 A1 | 10/2025 |
| WO | WO2025/208076 A1 | 10/2025 |
| WO | WO2025/245181 A1 | 11/2025 |

OTHER PUBLICATIONS

Duryea et al.; U.S. Appl. No. 18/498,979 entitled "Histotripsy systems and methods," filed Oct. 31, 2023.
Shaffer et al., U.S. Appl. No. 18/832,708 entitled "Histotripsy systems and methods," filed Jul. 24, 2024.
Snell et al.; U.S. Appl. No. 18/886,807 entitled "Simulation software and tools for evaluating histotripsy therapy for a given pose and position of a therapy array," filed Sep. 16, 2024.
Schell et al.; U.S. Appl. No. 18/890,580 entitled "Co-registration techniques between computed tomography imaging systems and histotripsy robotic systems," filed Sep. 14, 2024.
Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.
Appel et al.; Stereoscopic highspeed recording of bubble filaments; Ultrasonics Sonochemistry; vol. 11(1); pp. 39-42; Jan. 2004.
Arani et al.; Transurethral prostate magnetic resonance elestography; prospective imaging requirements; Magn. Reson. Med .; 65(2); pp. 340-349; Feb. 2011.
Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.
Atchley et al.; Thresholds for cavitation produced in water by pulsed ultrasound; Ultrasonics.; vol. 26(5); pp. 280-285; Sep. 1988.
Avago Technologies; ACNV2601 High Insulation Voltage 10 MBd Digital Optocoupler. Avago Technologies Data Sheet; pp. 1-11; Jul. 29, 2010.
Avago Technologies; Avago's ACNV2601 optocoupler is an optically coupled logic gate; Data Sheet; 2 pages; Jul. 29, 2010.
Avtech; AVR-8 Data sheet; May 23, 2004; 3 pages; retrieved from the internet (http//www.avtechpulse.com).
Bader et al.; For whom the bubble grows: physical principles of bubble nucleation and dynamics in histotripsy ultrasound therapy; Ultrasound in medicine & biology; 45(5), pp. 1056-1080; May 1, 2019.
Bak; Rapid protytyping or rapid production? 3D printing processes move industry towards the latter; Assembly Automation; 23(4); pp. 340-345; Dec. 1, 2003.
Billson et al.; Rapid prototyping technologies for ultrasonic beam focussing in NDE; IEEE International Ultrasonic Symposium Proceedings; pp. 2472-2474; Oct. 2011.
Bjoerk et al.; Cool/MOS CP—How to make most beneficial use of the generation of super junction technology devices. Infineon Technologies AG. [retrieved Feb. 4, 2014] from the internet (http://www.infineon. com/dgdl/infineon+-+Application+Note+-+PowerMOSFETs+-+600V+CoolMOS%E284%A2+-+CP+Most+beneficial+use+of+superjunction+technologie+devices.pdf?folderId=db3a304412b407950112b408e8c90004&fileId=db3a304412b407950112b40ac9a40688>pp. 1, 4, 14; Feb. 2007.
Bland et al.; Surgical Oncology; McGraw Hill; Chap. 5 (Cavitron Ultrasonic Aspirator); pp. 461-462; Jan. 29, 2001.
Burdin et al.; Implementation of the laser diffraction technique for cavitation bubble investigations; Particle & Particle Systems Characterization; vol. 19; pp. 73-83; May 2002.
Cain et al.; Concentric-ring and sector-vortex phased-array applicators for ultrasound hyperthermia; IEEE Transactions on Microwave Theory and Techniques; 34(5); pp. 542-551; May 1986.
Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.
Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).
Chan et al.; An image-guided high intensity focused ultrasound device for uterine fibroids treatment; Medical Physics, vol. 29, pp. 2611-2620, Nov. 2002.
Clasen et al.; MR-guided radiofrequency ablation of hepatocellular carcinoma: Long-term effectiveness; J Vase Interv Radiol; 22(6); pp. 762-770; Jun. 2011.
Clement et al.; A hemisphere array for non-invasive ultrasound brain therapy and surgery; Physics in Medicine and Biology, vol. 45, p. 3707-3719, Dec. 2000.
Cline et al.; Magnetic resonance-guided thermal surgery; Magnetic Resonance in Medicine; 30(1); pp. 98-106; Jul. 1993.
Curiel et al.; Elastography for the follow-up of high-intensity focused ultrasound prostate cancer treatment: Initial comparison with MRI; Ultrasound Med. Biol; 31(11); pp. 1461-1468; Nov. 2005.
Desilets et al.; The Design of Efficient Broad-Band Piezoelectric Transducers; Sonics and Ultrasonics, IEEE Transactions on, vol. 25, pp. 115-125, May 1978.

(56) References Cited

OTHER PUBLICATIONS

Dovedi et al.; Acquired Resistance to Fractionated Radiotherapy Can Be Overcome by Concurrent PD-LI Blockade; Cancer Research; 74(19); pp. 5458-5468; Oct. 1, 2014.

Emelianov et al.; Triplex ultrasound: Elasticity imaging to age deep venous thrombosis; Ultrasound Med Biol; 28(6); pp. 757-767; Jun. 2002.

Gateau et al.; Transcranial ultrasonic therapy based on time reversal of acoustically induced cavitation bubble signature. IEEE Transactions on Biomedical Engineering: 57(1); pp. 134-144; Sep. 18, 2009.

Giannatsis et al.; Additive fabrication technologies applied to medicine and health care: a review; The International Journal of Advanced Manufacturing Technology; 40(1-2); pp. 116-127; Jan. 2009.

Gudra et al.; Influence of acoustic impedance of multilayer acoustic systems on the transfer function of ultrasonic airborne transducers; Ultrasonics, vol. 40, pp. 457-463, May 2002.

Hall et al.; A Low Cost Compact 512 Channel Therapeutic Ultrasound System For Transcutaneous Ultrasound Surgery; AIP Conference Proceedings, Boston, MA; vol. 829, pp. 445-449, Oct. 27-29, 2005.

Hall et al.; Acoustic Access to the Prostate for Extracorporeal Ultrasound Ablation; Journal of Endourology, vol. 24, pp. 1875-1881, Nov. 2010.

Hall et al.; Histotripsy of the prostate: dose effects in a chronic canine model; Urology; 74(4); pp. 932-937; Oct. 2009 (author manuscript).

Hall et al.; Imaging feedback of tissue liquefaction (histotripsy) in ultrasound surgery; IEEE Ultrasonic Symposium, Sep. 18-21, 2005, pp. 1732-1734.

Haller et al.; Determination of acoustic cavitation probabilities and thresholds using a single focusing transducer to induce and detect acoustic cavitation events: I. Method and terminology; Ultrasound in Medicine & Biology; 44(2); pp. 377-396; Feb. 1, 2018.

Hartmann; Ultrasonic properties of poly(4-methyl pentene-1), Journal of Applied Physics, vol. 51, pp. 310-314, Jan. 1980.

Hobarth et al.; Color flow doppler sonography for extracorporal shock wave lithotripsy; Journal of Urology; 150(6); pp. 1768-1770; Dec. 1, 1993.

Holland et al.; Thresholds for transient cavitation produced by pulsed ultrasound in a controlled nuclei environment; J. Acoust. Soc. Am.; vol. 88(5); pp. 2059-2069; Nov. 1990.

Huber et al.; Influence of shock wave pressure amplitude and pulse repetition frequency on the lifespan, size and number of transient cavities in the field of an electromagnetic lithotripter; Physics in Medicine and Biology; vol. 43(10); pp. 3113-3128; Oct. 1998.

Hynynen et al.; Feasibility of using ultrasound phased arrays for MRI monitored noninvasive surgery; IEEE transactions on ultrasonics, ferroelectrics, and frequency control; 43(6); pp. 1043-1053; Nov. 1996.

Hynynen et al.; Tissue thermometry during ultrasound exposure; European Urology; 23(Suppl 1); pp. 12-16; (the year of publication is sufficiently earlier than the effective U.S. filing date and any foreign priority date so that the particular month of publication is not in issue) 1993.

International Society for Magnetic Resonance in Medicine (ISMRM); No. 105; XP040714022;I Jul. 24, 2020.

Hoogenboom et al.; Mechanical high-intensity focused ultrasound destruction of soft tissue: working mechanisms and physiologic effects; Ultrasound in medicine & biology; 41(6); pp. 1500-1517; Jun. 1, 2015.

Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.

Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.

Kim et al.; Dependence of particle vol. fraction on sound velocity and attenuation of EPDM composites; Ultrasonics, vol. 46, pp. 177-183, Feb. 2007.

Kim et al.; Development of a wearable robotic positioning system for noninvasive transcranial focused ultrasound stimulation. IEEE/ASME Transactions on Mechatronics; 21(5); pp. 2284-2293; Jun. 13, 2016.

Konofagou; Quo vadis elasticity imaging ?; Ultrasonics; 42(1-9); pp. 331-336; Apr. 2004.

Krimholtz et al.; New equivalent circuits for elementary piezoelectric transducers; Electronics Letters, vol. 6, pp. 398-399, Jun. 1970.

Kruse et al.; Tissue characterization using magnetic resonance elastography: Preliminary results; Phys. Med. Biol; 45(6); pp. 1579-1590; Jun. 2000.

Lake et al.; Histotripsy: minimally invasive technology for prostatic tissue ablation in an in vivo canine model; Urology; 72(3); pp. 682-686; Sep. 2008.

Lauterborn et al.; Cavitation bubble dynamics studied by high speed photography and holography: part one; Ultrasonics; vol. 23; pp. 260-268; Nov. 1985.

Lensing et al.; Deep-vein thrombosis; The Lancet, vol. 353, pp. 479-485, Feb. 6, 1999.

Lin et al; Dual-beam histotripsy: a low-frequency pump enabling a high-frequency probe for precise lesion formation; IEEE Trans. Ultrason. Ferroelectr. Control; 61(2); pp. 325-340; Feb. 2014; (Author Manuscript; 29 pages).

Liu et al.; Real-time 2-D temperature imaging using ultrasound; IEEE Trans Biomed Eng; 57(1); pp. 12-16; Jan. 2010 (author manuscript, 16 pgs.).

Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).

Ma et al.; Acoustic focusing and imaging via phononic crystal and acoustic metamaterials; Journal of Applied Physics; 131(1); doi:10.10653/5.0074503; 29 pages; Jan. 5, 2022.

Macoskey; Acoustic methods for histotripsy feedback; (Dissertation); Biomedical Engineering and Science Computing; University of Michigan 2019; 207 pages; retrived from the internet (https://deepblue.lib.umich.edu/handle/2027.42/149988) on Feb. 2022.

Manes et al.; Design of a Simplified Delay System for Ultrasound Phased Array Imaging; Sonics and Ultrasonics, IEEE Transactions on, vol. 30, pp. 350-354, Nov. 1983.

Maréchal et al.; Effect of Radial Displacement of Lens on Response of Focused Ultrasonic Transducer; Japanese Journal of Applied Physics, vol. 46, p. 3077-3085; May 15, 2007.

Maréchal et al.; Lens-focused transducer modeling using an extended KLM model; Ultrasonics, vol. 46, pp. 155-167, May 2007.

Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.

Maxwell et al.; Cavitation clouds created by shock scattering from bubbles during histotripsy; J. Acoust. Soc. Am.; 130(4); pp. 1888-1898; Oct. 2011.

Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).

Maxwell; Noninvasive thrombolysis using histotripsy pulsed ultrasound cavitation therapy; PhD Dissertation. University of Michigan, Ann Arbor, Michigan. Jun. 2012.

Maxwell et al.; In-vivo study of non-invasive thrombolysis by histotripsy in a porcine model; IEEE international Ultrasonics Symposium; IEEE; p. 220-223; Sep. 20, 2009.

Maxwell et al.; The role of compressional pressure in the formation of dense bubble clouds in histotripsy; 2009 IEEE International Ultrasonics Symposium; pp. 81-84; Sep. 20, 2009.

Miller et al.; A review of in vitro bioeffects of inertial ultrasonic cavitation from a mechanistic perspective; Ultrasound in Medicine and Biology; vol. 22; pp. 1131-1154; (the year of publication is sufficiently earlier than the effective U.S. filing date and any foreign priority date so that the particular month of publication is not in issue) 1996.

(56) References Cited

OTHER PUBLICATIONS

Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.

Miller et al.; Real-time elastography-based monitoring of histotripsy tissue fractionation using color doppler; Ultrasonics Symposium (IUS); 2012 IEEE International; 8 pages; Oct. 7-10, 2012.

Nightingale et al.; Analysis of contrast in images generated with transient acoustic radiation force; Ultrasound Med Biol; 32(1); pp. 61-72; Jan. 2006.

Ohl et al.; Bubble dynamics, shock waves and sonoluminescence; Phil. Trans. R. Soc. Lond. A; vol. 357; pp. 269-294; (the year of publication is sufficiently earlier than the effective U.S. filing date and any foreign priority date so that the particular month of publication is not in issue) 1999.

Okada et al.; A case of hepatocellular carcinoma treated by MR-guided focused ultrasound ablation with respiratory gating; Magn Reson Med Sci; 5(3); pp. 167-171; Oct. 2006.

Palmeri et al.; Acoustic radiation force-based elasticity imaging methods; Interface Focus; 1; pp. 553-564; Aug. 2011.

Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.

Parsons et al.; Pulsed cavitational ultrasound therapy for controlled tissue homogenization; Ultrasound in Med. & Biol.; vol. 32(1); pp. 115-129; Jan. 2006.

Pishchalnikov et al.; Cavitation Bubble Cluster Activity in the Breakage of Kidney Stones by Lithotripter Shock Waves; J Endourol .; 17(7): 435-446; Sep. 2003.

Porter et al.; Reduction in left ventricular cavitary attenuation and improvement in posterior myocardial contrast . . . ; J Am Soc Echocardiography; pp. 437-441; Jul.-Aug. 1996.

Qu et al.; Non-thermal histotripsy tumor ablation promotes abscopal immune responses that enhance cancer immunotherapy; Journal for immunotherapy of cancer; 8(1); Jan. 15, 2020.

Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.

Rosenschein et al.; Ultrasound Imaging-Guided Noninvasive Ultrasound Thrombolysis: Preclinical Results; Circulation; vol. 102; pp. 238-245, Jul. 11, 2000.

Rowland et al.; MRI study of hepatic tumours following high intensity focused ultrasound surgery; British Journal of Radiology; 70; pp. 144-153; Feb. 1997.

Roy et al.; A precise technique for the measurement of acoustic cavitation thresholds and some preliminary results; Journal of the Acoustical Society of America; vol. 78(5); pp. 1799-1805; Nov. 1985.

Sapareto et al.; Thermal dose determination in cancer therapy; Int J Radiat Oncol Biol Phys; 10(6); pp. 787-800; Apr. 1984.

Sapozhnikov et al.; Ultrasound-Guided Localized Detection of Cavitation During Lithotripsy in Pig Kidney in Vivo; IEEE Ultrasonics Symposium, vol. 2, pp. 1347-1350; Oct. 7-10, 2001.

Sato et al.; Experimental Investigation of Phased Array Using Tapered Matching Layers. 2002 IEEE Ultrasound Symposium. vol. 2; pp. 1235-1238, Oct. 2002.

Sferruzza et al.; Generation of high power unipolar pulse with a piezocomposite transducer; In 1999 IEEE Ultrasonics Symposium Proceedings; International Symposium (Cat. No. 99CH37027); vol. 2; pp. 1125-1128; Oct. 17, 1999.

Shung; Diagnostic Ultrasound: Imaging and Blood Flow Measurements; Taylor and Francis Group, LLC; Boca Raton, FL; 207 pages; (the year of publication is sufficiently earlier than the effective U.S. filing date and any foreign priority date so that the particular month of publication is not in issue) 2006.

Simonin et al.; Characterization of heterogeneous structure in a polymer object manufactured by stereolithography with low-frequency microechography; Journal of Materials Chemistry; vol. 6, pp. 1595-1599, Sep. 1996.

Sokolov et al.; Use of a dual-pulse lithotripter to generate a localized and intensified cavitation field; Journal of the Acoustical Society of America; vol. 110(3); pp. 1685-1695; Sep. 2001.

Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).

Souchon et al.; Visualisation of HIFU lesions using elastography of the human prostate in vivo: Preliminary results; Ultrasound Med. Biol; 29(7); pp. 1007-1015; Jul. 2003.

Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.

Sukovich et al.; Real-time transcranial histotripsy treatment localization and mapping using acoustic cavitation emission feedback; IEEE transactions on ultrasonics, ferroelectrics, and frequency control; 67(6); pp. 1178-1791; Jan. 17, 2020.

Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011[retrieved on Jan. 28, 2014] from: (http://web.archive.org/web/20110720091822/http://www.histotripsy.umich.edu/index.html>.entiredocument) Jul. 2011.

Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.

Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.

Van Kervel et al.; A calculation scheme for the optimum design of ultrasonic transducers; Ultrasonics, vol. 21, pp. 134-140, May 1983.

Wagner et al.; An X-ray C-arm guided automatic targeting system for histotripsy; IEEE Transactions on Biomedical Engineering; 70(2); pp. 592-602; Aug. 15, 2022.

Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009.

Wikipedia; Medical ultrasound; 15 pages; retrieved from the internet (https://en.wikipedia.org/w/index.php?title=Medical_ultrasound&oldid=515340960) on Jan. 12, 2018.

Wijlemans et al.; Magnetic resonance-guided high-intensity focused ultrasound (MR-HIFU) ablation of liver tumours; Cancer Imaging; 12(2); pp. 387-394; Sep. 28, 2012.

Wu et al.; Mechanism and dynamics of hydrodynamic-acoustic cavitation (HAC); Ultrasonics sonochemistry; vol. 49., pp. 89-96; Dec. 1, 2018.

Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).

Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.

Xu et al.; Controlled ultrasound tissue erosion: the role of dynamic interaction between insonation and microbubble activity; Journal of the Acoustical Society of America; vol. 117(1); pp. 424-435; Jan. 2005.

Xu et al.; Controlled ultrasound tissue erosion; IEEE Transaction on Ultrasonics, Ferroelectrics, and Frequency Control; vol. 51 (6); pp. 726-736; Jun. 2004.

Xu et al.; Effects of acoustic parameters on bubble cloud dynamics in ultrasound tissue erosion (histotripsy); Journal of the Acoustical Society of America; vol. 122(1); pp. 229-236; Jul. 2007.

(56) References Cited

OTHER PUBLICATIONS

Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.

Xu et al.; Investigation of intensity threshold for ultrasound tissue erosion; Ultrasound in Med. & Biol.; vol. 31(12); pp. 1673-1682; Dec. 2005.

Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.

Yan et al.; A review of rapid prototyping technologies and systems; Computer-Aided Design, vol. 28, pp. 307-318, Apr. 1996.

Zhang et al.; A fast tissue stiffness-dependent elastography for HIFU-induced lesions inspection; Ultrasonics; 51(8); pp. 857-869; Dec. 2011.

Zheng et al.; An acoustic backscatter-based method for localization of lesions induced by high-intensity focused ultrasound; Ultrasound Med Biol; 36(4); pp. 610-622; Apr. 2010.

Lu et al.; Transcranial MR-guided histotripsy system; IEEE transactions on ultrasonics, ferroelectrics, and frequency control; 68(9); pp. 2917-2929; Mar. 23, 2021.

Rosnitskiy et al.; Method for designing multielement fully populated random phased arrays for ultrasound surgery applications. IEEE transactions on ultrasonics, ferroelectrics, and frequency control; 65(4); pp. 630-637; Jan. 31, 2018.

Kisting et al.; Imaging for targeting, monitoring, and assessment after histotripsy: a non-invasive, non-thermal therapy for cancer; Blood Vessels; vol. 10; pp. 15-21; Mar. 2023.

Kutlu et al.; A target containing phantom for accuracy assessment of cone?beam CT?guided histotripsy. Journal of Applied Clinical Medical Physics; 25(5); e1432; DOI: 10.1002/acm2.14329; 11 pages; Mar. 18, 2024.

Stocker et al.; Endocavity histotripsy for efficient tissue ablationRtransducer design and characterization. IEEE transactions on ultrasonics, ferroelectrics, and frequency control; 68(9); pp. 2896-2905; Jan. 28, 2021.

Woodacre et al.; A low-cost miniature histotripsy transducer for precision tissue ablation. IEEE transactions on ultrasonics, ferroelectrics, and frequency control; 65(11); pp. 2131-2140; Nov. 1, 2018.

Miller; U.S. Appl. No. 19/103,752 entitled "Histotripsy systems and methods," filed Feb. 13, 2025.

Hall et al. U.S. Appl. No. 19/229,825 entitled "Ultrasound transducer with transmit-receive capability for histotripsy," filed Jun. 5, 2025.

Xu et al.; U.S. Appl. No. 19/006,948 entitled "Histotripsy therapy systems and methods for the treatment of brain tissue," filed Dec. 31, 2024.

Maxwell et al.; U.S. Appl. No. 19/187,641 entitled "Histotripsy for thrombolysis," filed Apr. 23, 2025.

Cannata et al.; U.S. Appl. No. 19/210,971 entitled "Ultrasound therapy transducer for histotripsy system and methods," filed May 16, 2025.

Duryea et al.; U.S. Appl. No. 19/139,227 entitled "Systems and methods for enhancing histotripsy bubble cloud size through pulse shape optimization," filed Jun. 13, 2025.

* cited by examiner x-y view of target tissue volume x-y view of target tissue volume

432

422

Closer to transducer

434

Further from transducer x-z view of target tissue volume

432

422

Closer to transducer

Further from transducer y-z view of target tissue volume

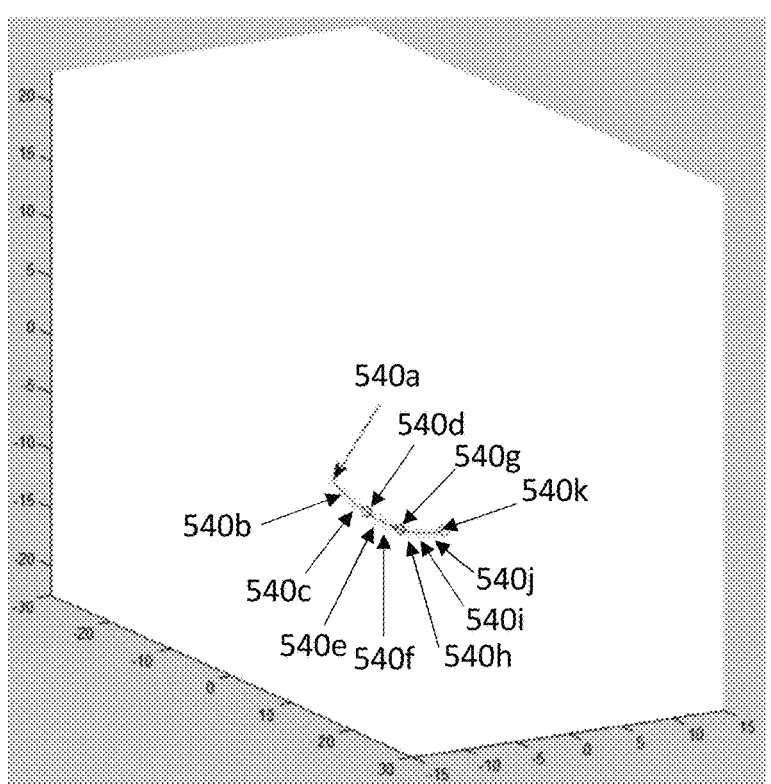

| 540a (start of partial ring) | |
|---|---|
| Therapy on Before Move | False |
| Therapy on After Move | True |
| Dwell Time After Move ($T_{on}$) | $t_{on} > 0$ |
| Cooling Time ($T_{cool}$) | 0 |

| 540k (end of partial ring) | |
|---|---|
| Therapy on Before Move | True |
| Therapy on After Move | True |
| Dwell Time After Move | $t_{on} > 0$ |
| Cooling Time | $t_{cool} > 0$ |

| 540b/c/d/g/i/j (inside partial ring) | |
|---|---|
| Therapy on Before Move | True |
| Therapy on After Move | True |
| Dwell Time After Move | 0 |
| Cooling Time | 0 |

| 540e/f/h (end of treatment segments) | |
|---|---|
| Therapy on Before Move | True |
| Therapy on After Move | True |
| Dwell Time After Move | 0 |
| Cooling Time | $t_{cool} > 0$ |

FIG. 8A

| 842_ (Center of contour 826b) | | 842b' (treatment) | | 842c' (End of segment) | |
| --- | --- | --- | --- | --- | --- |
| Therapy on Before Move | False | Therapy on Before Move | True | Therapy on Before Move | True |
| Therapy on After Move | True | Therapy on After Move | True | Therapy on After Move | True |
| Dwell Time After Move | 0 | Dwell Time After Move | 0 | Dwell Time After Move | 0 |
| Cooling Time | 0 | Cooling Time | 0 | Cooling Time | $t_{cool} > 0$ |

FIG. 8B 842a    842x    842w    842v    842u    842f-842t    842e    842d    842c    842b    842a

Figure 8B:
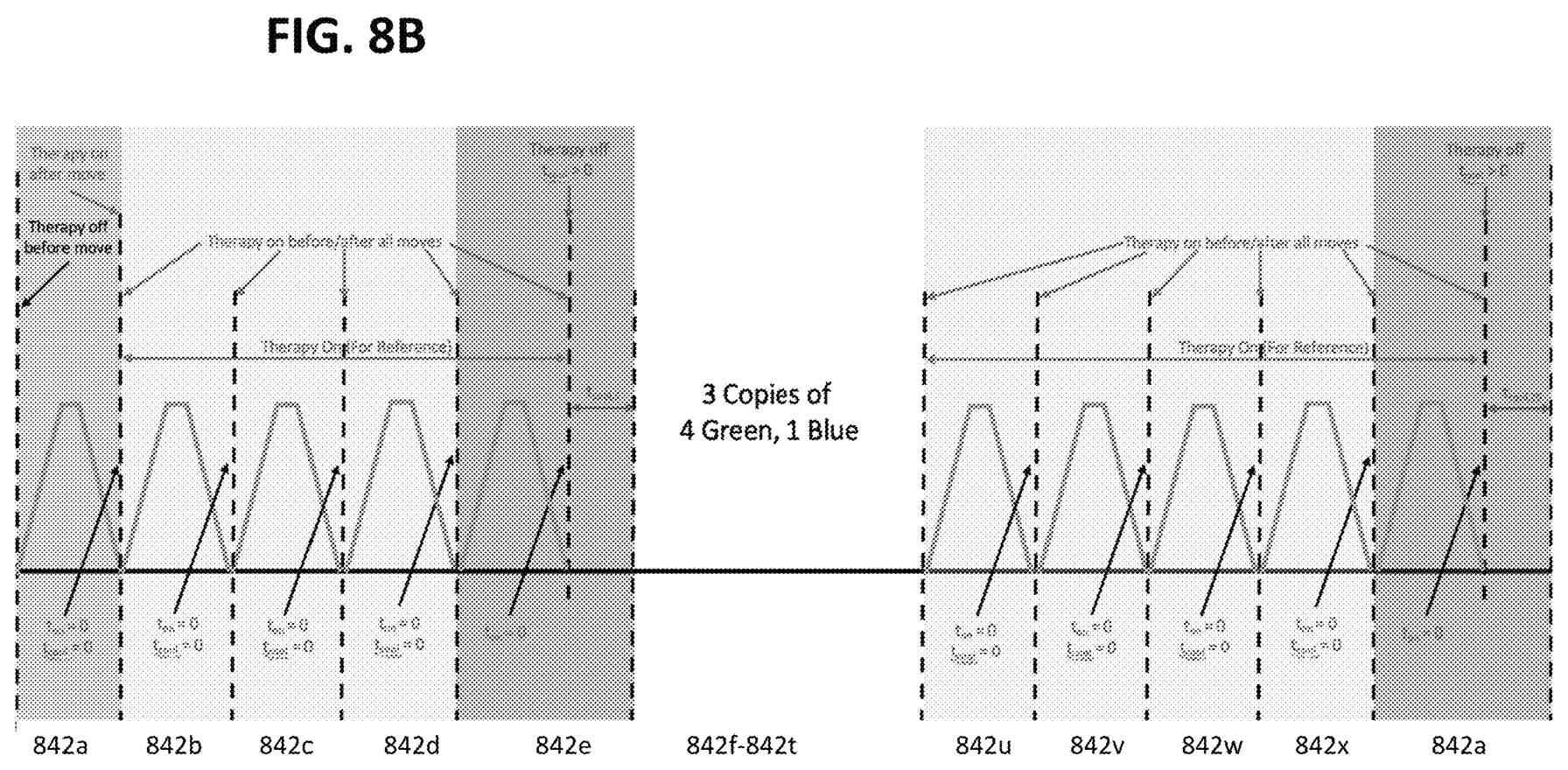

3 Copies of
4 Green, 1 Blue

Therapy Off or Referenced

Therapy on before/after all moves

HIGH INTENSITY THERAPEUTIC ULTRASOUND (HITU) HISTOTRIPSY SYSTEMS, METHODS AND TREATMENT NAVIGATION SOFTWARE

PRIORITY CLAIM

This patent application claims priority to U.S. provisional patent application No. 63/592,327, titled "HISTOTRIPSY SYSTEMS AND METHODS" and filed on Oct. 23, 2023, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure details novel high intensity therapeutic ultrasound (HITU) systems configured to produce acoustic cavitation, methods, devices and procedures for the minimally and non-invasive treatment of healthy, diseased and/or injured tissue. The acoustic cavitation systems and methods described herein, also referred to Histotripsy, may include transducers, drive electronics, positioning robotics, imaging systems, and integrated treatment planning and control software to provide comprehensive treatment and therapy for soft tissues in a patient.

BACKGROUND

Histotripsy, or pulsed ultrasound cavitation therapy, is a technology where extremely short, intense bursts of acoustic energy induce controlled cavitation (microbubble formation) within the focal volume. The vigorous expansion and collapse of these microbubbles mechanically homogenizes cells and tissue structures within the focal volume. This is a very different end result than the coagulative necrosis characteristic of thermal ablation. To operate within a non-thermal, Histotripsy realm; it is necessary to deliver acoustic energy in the form of high amplitude acoustic pulses with low duty cycle.

Compared with conventional focused ultrasound technologies, Histotripsy has important advantages: 1) the destructive process at the focus is mechanical, not thermal; 2) cavitation appears bright on ultrasound imaging thereby confirming correct targeting and localization of treatment; 3) treated tissue generally, but not always, appears darker (more hypoechoic) on ultrasound imaging, so that the operator knows what has been treated; and 4) Histotripsy produces lesions in a controlled and precise manner. It is important to emphasize that unlike thermal ablative technologies such as microwave, radiofrequency, high-intensity focused ultrasound (HIFU) cryo or radiation, Histotripsy relies on the mechanical action of cavitation for tissue destruction and not on heat, cold or ionizing energy.

SUMMARY OF THE DISCLOSURE

A method of preparing a treatment plan for a histotripsy procedure is provided, comprising: identifying a tissue location to be treated; generating a target tissue volume corresponding to the tissue location to be treated, the target tissue volume having an outermost margin contour; dividing a lateral slice (xy axis) of the target tissue volume into a plurality of concentric contours; placing a first plurality of treatment locations along each of the plurality of concentric contours according to predetermined xy spacing parameters; and for each of the first plurality of treatment locations, placing a second plurality of treatment locations in one or more axial directions (z axis) within the margin contour of the target tissue volume according to predetermined z spacing parameters.

In some aspects, the tissue location to be treated comprises a tumor.

In some aspects, the target tissue volume is ellipsoidal/spherical.

In other aspects, the xy spacing parameters are based in part on a bubble cloud size/shape of a histotripsy system.

In some aspects, the z spacing parameters are based in part on a bubble cloud size/shape of a histotripsy system.

In additional aspects, the z spacing parameter are different than the xy spacing parameters.

In some aspects, the z spacing parameter is chosen to account for an elongated ellipsoidal bubble cloud shape that extends further in the Z dimension than in the X and Y dimensions.

In other aspects, the lateral slice comprises a central slice of the target tissue volume.

In additional aspects, the central slice is the largest lateral slice in the target tissue volume.

In one aspect, the concentric contours are ellipsoidal.

In additional aspects, the first and second plurality of treatment locations provide for 90-100% cavitation of the target tissue volume based on a bubble cloud size/shape of a histotripsy system.

In some aspects, the generating, providing, and placing steps are performed by a treatment planning system of a histotripsy system.

In one aspect, the method comprises providing a linear contour central to the plurality of concentric contours.

In another aspect, the method comprises associating a predetermined speed of a therapy transducer with each of the first and second plurality of treatment locations in the treatment plan.

A method of navigating a treatment plan of is also provided, comprising: dividing the second plurality of treatment locations into groups, wherein each group comprises a common Z position within the target tissue volume; initiating histotripsy therapy in a distal-most group of the target tissue volume; delivering histotripsy therapy to each of the treatment locations within the distal-most group with a histotripsy therapy system; navigating the histotripsy therapy system to a group that is proximally adjacent to the distal-most group; delivering histotripsy therapy to each of the treatment locations within the proximally adjacent group with the histotripsy therapy system; and repeating the process for all remaining groups in a distal to proximal direction.

In some aspects, the method includes controlling a robotic system of the histotripsy system to navigate between treatment locations with predetermined acceleration, deceleration, and maximum velocity parameters.

In other aspects, the method includes determining if treatment is on or off before/during/after navigation between treatment locations.

In some aspects, the method comprises adding periods of cooling at selected treatment locations where therapy is turned off.

A histotripsy treatment planning system is also provided, comprising: a robotic positioning system; an ultrasound transducer array disposed on the robotic positioning system, the ultrasound transducer array being configured to deliver ultrasound pulses into a subject; one or more processors operatively coupled to the robotic positioning system and the ultrasound transducer array; and a non-transitory computing device readable medium having instructions stored thereon for generating a treatment plan for ultrasound therapy, wherein the instructions are executable by the one or more processors to cause the ultrasound system to: identify a tissue location to be treated; generate a target tissue volume corresponding to the tissue location to be treated, the target tissue volume having an outermost margin contour; divide a lateral slice (xy axis) of the target tissue volume into a plurality of concentric contours; place a first plurality of treatment locations along each of the plurality of concentric contours according to predetermined xy spacing parameters; and for each of the first plurality of treatment locations, placing a second plurality of treatment locations in one or more axial directions (z axis) within the margin contour of the target tissue volume according to predetermined z spacing parameters.

In some aspects, the tissue location to be treated comprises a tumor.

In other aspects, the target tissue volume is ellipsoidal/spherical.

In some aspects, the xy spacing parameters are based in part on a bubble cloud size/shape of a histotripsy system.

In other aspects, the z spacing parameters are based in part on a bubble cloud size/shape of a histotripsy system.

In some aspects, the z spacing parameter are different than the xy spacing parameters.

In other aspects, the z spacing parameter is chosen to account for an elongated ellipsoidal bubble cloud shape that extends further in the Z dimension than in the X and Y dimensions.

In one aspect, the lateral slice comprises a central slice of the target tissue volume.

In an additional aspect, the central slice is the largest lateral slice in the target tissue volume.

In some aspects, the concentric contours are ellipsoidal.

In another aspect, the first and second plurality of treatment locations provide for 90-100% cavitation of the target tissue volume based on a bubble cloud size/shape of a histotripsy system.

In one aspect, the treatment plan includes a linear contour central to the plurality of concentric contours.

In another aspect, the instructions are executable by the one or more processors to cause the ultrasound system to associate a predetermined speed of a therapy transducer with each of the first and second plurality of treatment locations in the treatment plan.

A method of implementing a digital histotripsy treatment plan is provided, comprising: receiving first movement coordinates from the digital histotripsy treatment plan for robotically moving a therapy transducer to a first treatment location within a subject; robotically moving the therapy transducer to the first treatment location based on the first movement coordinates with a first acceleration value, a first deceleration value, and a first maximum velocity such that a first velocity of the therapy transducer is 0 when a focus of the therapy transducer arrives at the first treatment location; receiving second movement coordinates from the digital histotripsy treatment plan for robotically moving a therapy transducer from the first treatment location to a second treatment location within the subject; and robotically moving the therapy transducer to the second treatment location based on the second movement coordinates with a second acceleration value, a second deceleration value, and a second maximum velocity such that a second velocity of the therapy transducer is 0 when a focus of the therapy transducer arrives at the second treatment location.

In some aspects, the method includes applying histotripsy therapy with the therapy transducer while moving the therapy transducer to the first treatment location.

In another aspect, the method includes applying no histotripsy therapy with the therapy transducer while moving the therapy transducer to the first treatment location.

In some aspects, the method includes applying histotripsy therapy with the therapy transducer while moving the therapy transducer from the first treatment location to the second treatment location.

In other aspects, the method includes applying no histotripsy therapy with the therapy transducer while moving the therapy transducer to the first treatment location.

In some aspects, the method includes receiving a first dwell time to remain at the first treatment location before robotically moving to the second treatment location.

In additional aspects, method includes receiving a first idle time to remain at the first treatment location or second treatment location.

A histotripsy treatment planning system is provided, comprising: a robotic positioning system; an ultrasound transducer array disposed on the robotic positioning system, the ultrasound transducer array being configured to deliver ultrasound pulses into a subject; one or more processors operatively coupled to the robotic positioning system and the ultrasound transducer array; and a non-transitory computing device readable medium having instructions stored thereon for generating a treatment plan for ultrasound therapy, wherein the instructions are executable by the one or more processors to cause the ultrasound system to: receive first movement coordinates from the treatment plan for robotically moving a therapy transducer to a first treatment location within a subject; control the robotic positioning system to move the therapy transducer to the first treatment location based on the first movement coordinates with a first acceleration value, a first deceleration value, and a first maximum velocity such that a first velocity of the therapy transducer is 0 when a focus of the therapy transducer arrives at the first treatment location; receive second movement coordinates from the treatment plan for robotically moving a therapy transducer from the first treatment location to a second treatment location within the subject; and control the robotic positioning system to move the therapy transducer to the second treatment location based on the second movement coordinates with a second acceleration value, a second deceleration value, and a second maximum velocity such that a second velocity of the therapy transducer is 0 when a focus of the therapy transducer arrives at the second treatment location.

In some aspects, the system is configured to control the ultrasound transducer array to apply histotripsy therapy while moving the therapy transducer to the first treatment location.

In some aspects, the system is configured to control the ultrasound transducer array to apply no histotripsy therapy while moving the therapy transducer to the first treatment location.

In other aspects, the system is configured to control the ultrasound transducer array to apply histotripsy therapy while moving the therapy transducer from the first treatment location to the second treatment location.

In some aspects, the system is configured to control the ultrasound transducer array to apply no histotripsy therapy while moving the therapy transducer to the first treatment location.

In some aspects, the system is configured to receive a first dwell time to remain at the first treatment location before robotically moving to the second treatment location.

In other aspects, the system is configured to receive a first idle time to remain at the first treatment location or second treatment location.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 7A-7B illustrate another embodiment of a timing diagram for traversing a digital treatment plan.

FIGS. 8A-8B show another embodiment of a timing diagram for traversing a digital treatment plan.

DETAILED DESCRIPTION

The system, methods and devices of the disclosure may be used for open surgical, minimally invasive surgical (laparoscopic and percutaneous), robotic surgical (integrated into a robotically-enabled medical system), endoscopic or completely transdermal extracorporeal non-invasive acoustic cavitation for the treatment of healthy, diseased and/or injured tissue including but not limited to tissue destruction, cutting, skeletonizing and ablation. Furthermore, due to tissue selective properties, histotripsy may be used to create a cytoskeleton that allows for subsequent tissue regeneration either de novo or through the application of stem cells and other adjuvants. Finally, histotripsy can be used to cause the release of delivered agents such as chemotherapy and immunotherapy by locally causing the release of these agents by the application of acoustic energy to the targets. As will be described below, the acoustic cavitation system may include various sub-systems, including a Cart, Therapy, Integrated Imaging, Robotics, Coupling and Software. The system also may comprise various Other Components, Ancillaries and Accessories, including but not limited to computers, cables and connectors, networking devices, power supplies, displays, drawers/storage, doors, wheels, and various simulation and training tools, etc. All systems, methods and means creating/controlling/delivering histotripsy are considered to be a part of this disclosure, including new related inventions disclosed herein.

Figure 1A:
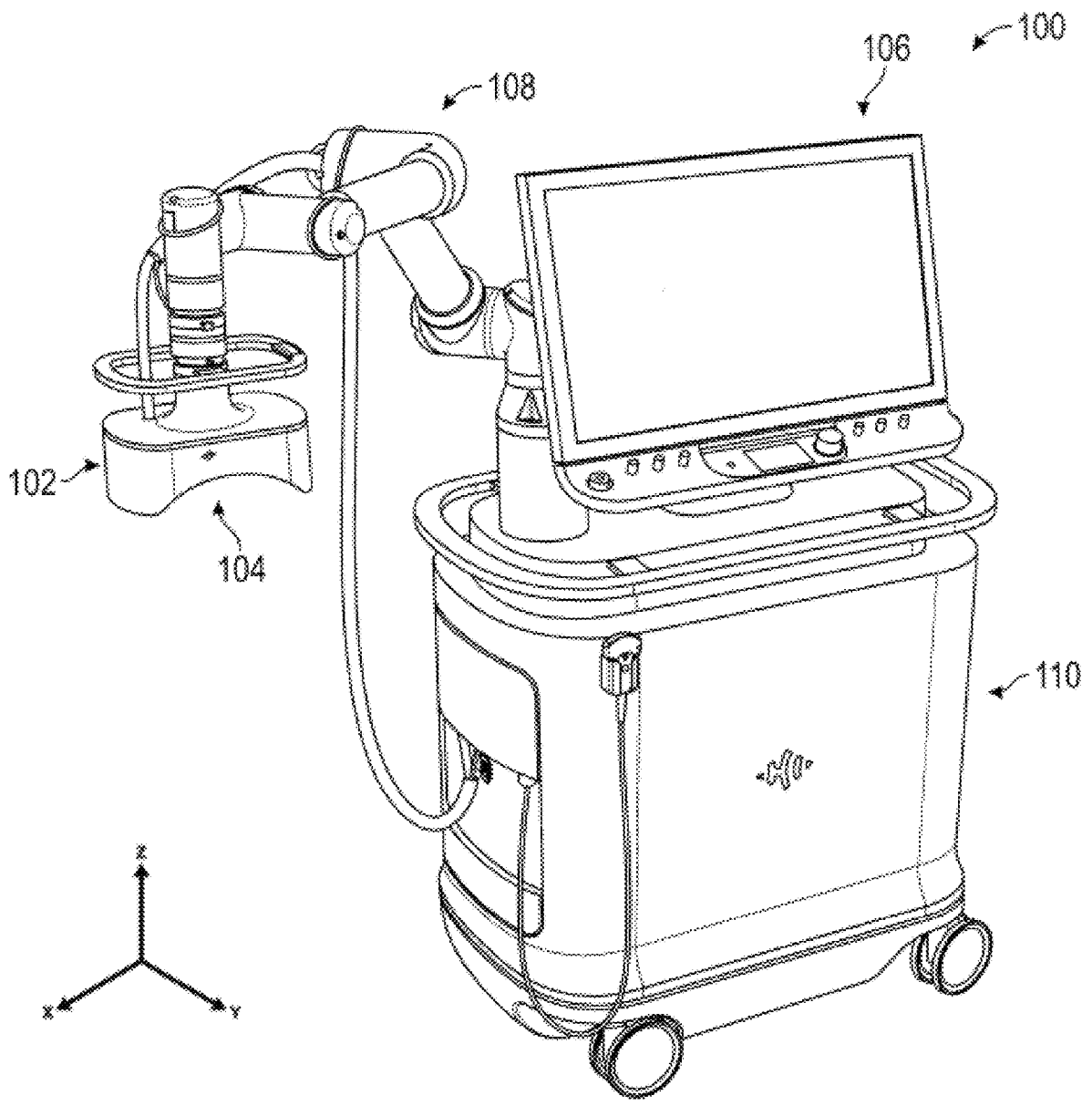
FIGS. 1A-1B illustrate an ultrasound imaging and therapy system.

FIG. 1A generally illustrates histotripsy system 100 according to the present disclosure, comprising a therapy transducer 102, an imaging system 104, a display and control panel 106, a robotic positioning arm 108, and a cart 110. The system can further include an ultrasound coupling interface and a source of coupling medium, not shown.

Figure 1B:
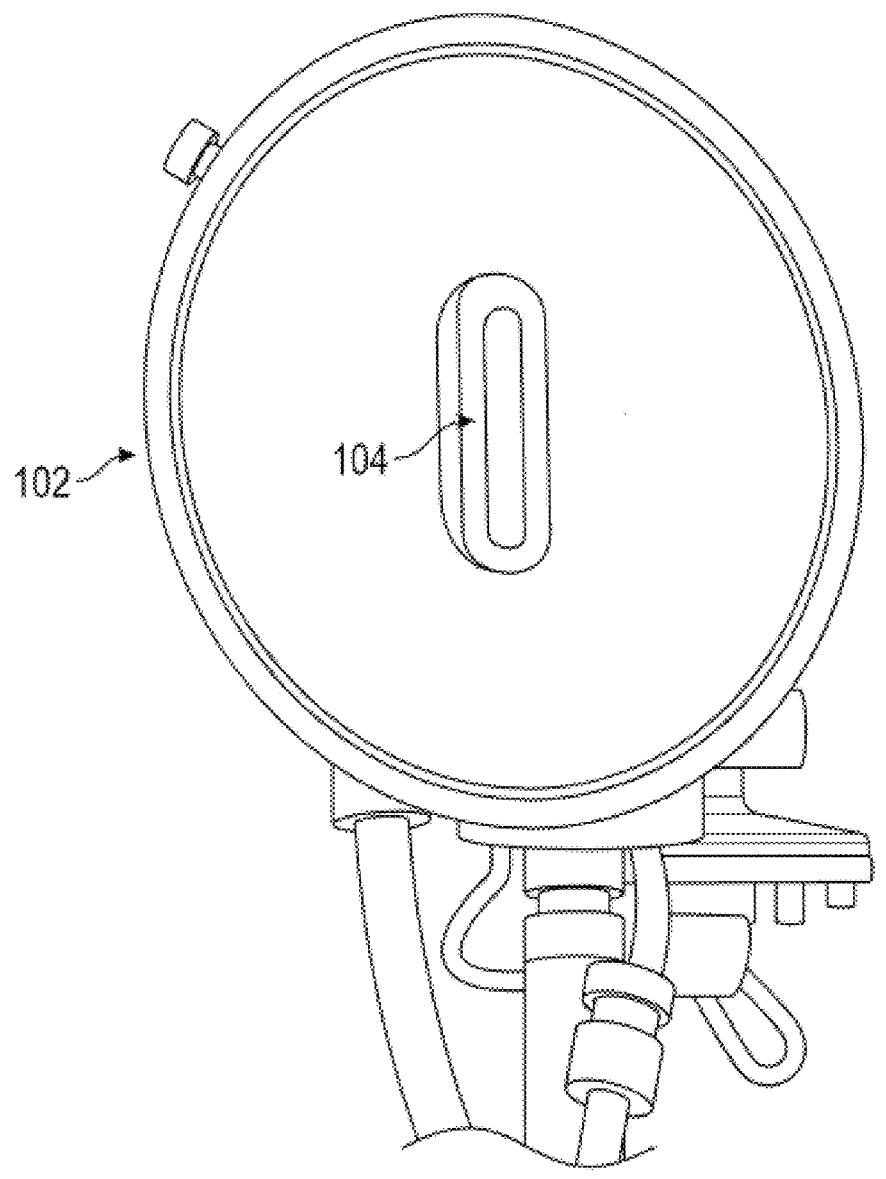

FIG. 1B is a bottom view of the therapy transducer 102 and the imaging system 104. As shown, the imaging system can be positioned in the center of the therapy transducer. However, other embodiments can include the imaging system positioned in other locations within the therapy transducer, or even directly integrated into the therapy transducer. In some embodiments, the imaging system is configured to produce real-time imaging at a focal point of the therapy transducer. The system also allows for multiple imaging transducers to be located within the therapy transducer to provide multiple views of the target tissue simultaneously and to integrate these images into a single 3-D image.

The histotripsy system may comprise one or more of various sub-systems, including a Therapy sub-system that can create, apply, focus and deliver acoustic cavitation/histotripsy through one or more therapy transducers, Integrated Imaging sub-system (or connectivity to) allowing real-time visualization of the treatment site and histotripsy effect through-out the procedure, a Robotics positioning sub-system to mechanically and/or electronically steer the therapy transducer, further enabled to connect/support or interact with a Coupling sub-system to allow acoustic coupling between the therapy transducer and the patient, and Software to communicate, control and interface with the system and computer-based control systems (and other external systems) and various Other Components, Ancillaries and Accessories, including one or more user interfaces and displays, and related guided work-flows, all working in part or together. The system may further comprise various fluidics and fluid management components, including but not limited to, pumps, valve and flow controls, temperature and degassing controls, and irrigation and aspiration capabilities, as well as providing and storing fluids. It may also contain various power supplies and protectors.

As described above, the histotripsy system may include integrated imaging. However, in other embodiments, the histotripsy system can be configured to interface with separate imaging systems, such as C-arm, fluoroscope, cone beam CT, MRI, etc., to provide real-time imaging during histotripsy therapy. In some embodiments, the histotripsy system can be sized and configured to fit within a C-arm, fluoroscope, cone beam CT, MRI, etc.

Cart

The Cart 110 may be generally configured in a variety of ways and form factors based on the specific uses and procedures. In some cases, systems may comprise multiple Carts, configured with similar or different arrangements. In some embodiments, the cart may be configured and arranged to be used in a radiology environment and in some cases in concert with imaging (e.g., CT, cone beam CT and/or MRI scanning). In other embodiments, it may be arranged for use in an operating room and a sterile environment for open surgical or laparoscopic surgical and endoscopic application, or in a robotically enabled operating room, and used alone, or as part of a surgical robotics procedure wherein a surgical robot conducts specific tasks before, during or after use of the system and delivery of acoustic cavitation/histotripsy. As such and depending on the procedure environment based on the aforementioned embodiments, the cart may be positioned to provide sufficient work-space and access to various anatomical locations on the patient (e.g., torso, abdomen, flank, head and neck, etc.), as well as providing work-space for other systems (e.g., anesthesia cart, laparoscopic tower, surgical robot, endoscope tower, etc.).

The Cart may also work with a patient surface (e.g., table or bed) to allow the patient to be presented and repositioned in a plethora of positions, angles and orientations, including allowing changes to such to be made pre, peri and post-procedurally. It may further comprise the ability to interface and communicate with one or more external imaging or image data management and communication systems, not limited to ultrasound, CT, fluoroscopy, cone beam CT, PET, PET/CT, MRI, optical, ultrasound, and image fusion and or image flow, of one or more modalities, to support the procedures and/or environments of use, including physical/mechanical interoperability (e.g., compatible within cone beam CT work-space for collecting imaging data pre, peri and/or post histotripsy) and to provide access to and display of patient medical data including but not limited to laboratory and historical medical record data.

In some embodiments one or more Carts may be configured to work together. As an example, one Cart may comprise a bedside mobile Cart equipped with one or more Robotic arms enabled with a Therapy transducer, and Therapy generator/amplifier, etc., while a companion cart working in concert and at a distance of the patient may comprise Integrated Imaging and a console/display for controlling the Robotic and Therapy facets, analogous to a surgical robot and master/slave configurations.

In some embodiments, the system may comprise a plurality of Carts, all slave to one master Cart, equipped to conduct acoustic cavitation procedures. In some arrangements and cases, one Cart configuration may allow for storage of specific sub-systems at a distance reducing operating room clutter, while another in concert Cart may comprise essentially bedside sub-systems and componentry (e.g., delivery system and therapy).

One can envision a plethora of permutations and configurations of Cart design, and these examples are in no way limiting the scope of the disclosure.

Histotripsy

Histotripsy comprises short, high amplitude, focused ultrasound pulses to generate a dense, energetic, "bubble cloud", capable of the targeted fractionation and destruction of tissue. Histotripsy is capable of creating controlled tissue erosion when directed at a tissue interface, including tissue/fluid interfaces, as well as well-demarcated tissue fractionation and destruction, at sub-cellular levels, when it is targeted at bulk tissue. Unlike other forms of ablation, including thermal and radiation-based modalities, histotripsy does not rely on heat cold or ionizing (high) energy to treat tissue. Instead, histotripsy uses acoustic cavitation generated at the focus to mechanically effect tissue structure, and in some cases liquefy, suspend, solubilize and/or destruct tissue into sub-cellular components.

Histotripsy can be applied in various forms, including: 1) Intrinsic-Threshold Histotripsy: Delivers pulses typically with a 1-2 cycles of high amplitude negative/tensile phase pressure exceeding the intrinsic threshold to generate cavitation in the medium (e.g., ~24-28 MPa for water-based soft tissue), 2) Shock-Scattering Histotripsy: Delivers typically pulses 1-20 cycles in duration. The shockwave (positive/compressive phase) scattered from an initial individual microbubble generated forms inverted shockwave, which constructively interferes with the incoming negative/tensile phase to form high amplitude negative/rarefactional phase exceeding the intrinsic threshold. In this way, a cluster of cavitation microbubbles is generated. The amplitude of the tensile phases of the pulses is sufficient to cause bubble nuclei in the medium to undergo inertial cavitation within the focal zone throughout the duration of the pulse. These nuclei scatter the incident shockwaves, which invert and constructively interfere with the incident wave to exceed the threshold for intrinsic nucleation, and 3) Boiling Histotripsy: Employs pulses roughly 1-20 ms in duration. Absorption of the shocked pulse rapidly heats the medium, thereby reducing the threshold for intrinsic nuclei. Once this intrinsic threshold coincides with the peak negative pressure of the incident wave, boiling bubbles form at the focus.

The large pressure generated at the focus causes a cloud of acoustic cavitation bubbles to form above certain thresholds, which creates localized stress and strain in the tissue and mechanical breakdown without significant heat deposition. At pressure levels where cavitation is not generated, minimal effect is observed on the tissue at the focus. This cavitation effect is observed only at pressure levels significantly greater than those which define the inertial cavitation threshold in water for similar pulse durations, on the order of 10 to 30 MPa peak negative pressure.

Histotripsy may be performed in multiple ways and under different parameters. It may be performed totally non-invasively by acoustically coupling a focused ultrasound transducer over the skin of a patient and transmitting acoustic pulses transcutaneously through overlying (and intervening) tissue to the focal zone (treatment zone and site). The application of histotripsy is not limited to a transdermal approach but can be applied through any means that allow contact of the transducer with tissue including open surgical laparoscopic surgical, percutaneous and robotically mediated surgical procedures. It may be further targeted, planned, directed and observed under direct visualization, via ultrasound imaging, given the bubble clouds generated by histotripsy may be visible as highly dynamic, echogenic regions on, for example, B Mode ultrasound images, allowing continuous visualization through its use (and related procedures). Likewise, the treated and fractionated tissue shows a dynamic change in echogenicity (typically a reduction), which can be used to evaluate, plan, observe and monitor treatment.

Generally, in histotripsy treatments, ultrasound pulses with 1 or more acoustic cycles are applied, and the bubble cloud formation relies on the pressure release scattering of the positive shock fronts (sometimes exceeding 100 MPa, P+) from initially initiated, sparsely distributed bubbles (or a single bubble). This is referred to as the "shock scattering mechanism".

Figure 3:
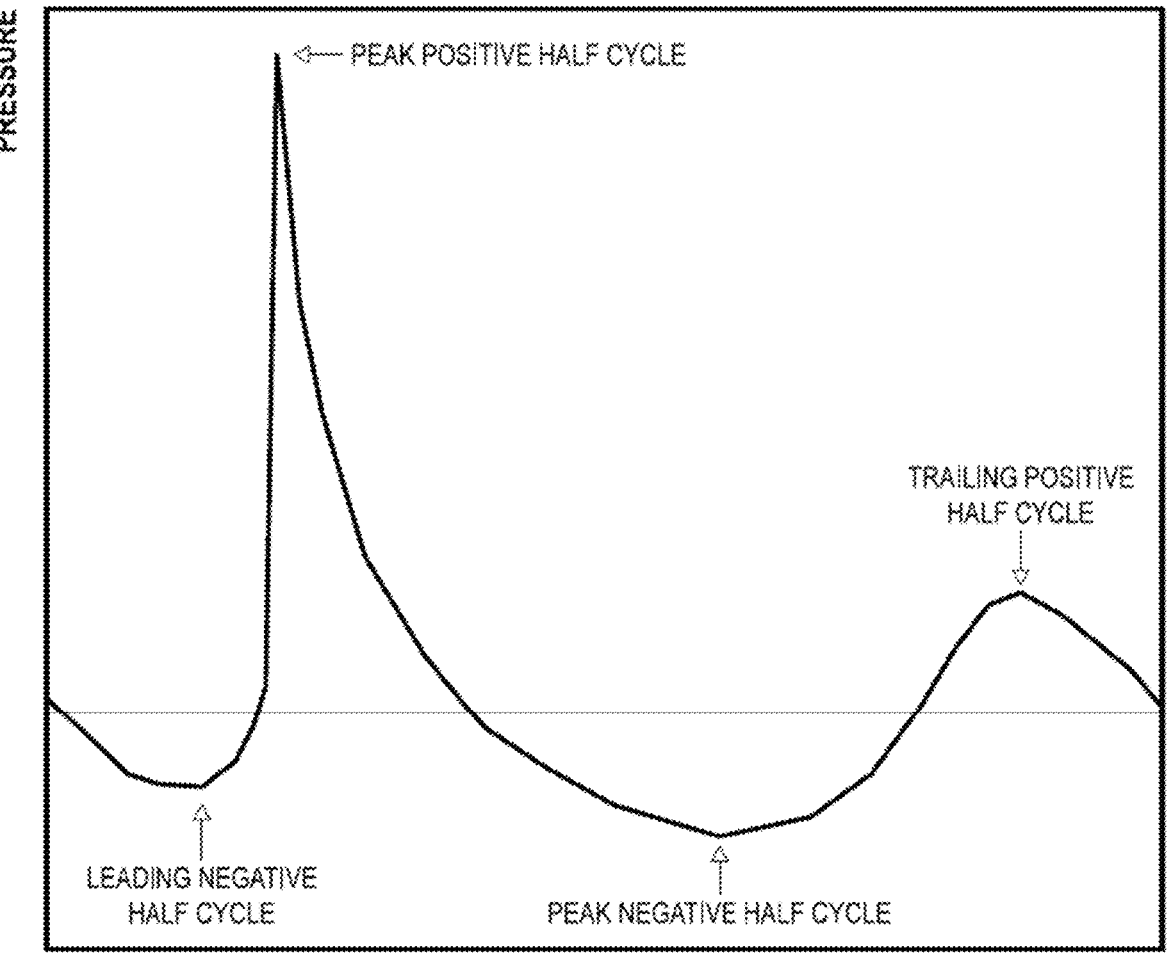
FIG. 3 is one example of an ultrasound pulse for generating histotripsy via a shock scattering mechanism.

FIG. 3 illustrates an ultrasound pulse that can be used for shock scattering histotripsy. As shown the ultrasound pulse can include a leading negative half-cycle, a peak positive half-cycle, a peak negative half-cycle, and a trailing positive half-cycle (with the pulse traveling from right to left on the page). As shown, the trailing peak positive half-cycle has a lower amplitude than the peak positive half-cycle. This mechanism depends on one (or a few sparsely distributed) bubble(s) initiated with the initial negative half cycle(s) of the pulse at the focus of the transducer. A cloud of microbubbles then forms due to the pressure release back-scattering of the high peak positive shock fronts from these sparsely initiated bubbles. These back-scattered high-amplitude rarefactional waves exceed the intrinsic threshold thus producing a localized dense bubble cloud. Each of the following acoustic cycles then induces further cavitation by the backscattering from the bubble cloud surface if the amplitude of those cycles is sufficient, which grows towards the transducer. As a result, an elongated dense bubble cloud growing along the acoustic axis opposite the ultrasound propagation direction is observed with the shock scattering mechanism. This shock scattering process makes the bubble cloud generation not only dependent on the peak negative half-cycle pressure, but also the number of acoustic cycles and the amplitudes of the positive shocks. Without at least one intense shock front developed by nonlinear propagation, no dense bubble clouds are generated when the peak negative half-cycles are below the intrinsic threshold.

When the amplitude(s) of positive half-cycle(s) of each pulse are limited, shock scattering can be minimized, and the generation of a dense bubble cloud depends on the negative half-cycle(s) of the applied ultrasound pulses exceeding an "intrinsic threshold" of the medium. This is referred to as the "intrinsic threshold mechanism".

This threshold can be in the range of 26-30 MPa for soft tissues with high water content, such as tissues in the human body. In some embodiments, using this intrinsic threshold mechanism, the spatial extent of the lesion may be well-defined and more predictable. With peak negative pressures (P−) not significantly higher than this threshold, sub-wavelength reproducible lesions as small as half of the −6 dB beam width of a transducer may be generated.

With high-frequency Histotripsy pulses, the size of the smallest reproducible lesion becomes smaller, which is beneficial in applications that require precise lesion generation. However, high-frequency pulses are more susceptible to attenuation and aberration, rendering problematical treatments at a larger penetration depth (e.g., ablation deep in the body) or through a highly aberrative medium (e.g., transcranial procedures, or procedures in which the pulses are transmitted through bone(s)). Histotripsy may further also be applied as a low-frequency "pump" pulse (typically <2 cycles and having a frequency between 100 kHz and 1 MHz) can be applied together with a high-frequency "probe" pulse (typically <2 cycles and having a frequency greater than 2 MHz, or ranging between 2 MHz and 10 MHz) wherein the peak negative pressures of the low and high-frequency pulses constructively interfere to exceed the intrinsic threshold in the target tissue or medium. The low-frequency pulse, which is more resistant to attenuation and aberration, can raise the peak negative pressure P− level for a region of interest (ROI), while the high-frequency pulse, which provides more precision, can pin-point a targeted location within the ROI and raise the peak negative pressure P− above the intrinsic threshold. This approach may be referred to as "dual frequency", "dual beam histotripsy" or "parametric histotripsy."

Additional systems, methods and parameters to deliver optimized histotripsy, using shock scattering, intrinsic threshold, and various parameters enabling frequency compounding and bubble manipulation, are herein included as part of the system and methods disclosed herein, including additional means of controlling said histotripsy effect as pertains to steering and positioning the focus, and concurrently managing tissue effects (e.g., prefocal thermal collateral damage) at the treatment site or within intervening tissue. Further, it is disclosed that the various systems and methods, which may include a plurality of parameters, such as but not limited to, frequency, operating frequency, center frequency, pulse repetition frequency, pulses, bursts, number of pulses, cycles, length of pulses, amplitude of pulses, pulse period, delays, burst repetition frequency, sets of the former, loops of multiple sets, loops of multiple and/or different sets, sets of loops, and various combinations or permutations of, etc., are included as a part of this disclosure, including future envisioned embodiments of such.

Therapy Components

The Therapy sub-system may work with other sub-systems to create, optimize, deliver, visualize, monitor and control acoustic cavitation, also referred to herein and in following as "histotripsy", and its derivatives of, including boiling histotripsy and other thermal high frequency ultrasound approaches. It is noted that the disclosed inventions may also further benefit other acoustic therapies that do not comprise a cavitation, mechanical or histotripsy component. The therapy sub-system can include, among other features, an ultrasound therapy transducer and a pulse generator system configured to deliver ultrasound pulses into tissue.

In order to create and deliver histotripsy and derivatives of histotripsy, the therapy sub-system may also comprise components, including but not limited to, one or more function generators, amplifiers, therapy transducers and power supplies.

The therapy transducer can comprise a single element or multiple elements configured to be excited with high amplitude electric pulses (>1000V or any other voltage that can cause harm to living organisms). The amplitude necessary to drive the therapy transducers for Histotripsy vary depending on the design of the transducer and the materials used (e.g., solid or polymer/piezoelectric composite including ceramic or single crystal) and the transducer center frequency which is directly proportional to the thickness of the piezo-electric material. Transducers therefore operating at a high frequency require lower voltage to produce a given surface pressure than is required by low frequency therapy transducers. In some embodiments, the transducer elements are formed using a piezoelectric-polymer composite material or a solid piezoelectric material. Further, the piezoelectric material can be of polycrystalline/ceramic or single crystalline formulation. In some embodiments the transducer elements can be formed using silicon using MEMs technology, including CMUT and PMUT designs.

In some embodiments, the function generator may comprise a field programmable gate array (FPGA) or other suitable function generator. The FPGA may be configured with parameters disclosed previously herein, including but not limited to frequency, pulse repetition frequency, bursts, burst numbers, where bursts may comprise pulses, numbers of pulses, length of pulses, pulse period, delays, burst repetition frequency or period, where sets of bursts may comprise a parameter set, where loop sets may comprise various parameter sets, with or without delays, or varied delays, where multiple loop sets may be repeated and/or new loop sets introduced, of varied time delay and independently controlled, and of various combinations and permutations of such, overall and throughout.

In some embodiments, the generator or amplifier may be configured to be a universal single-cycle or multi-cycle pulse generator, and to support driving via Class D or inductive driving, as well as across all envisioned clinical applications, use environments, also discussed in part later in this disclosure. In other embodiments, the class D or inductive current driver may be configured to comprise transformer and/or auto-transformer driving circuits to further provide step up/down components, and in some cases, to preferably allow a step up in the amplitude. They may also comprise specific protective features, to further support the system, and provide capability to protect other parts of the system (e.g., therapy transducer and/or amplifier circuit components) and/or the user, from various hazards, including but not limited to, electrical safety hazards, which may potentially lead to use environment, system and therapy system, and user harms, damage or issues.

Disclosed generators may allow and support the ability of the system to select, vary and control various parameters (through enabled software tools), including, but not limited to those previously disclosed, as well as the ability to start/stop therapy, set and read voltage level, pulse and/or burst repetition frequency, number of cycles, duty ratio, channel enabled and delay, etc., modulate pulse amplitude on a fast time-scale independent of a high voltage supply, and/or other service, diagnostic or treatment features.

In some embodiments, the Therapy sub-system and/or components of, such as the amplifier, may comprise further integrated computer processing capability and may be networked, connected, accessed, and/or be removable/portable, modular, and/or exchangeable between systems, and/or driven/commanded from/by other systems, or in various combinations. Other systems may include other acoustic cavitation/histotripsy, HIFU, HITU, radiation therapy, radiofrequency, microwave, and cryoablation systems, navigation and localization systems, open surgical, laparoscopic, single incision/single port, endoscopic and non-invasive surgical robots, laparoscopic or surgical towers comprising other energy-based or vision systems, surgical system racks or booms, imaging carts, etc.

In some embodiments, one or more amplifiers may comprise a Class D amplifier and related drive circuitry including matching network components. Depending on the transducer element electric impedance and choice of the matching network components (e.g., an LC circuit made of an inductor L1 in series and the capacitor C1 in parallel), the combined impedance can be aggressively set low in order to have high amplitude electric waveform necessary to drive the transducer element. The maximum amplitude that Class D amplifiers is dependent on the circuit components used, including the driving MOSFET/IGBT transistors, matching network components or inductor, and transformer or autotransformer, and of which may be typically in the low kV (e.g., 1-3 kV) range.

Therapy transducer element(s) are excited with an electrical waveform with an amplitude (voltage) to produce a pressure output sufficient for Histotripsy therapy. The excitation electric field can be defined as the necessary waveform voltage per thickness of the piezoelectric element. For example, because a piezoelectric element operating at 1 MHz transducer is half the thickness of an equivalent 500 kHz element, it will require half the voltage to achieve the same electric field and surface pressure.

The Therapy sub-system may also comprise therapy transducers of various designs and working parameters, supporting use in various procedures (and procedure settings). Systems may be configured with one or more therapy transducers, that may be further interchangeable, and work with various aspects of the system in similar or different ways (e.g., may interface to a robotic arm using a common interface and exchange feature, or conversely, may adapt to work differently with application specific imaging probes, where different imaging probes may interface and integrate with a therapy transducer in specifically different ways).

Therapy transducers may be configured of various parameters that may include size, shape (e.g., rectangular or round; anatomically curved housings, etc.), geometry, focal length, number of elements, size of elements, distribution of elements (e.g., number of rings, size of rings for annular patterned transducers), frequency, enabling electronic beam steering, etc. Transducers may be composed of various materials (e.g., piezoelectric, silicon, etc.), form factors and types (e.g., machined elements, chip-based, etc.) and/or by various methods of fabrication of.

Transducers may be designed and optimized for clinical applications (e.g., abdominal tumors, peripheral vascular disease, fat ablation, etc.) and desired outcomes (e.g., acoustic cavitation/histotripsy without thermal injury to intervening tissue), and affording a breadth of working ranges, including relatively shallow and superficial targets (e.g., thyroid or breast nodules), versus, deeper or harder to reach targets, such as central liver or brain tumors. They may be configured to enable acoustic cavitation/histotripsy under various parameters and sets of, as enabled by the aforementioned system components (e.g., function generator and amplifier, etc.), including but not limited to frequency, pulse repetition rate, pulses, number of pulses, pulse length, pulse period, delays, repetitions, sync delays, sync period, sync pulses, sync pulse delays, various loop sets, others, and permutations of. The transducer may also be designed to allow for the activation of a drug payload either deposited in tissue through various means including injection, placement or delivery in micelle or nanostructures.

Integrated Imaging

The disclosed system may comprise various imaging modalities to allow users to visualize, monitor and collect/use feedback of the patient's anatomy, related regions of interest and treatment/procedure sites, as well as surrounding and intervening tissues to assess, plan and conduct procedures, and adjust treatment parameters as needed. Imaging modalities may comprise various ultrasound, x-ray, CT, MRI, PET, fluoroscopy, optical, contrast or agent enhanced versions, and/or various combinations of. It is further disclosed that various image processing and characterization technologies may also be utilized to afford enhanced visualization and user decision making. These may be selected or commanded manually by the user or in an automated fashion by the system. The system may be configured to allow side by side, toggling, overlays, 3D reconstruction, segmentation, registration, multi-modal image fusion, image flow, and/or any methodology affording the user to identify, define and inform various aspects of using imaging during the procedure, as displayed in the various system user interfaces and displays. Examples may include locating, displaying and characterizing regions of interest, organ systems, potential treatment sites within, with on and/or surrounding organs or tissues, identifying critical structures such as ducts, vessels, nerves, ureters, fissures, capsules, tumors, tissue trauma/injury/disease, other organs, connective tissues, etc., and/or in context to one another, of one or more (e.g., tumor draining lymphatics or vasculature; or tumor proximity to organ capsule or underlying other organ), as unlimited examples.

Systems may be configured to include onboard integrated imaging hardware, software, sensors, probes and wetware, and/or may be configured to communicate and interface with external imaging and image processing systems. The aforementioned components may be also integrated into the system's Therapy sub-system components wherein probes, imaging arrays, or the like, and electrically, mechanically or electromechanically integrated into therapy transducers. This may afford, in part, the ability to have geometrically aligned imaging and therapy, with the therapy directly within the field of view, and in some cases in line, with imaging. In some embodiments, this integration may comprise a fixed orientation of the imaging capability (e.g., imaging probe) in context to the therapy transducer. In other embodiments, the imaging solution may be able to move or adjust its position, including modifying angle, extension (e.g., distance from therapy transducer or patient), rotation (e.g., imaging plane in example of an ultrasound probe) and/or other parameters, including moving/adjusting dynamically while actively imaging. The imaging component or probe may be encoded so its orientation and position relative to another aspect of the system, such as the therapy transducer, and/or robotically-enabled positioning component may be determined.

In one embodiment, the system may comprise onboard ultrasound, further configured to allow users to visualize, monitor and receive feedback for procedure sites through the system displays and software, including allowing ultrasound imaging and characterization (and various forms of), ultrasound guided planning and ultrasound guided treatment, all in real-time. The system may be configured to allow users to manually, semi-automated or in fully automated means image the patient (e.g., by hand or using a robotically-enabled imager).

In some embodiments, imaging feedback and monitoring can include monitoring changes in: backscatter from bubble clouds; speckle reduction in backscatter; backscatter speckle statistics; mechanical properties of tissue (i.e., elastography); tissue perfusion (i.e., ultrasound contrast); shear wave propagation; acoustic emissions, electrical impedance tomography, and/or various combinations of, including as displayed or integrated with other forms of imaging (e.g., CT or MRI).

In some embodiments, imaging including feedback and monitoring from backscatter from bubble clouds, may be used as a method to determine immediately if the histotripsy process has been initiated, is being properly maintained, or even if it has been extinguished. For example, this method enables continuously monitored in real time drug delivery, tissue erosion, and the like. The method also can provide feedback permitting the histotripsy process to be initiated at a higher intensity and maintained at a much lower intensity. For example, backscatter feedback can be monitored by any transducer or ultrasonic imager. By measuring feedback for the therapy transducer, an accessory transducer can send out interrogation pulses or be configured to passively detect cavitation. Moreover, the nature of the feedback received can be used to adjust acoustic parameters (and associated system parameters) to optimize the drug delivery and/or tissue erosion process.

In some embodiments, imaging including feedback and monitoring from backscatter, and speckle reduction, may be configured in the system.

For systems comprising feedback and monitoring via backscattering, and as means of background, as tissue is progressively mechanically subdivided, in other words homogenized, disrupted, or eroded tissue, this process results in changes in the size and distribution of acoustic scatter. At some point in the process, the scattering particle size and density is reduced to levels where little ultrasound is scattered, or the amount scattered is reduced significantly. This results in a significant reduction in speckle, which is the coherent constructive and destructive interference patterns of light and dark spots seen on images when coherent sources of illumination are used; in this case, ultrasound. After some treatment time, the speckle reduction results in a dark area in the therapy volume. Since the amount of speckle reduction is related to the amount of tissue subdivision, it can be related to the size of the remaining tissue fragments. When this size is reduced to sub-cellular levels, no cells are assumed to have survived. So, treatment can proceed until a desired speckle reduction level has been reached. Speckle is easily seen and evaluated on standard ultrasound imaging systems. Specialized transducers and systems, including those disclosed herein, may also be used to evaluate the backscatter changes.

Further, systems comprising feedback and monitoring via speckle, and as means of background, an image may persist from frame to frame and change very little as long as the scatter distribution does not change and there is no movement of the imaged object. However, long before the scatters are reduced enough in size to cause speckle reduction, they may be changed sufficiently to be detected by signal processing and other means. This family of techniques can operate as detectors of speckle statistics changes. For example, the size and position of one or more speckles in an image will begin to decorrelate before observable speckle reduction occurs. Speckle decorrelation, after appropriate motion compensation, can be a sensitive measure of the mechanical disruption of the tissues, and thus a measure of therapeutic efficacy. This feedback and monitoring technique may permit early observation of changes resulting from the acoustic cavitation/histotripsy process and can identify changes in tissue before substantial or complete tissue effect (e.g., erosion occurs). In one embodiment, this method may be used to monitor the acoustic cavitation/histotripsy process for enhanced drug delivery where treatment sites/tissue is temporally disrupted, and tissue damage/erosion is not desired. In other embodiments, this may comprise speckle decorrelation by movement of scatters in an increasingly fluidized therapy volume. For example, in the case where partial or complete tissue erosion is desired.

For systems comprising feedback and monitoring via elastography, and as means of background, as treatment sites/tissue are further subdivided per an acoustic cavitation/histotripsy effect (homogenized, disrupted, or eroded), its mechanical properties change from a soft but interconnected solid to a viscous fluid or paste with few long-range interactions. These changes in mechanical properties can be measured by various imaging modalities including MRI and ultrasound imaging systems. For example, an ultrasound pulse can be used to produce a force (i.e., a radiation force) on a localized volume of tissue. The tissue response (displacements, strains, and velocities) can change significantly during histotripsy treatment allowing the state of tissue disruption to be determined by imaging or other quantitative means.

Systems may also comprise feedback and monitoring via shear wave propagation changes. As means of background, the subdivision of tissues makes the tissue more fluid and less solid and fluid systems generally do not propagate shear waves. Thus, the extent of tissue fluidization provides opportunities for feedback and monitoring of the histotripsy process. For example, ultrasound and MRI imaging systems can be used to observe the propagation of shear waves. The extinction of such waves in a treated volume is used as a measure of tissue destruction or disruption. In one system embodiment, the system and supporting sub-systems may be used to generate and measure the interacting shear waves. For example, two adjacent ultrasound foci might perturb tissue by pushing it in certain ways. If adjacent foci are in a fluid, no shear waves propagate to interact with each other. If the tissue is not fluidized, the interaction would be detected with external means, for example, by a difference frequency only detected when two shear waves interact nonlinearly, with their disappearance correlated to tissue damage. As such, the system may be configured to use this modality to enhance feedback and monitoring of the acoustic cavitation/histotripsy procedure.

For systems comprising feedback and monitoring via acoustic emission, and as means of background, as a tissue volume is subdivided, its effect on acoustic cavitation/histotripsy (e.g., the bubble cloud here) is changed. For example, bubbles may grow larger and have a different lifetime and collapse changing characteristics in intact versus fluidized tissue. Bubbles may also move and interact after tissue is subdivided producing larger bubbles or cooperative interaction among bubbles, all of which can result in changes in acoustic emission. These emissions can be heard during treatment and they change during treatment. Analysis of these changes, and their correlation to therapeutic efficacy, enables monitoring of the progress of therapy, and may be configured as a feature of the system.

For systems comprising feedback and monitoring via electrical impedance tomography, and as means of background, an impedance map of a therapy site can be produced based upon the spatial electrical characteristics throughout the therapy site. Imaging of the conductivity or permittivity of the therapy site of a patient can be inferred from taking skin surface electrical measurements. Conducting electrodes are attached to a patient's skin and small alternating currents are applied to some or all of the electrodes. One or more known currents are injected into the surface and the voltage is measured at a number of points using the electrodes. The process can be repeated for different configurations of applied current. The resolution of the resultant image can be adjusted by changing the number of electrodes employed. A measure of the electrical properties of the therapy site within the skin surface can be obtained from the impedance map, and changes in and location of the acoustic cavitation/histotripsy (e.g., bubble cloud, specifically) and histotripsy process can be monitored using this as configured in the system and supporting sub-systems.

The user may be allowed to further select, annotate, mark, highlight, and/or contour, various regions of interest or treatment sites, and defined treatment targets (on the image (s)), of which may be used to command and direct the system where to image, test and/or treat, through the system software and user interfaces and displays. In some arrangements, the user may use a manual ultrasound probe (e.g., diagnostic hand-held probe) to conduct the procedure. In another arrangement, the system may use a robot and/or electromechanical positioning system to conduct the procedure, as directed and/or automated by the system, or conversely, the system can enable combinations of manual and automated uses.

The system may further include the ability to conduct image registration, including imaging and image data set registration to allow navigation and localization of the system to the patient, including the treatment site (e.g., tumor, critical structure, bony anatomy, anatomy and identifying features of, etc.). In one embodiment, the system allows the user to image and identify a region of interest, for example the liver, using integrated ultrasound, and to select and mark a tumor (or surrogate marker of) comprised within the liver through/displayed in the system software, and wherein said system registers the image data to a coordinate system defined by the system, that further allows the system's Therapy and Robotics sub-systems to deliver synchronized acoustic cavitation/histotripsy to said marked tumor. The system may comprise the ability to register various image sets, including those previously disclosed, to one another, as well as to afford navigation and localization (e.g., of a therapy transducer to a CT or MRI/ultrasound fusion image with the therapy transducer and Robotics sub-system tracking to said image).

The system may also comprise the ability to work in a variety of interventional, endoscopic and surgical environments, including alone and with other systems (surgical/laparoscopic towers, vision systems, endoscope systems and towers, ultrasound enabled endoscopic ultrasound (flexible and rigid), percutaneous/endoscopic/laparoscopic and minimally invasive navigation systems (e.g., optical, electromagnetic, shape-sensing, ultrasound-enabled, etc.), of also which may work with, or comprise various optical imaging capabilities (e.g., fiber and or digital). The disclosed system may be configured to work with these systems, in some embodiments working alongside them in concert, or in other embodiments where all or some of the system may be integrated into the above systems/platforms (e.g., acoustic cavitation/histotripsy-enabled endoscope system or laparoscopic surgical robot). In many of these environments, a therapy transducer may be utilized at or around the time of use, for example, of an optically guided endoscope/bronchoscope, or as another example, at the time a laparoscopic robot (e.g., Intuitive Da Vinci* Xi system) is viewing/manipulating a tissue/treatment site. Further, these embodiments and examples may include where said other systems/platforms are used to deliver (locally) fluid to enable the creation of a man-made acoustic window, where on under normal circumstances may not exist (e.g., fluidizing a segment or lobe of the lung in preparation for acoustic cavitation/histotripsy via non-invasive transthoracic treatment (e.g., transducer externally placed on/around patient). Systems disclosed herein may also comprise all or some of their sub-system hardware packaged within the other system cart/console/systems described here (e.g., acoustic cavitation/histotripsy system and/or sub-systems integrated and operated from said navigation or laparoscopic system).

The system may also be configured, through various aforementioned parameters and other parameters, to display real-time visualization of a bubble cloud in a spatial-temporal manner, including the resulting tissue effect peri/post-treatment from tissue/bubble cloud interaction, wherein the system can dynamically image and visualize, and display, the bubble cloud, and any changes to it (e.g., decreasing or increasing echogenicity), which may include intensity, shape, size, location, morphology, persistence, etc. These features may allow users to continuously track and follow the treatment in real-time in one integrated procedure and interface/system, and confirm treatment safety and efficacy on the fly (versus other interventional or surgical modalities, which either require multiple procedures to achieve the same, or where the treatment effect is not visible in real-time (e.g., radiation therapy), or where it is not possible to achieve such (e.g., real-time visualization of local tissue during thermal ablation), and/or where the other procedure further require invasive approaches (e.g., incisions or punctures) and iterative imaging in a scanner between procedure steps (e.g., CT or MRI scanning). The above disclosed systems, sub-systems, components, modalities, features and work-flows/methods of use may be implemented in an unlimited fashion through enabling hardware, software, user interfaces and use environments, and future improvements, enhancements and inventions in this area are considered as included in the scope of this disclosure, as well as any of the resulting data and means of using said data for analytics, artificial intelligence or digital health applications and systems.

Robotics

They system may comprise various Robotic sub-systems and components, including but not limited to, one or more robotic arms and controllers, which may further work with other sub-systems or components of the system to deliver and monitor acoustic cavitation/histotripsy. As previously discussed herein, robotic arms and control systems may be integrated into one or more Cart configurations.

For example, one system embodiment may comprise a Cart with an integrated robotic arm and control system, and Therapy, Integrated Imaging and Software, where the robotic arm and other listed sub-systems are controlled by the user through the form factor of a single bedside Cart.

In other embodiments, the Robotic sub-system may be configured in one or more separate Carts, that may be a driven in a master/slave configuration from a separate master or Cart, wherein the robotically-enabled Cart is positioned bed/patient-side, and the Master is at a distance from said Cart.

Disclosed robotic arms may be comprised of a plurality of joints, segments, and degrees of freedom and may also include various integrated sensor types and encoders, implemented for various use and safety features. Sensing technologies and data may comprise, as an example, vision, potentiometers, position/localization, kinematics, force, torque, speed, acceleration, dynamic loading, and/or others. In some cases, sensors may be used for users to direct robot commands (e.g., hand gesture the robot into a preferred set up position, or to dock home). Additional details on robotic arms can be found in US Patent Pub. No. 2013/0255426 to Kassow et al. which is disclosed herein by reference in its entirety.

The robotic arm receives control signals and commands from the robotic control system, which may be housed in a Cart. The system may be configured to provide various functionalities, including but not limited to, position, tracking, patterns, triggering, and events/actions.

Position may be configured to comprise fixed positions, pallet positions, time-controlled positions, distance-controlled positions, variable-time controlled positions, variable-distance controlled positions.

Tracking may be configured to comprise time-controlled tracking and/or distance-controlled tracking.

The patterns of movement may be configured to comprise intermediate positions or waypoints, as well as sequence of positions, through a defined path in space.

Triggers may be configured to comprise distance measuring means, time, and/or various sensor means including those disclosed herein, and not limited to, visual/imaging-based, force, torque, localization, energy/power feedback and/or others.

Events/actions may be configured to comprise various examples, including proximity-based (approaching/departing a target object), activation or de-activation of various end-effectors (e.g., therapy transducers), starting/stopping/pausing sequences of said events, triggering or switching between triggers of events/actions, initiating patterns of movement and changing/toggling between patterns of movement, and/or time-based and temporal over the defined work and time-space.

In one embodiment, the system comprises a three degree of freedom robotic positioning system, enabled to allow the user (through the software of the system and related user interfaces), to micro-position a therapy transducer through X, Y, and Z coordinate system, and where gross macro-positioning of the transducer (e.g., aligning the transducer on the patient's body) is completed manually. In some embodiments, the robot may comprise 6 degrees of freedom including X, Y, Z, and pitch, roll and yaw. In other embodiments, the Robotic sub-system may comprise further degrees of freedom, that allow the robot arm supporting base to be positioned along a linear axis running parallel to the general direction of the patient surface, and/or the supporting base height to be adjusted up or down, allowing the position of the robotic arm to be modified relative to the patient, patient surface, Cart, Coupling sub-system, additional robots/robotic arms and/or additional surgical systems, including but not limited to, surgical towers, imaging systems, endoscopic/laparoscopic systems, and/or other.

One or more robotic arms may also comprise various features to assist in maneuvering and modifying the arm position, manually or semi-manually, and of which said features may interface on or between the therapy transducer and the most distal joint of the robotic arm. In some embodiments, the feature is configured to comprise a handle allowing maneuvering and manual control with one or more hands. The handle may also be configured to include user input and electronic control features of the robotic arm, to command various drive capabilities or modes, to actuate the robot to assist in gross or fine positioning of the arm (e.g., activating or deactivating free drive mode). The work-flow for the initial positioning of the robotic arm and therapy head can be configured to allow either first positioning the therapy transducer/head in the coupling solution, with the therapy transducer directly interfaced to the arm, or in a different work-flow, allowing the user to set up the coupling solution first, and enabling the robot arm to be interfaced to the therapy transducer/coupling solution as a later/terminal set up step.

In some embodiments, the robotic arm may comprise a robotic arm on a laparoscopic, single port, endoscopic, hybrid or combination of, and/or other robot, wherein said robot of the system may be a slave to a master that controls said arm, as well as potentially a plurality of other arms, equipped to concurrently execute other tasks (vision, imaging, grasping, cutting, ligating, sealing, closing, stapling, ablating, suturing, marking, etc.), including actuating one or more laparoscopic arms (and instruments) and various histotripsy system components. For example, a laparoscopic robot may be utilized to prepare the surgical site, including manipulating organ position to provide more ideal acoustic access and further stabilizing said organ in some cases to minimize respiratory motion. In conjunction and parallel to this, a second robotic arm may be used to deliver non-invasive acoustic cavitation through a body cavity, as observed under real-time imaging from the therapy transducer (e.g., ultrasound) and with concurrent visualization via a laparoscopic camera. In other related aspects, a similar approach may be utilized with a combination of an endoscopic and non-invasive approach, and further, with a combination of an endoscopic, laparoscopic and non-invasive approach.

Software

The system may comprise various software applications, features and components which allow the user to interact, control and use the system for a plethora of clinical applications. The Software may communicate and work with one or more of the sub-systems, including but not limited to Therapy, Integrated Imaging, Robotics and Other Components, Ancillaries and Accessories of the system.

Overall, in no specific order of importance, the software may provide features and support to initialize and set up the system, service the system, communicate and import/export/store data, modify/manipulate/configure/control/command various settings and parameters by the user, mitigate safety and use-related risks, plan procedures, provide support to various configurations of transducers, robotic arms and drive systems, function generators and amplifier circuits/slaves, test and treatment ultrasound sequences, transducer steering and positioning (electromechanical and electronic beam steering, etc.), treatment patterns, support for imaging and imaging probes, manual and electromechanical/robotically-enabling movement of, imaging support for measuring/characterizing various dimensions within or around procedure and treatment sites (e.g., depth from one anatomical location to another, etc., pre-treatment assessments and protocols for measuring/characterizing in situ treatment site properties and conditions (e.g., acoustic cavitation/histotripsy thresholds and heterogeneity of), targeting and target alignment, calibration, marking/annotating, localizing/navigating, registering, guiding, providing and guiding through work-flows, procedure steps, executing treatment plans and protocols autonomously, autonomously and while under direct observation and viewing with real-time imaging as displayed through the software, including various views and viewports for viewing, communication tools (video, audio, sharing, etc.), troubleshooting, providing directions, warnings, alerts, and/or allowing communication through various networking devices and protocols. It is further envisioned that the software user interfaces and supporting displays may comprise various buttons, commands, icons, graphics, text, etc., that allow the user to interact with the system in a user-friendly and effective manner, and these may be presented in an unlimited number of permutations, layouts and designs, and displayed in similar or different manners or feature sets for systems that may comprise more than one display (e.g., touch screen monitor and touch pad), and/or may network to one or more external displays or systems (e.g., another robot, navigation system, system tower, console, monitor, touch display, mobile device, tablet, etc.).

The software, as a part of a representative system, including one or more computer processors, may support the various aforementioned function generators (e.g., FPGA), amplifiers, power supplies and therapy transducers. The software may be configured to allow users to select, determine and monitor various parameters and settings for acoustic cavitation/histotripsy, and upon observing/receiving feedback on performance and conditions, may allow the user to stop/start/modify said parameters and settings.

The software may be configured to allow users to select from a list or menu of multiple transducers and support the auto-detection of said transducers upon connection to the system (and verification of the appropriate sequence and parameter settings based on selected application). In other embodiments, the software may update the targeting and amplifier settings (e.g., channels) based on the specific transducer selection. The software may also provide transducer recommendations based on pre-treatment and planning inputs. Conversely, the software may provide error messages or warnings to the user if said therapy transducer, amplifier and/or function generator selections or parameters are erroneous, yield a fault or failure. This may further comprise reporting the details and location of such.

In addition to above, the software may be configured to allow users to select treatment sequences and protocols from a list or menu, and to store selected and/or previous selected sequences and protocols as associated with specific clinical uses or patient profiles. Related profiles may comprise any associated patient, procedure, clinical and/or engineering data, and maybe used to inform, modify and/or guide current or future treatments or procedures/interventions, whether as decision support or an active part of a procedure itself (e.g., using serial data sets to build and guide new treatments).

As a part of planning or during the treatment, the software (and in working with other components of the system) may allow the user to evaluate and test acoustic cavitation/histotripsy thresholds at various locations in a user-selected region of interest or defined treatment area/volume, to determine the minimum cavitation thresholds throughout said region or area/volume, to ensure treatment parameters are optimized to achieve, maintain and dynamically control acoustic cavitation/histotripsy. In one embodiment, the system allows a user to manually evaluate and test threshold parameters at various points. Said points may include those at defined boundary, interior to the boundary and center locations/positions, of the selected region of interest and treatment area/volume, and where resulting threshold measurements may be reported/displayed to the user, as well as utilized to update therapy parameters before treatment. In another embodiment, the system may be configured to allow automated threshold measurements and updates, as enabled by the aforementioned Robotics sub-system, wherein the user may direct the robot, or the robot may be commanded to execute the measurements autonomously.

Software may also be configured, by working with computer processors and one or more function generators, amplifiers and therapy transducers, to allow various permutations of delivering and positioning optimized acoustic cavitation/histotripsy in and through a selected area/volume. This may include, but not limited to, systems configured with a fixed/natural focus arrangement using purely electromechanical positioning configuration(s), electronic beam steering (with or without electromechanical positioning), electronic beam steering to a new selected fixed focus with further electromechanical positioning, axial (Z axis) electronic beam steering with lateral (X and Y) electromechanical positioning, high speed axial electronic beam steering with lateral electromechanical positioning, high speed beam steering in 3D space, various combinations of including with dynamically varying one or more acoustic cavitation/histotripsy parameters based on the aforementioned ability to update treatment parameters based on threshold measurements (e.g., dynamically adjusting amplitude across the treatment area/volume).

Other Components, Ancillaries and Accessories

The system may comprise various other components, ancillaries and accessories, including but not limited to computers, computer processors, power supplies including high voltage power supplies, controllers, cables, connectors, networking devices, software applications for security, communication, integration into information systems including hospital information systems, cellular communication devices and modems, handheld wired or wireless controllers, goggles or glasses for advanced visualization, augmented or virtual reality applications, cameras, sensors, tablets, smart devices, phones, internet of things enabling capabilities, specialized use "apps" or user training materials and applications (software or paper based), virtual proctors or trainers and/or other enabling features, devices, systems or applications, and/or methods of using the above.

System Variations and Methods/Applications

In addition to performing a breadth of procedures, the system may allow additional benefits, such as enhanced planning, imaging and guidance to assist the user. In one embodiment, the system may allow a user to create a patient, target and application specific treatment plan, wherein the system may be configured to optimize treatment parameters based on feedback to the system during planning, and where planning may further comprise the ability to run various test protocols to gather specific inputs to the system and plan.

Feedback may include various energy, power, location, position, tissue and/or other parameters.

The system, and the above feedback, may also be further configured and used to autonomously (and robotically) execute the delivery of the optimized treatment plan and protocol, as visualized under real-time imaging during the procedure, allowing the user to directly observe the local treatment tissue effect, as it progresses through treatment, and start/stop/modify treatment at their discretion. Both test and treatment protocols may be updated over the course of the procedure at the direction of the user, or in some embodiments, based on logic embedded within the system.

It is also recognized that many of these benefits may further improve other forms of acoustic therapy, including thermal ablation with high intensity focused ultrasound (HIFU), high intensity therapeutic ultrasound (HITU) including boiling histotripsy (thermal cavitation), and are considered as part of this disclosure. The disclosure also considers the application of histotripsy as a means to activate previously delivered in active drug payloads whose activity is inert due to protection in a micelle, nanostructure or similar protective structure or through molecular arrangement that allows activation only when struck with acoustic energy.

In another aspect, the Therapy sub-system, comprising in part, one or more amplifiers, transducers and power supplies, may be configured to allow multiple acoustic cavitation and histotripsy driving capabilities, affording specific benefits based on application, method and/or patient specific use. These benefits may include, but are not limited to, the ability to better optimize and control treatment parameters, which may allow delivery of more energy, with more desirable thermal profiles, increased treatment speed and reduced procedure times, enable electronic beam steering and/or other features.

This disclosure also includes novel systems and concepts as related to systems and sub-systems comprising new and "universal" amplifiers, which may allow multiple driving approaches (e.g., single and multi-cycle pulsing). In some embodiments, this may include various novel features to further protect the system and user, in terms of electrical safety or other hazards (e.g., damage to transducer and/or amplifier circuitry).

In another aspect, the system, and Therapy sub-system, may include a plethora of therapy transducers, where said therapy transducers are configured for specific applications and uses and may accommodate treating over a wide range of working parameters (target size, depth, location, etc.) and may comprise a wide range of working specifications (detailed below). Transducers may further adapt, interface and connect to a robotically-enabled system, as well as the Coupling sub-system, allowing the transducer to be positioned within, or along with, an acoustic coupling device allowing, in many embodiments, concurrent imaging and histotripsy treatments through an acceptable acoustic window. The therapy transducer may also comprise an integrated imaging probe or localization sensors, capable of displaying and determining transducer position within the treatment site and affording a direct field of view (or representation of) the treatment site, and as the acoustic cavitation/histotripsy tissue effect and bubble cloud may or may not change in appearance and intensity, throughout the treatment, and as a function of its location within said treatment (e.g., tumor, healthy tissue surrounding, critical structures, adipose tissue, etc.).

The systems, methods and use of the system disclosed herein, may be beneficial to overcoming significant unmet needs in the areas of soft tissue ablation, oncology, immuno-oncology, advanced image guided procedures, surgical procedures including but not limited to open, laparoscopic, single incision, natural orifice, endoscopic, non-invasive, various combination of, various interventional spaces for catheter-based procedures of the vascular, cardiovascular pulmonary and/or neurocranial-related spaces, cosmetics/aesthetics, metabolic (e.g., type 2 diabetes), plastic and reconstructive, ocular and ophthalmology, orthopedic, gynecology and men's health, and other systems, devices and methods of treating diseased, injured, undesired, or healthy tissues, organs or cells.

Systems and methods are also provided for improving treatment patterns within tissue that can reduce treatment time, improve efficacy, and reduce the amount of energy and prefocal tissue heating delivered to patients.

Use Environments

The disclosed system, methods of use, and use of the system, may be conducted in a plethora of environments and settings, with or without various support systems such as anesthesia, including but not limited to, procedure suites, operating rooms, hybrid rooms, in and out-patient settings, ambulatory settings, imaging centers, radiology, radiation therapy, oncology, surgical and/or any medical center, as well as physician offices, mobile healthcare centers or systems, automobiles and related vehicles (e.g., van), aero and marine transportation vehicles such as planes and ships, and/or any structure capable of providing temporary procedure support (e.g., tent). In some cases, systems and/or sub-systems disclosed herein may also be provided as integrated features into other environments, for example, the direct integration of the histotripsy Therapy sub-system into a MRI scanner or patient surface/bed, wherein at a minimum the therapy generator and transducer are integral to such, and in other cases wherein the histotripsy configuration further includes a robotic positioning system, which also may be integral to a scanner or bed centered design.

Coupling

Systems may comprise a variety of Coupling sub-system embodiments, of which are enabled and configured to allow acoustic coupling to the patient to afford effective acoustic access for ultrasound visualization and acoustic cavitation/histotripsy (e.g., provide acoustic window and medium between the transducer(s) and patient, and support of). These may include different form factors of such, including open and enclosed device solutions, and some arrangements which may be configured to allow dynamic control over the acoustic medium (e.g., temperature, dissolved gas content, level of particulate filtration, sterility, volume, composition, etc.). Such dynamic control components may be directly integrated to the system (within the Cart), or may be in temporary/intermittent or continuous communication with the system, but externally situated in a separate device and/or cart.

The Coupling sub-system typically comprises, at a minimum, coupling medium (e.g., degassed water or water solutions), a reservoir/container to contain said coupling medium, and a support structure (including interfaces to other surfaces or devices). In most embodiments, the coupling medium is water, and wherein the water may be conditioned before or during the procedure (e.g., chilled, degassed, filtered, etc.). Various conditioning parameters may be employed based on the configuration of the system and its intended use/application.

The reservoir or medium container may be formed and shaped to various sizes and shapes, and to adapt/conform to the patient, allow the therapy transducer to engage/access and work within the acoustic medium, per defined and required working space (minimum volume of medium to allow the therapy transducer to be positioned and/or move through one or more treatment positions or patterns, and at various standoffs or depths from the patient, etc.), and wherein said reservoir or medium container may also mechanically support the load, and distribution of the load, through the use of a mechanical and/or electromechanical support structure. As a representative example, this may include a support frame. The container may be of various shapes, sizes, curvatures, and dimensions, and may be comprised of a variety of materials compositions (single, multiple, composites, etc.), of which may vary throughout. In some embodiments, it may comprise features such as films, drapes, membranes, bellows, etc. that may be insertable and removable, and/or fabricated within, of which may be used to conform to the patient and assist in confining/containing the medium within the container. It may further contain various sensors (e.g., volume/fill level), drains (e.g., inlet/outlet), lighting (e.g., LEDs), markings (e.g., fill lines, set up orientations, etc.), text (e.g., labeling), etc.

In one embodiment, the reservoir or medium container contains a sealable frame, of which a membrane and/or film may be positioned within, to afford a conformable means of contacting the reservoir (later comprising the treatment head/therapy transducer) as an interface to the patient, that further provides a barrier to the medium (e.g., water) between the patient and therapy transducer). In other embodiments, the membrane and/or film may comprise an opening, the patient contacting edge of which affords a fluid/mechanical seal to the patient, but in contrast allows medium communication directly with the patient (e.g., direct degassed water interface with patient). The superstructure of the reservoir or medium container in both these examples may further afford the proximal portion of the structure (e.g., top) to be open or enclosed (e.g., to prevent spillage or afford additional features).

Disclosed membranes may be comprised of various elastomers, viscoelastic polymers, thermoplastics, thermoplastic elastomers, thermoset polymers, silicones, urethanes, rigid/flexible co-polymers, block co-polymers, random block co-polymers, etc. Materials may be hydrophilic, hydrophobic, surface modified, coated, extracted, etc., and may also contain various additives to enhance performance, appearance or stability. In some embodiments, the thermoplastic elastomer may be styrene-ethylene-butylene-styrene (SEBS), or other like strong and flexible elastomers. The membrane form factor can be flat or pre-shaped prior to use. In other embodiments, the membrane could be inelastic (i.e., a convex shape) and pressed against the patient's skin to acoustically couple the transducer to the tissue. Systems and methods are further disclosed to control the level of contaminants (e.g., particulates, etc.) on the membrane to maintain the proper level of ultrasound coupling. Too many particulates or contaminants can cause scattering of the ultrasound waves. This can be achieved with removable films or coatings on the outer surfaces of the membrane to protect against contamination.

Said materials may be formed into useful membranes through molding, casting, spraying, ultrasonic spraying, extruding, and/or any other processing methodology that produces useful embodiments. They may be single use or reposable/reusable. They may be provided non-sterile, aseptically cleaned or sterile, where sterilization may comprise any known method, including but not limited to ethylene oxide, gamma, e-beam, autoclaving, steam, peroxide, plasma, chemical, etc. Membranes can be further configured with an outer molded or over molded frame to provide mechanical stability to the membrane during handling including assembly, set up and take down of the coupling sub-system. Various parameters of the membrane can be optimized for this method of use, including thickness, thickness profile, density, formulation (e.g., polymer molecular weight and copolymer ratios, additives, plasticizers, etc.), including optimizing specifically to maximize acoustic transmission properties, including minimizing impact to cavitation initiation threshold values, and/or ultrasound imaging artifacts, including but not limited to membrane reflections, as representative examples.

Open reservoirs or medium containers may comprise various methods of filling, including using pre-prepared medium or water, that may be delivered into the containers, in some cases to a defined specification of water (level of temperature, gas saturation, etc.), or they may comprise additional features integral to the design that allow filling and draining (e.g., ports, valves, hoses, tubing, fittings, bags, pumps, etc.). These features may be further configured into or to interface to other devices, including for example, a fluidics system. In some cases, the fluidics system may be an in-house medium preparation system in a hospital or care setting room, or conversely, a mobile cart-based system which can prepare and transport medium to and from the cart to the medium container, etc.

Enclosed iterations of the reservoir or medium container may comprise various features for sealing, in some embodiments sealing to a proximal/top portion or structure of a reservoir/container, or in other cases where sealing may comprise embodiments that seal to the transducer, or a feature on the transducer housings. Further, some embodiments may comprise the dynamic ability to control the volume of fluid within these designs, to minimize the potential for air bubbles or turbulence in said fluid and to allow for changes in the focal length to the target area without moving the transducer. As such, integrated features allowing fluid communication, and control of, may be provided (ability to provide/remove fluid on demand), including the ability to monitor and control various fluid parameters, some disclosed above. In order to provide this functionality, the overall system, and as part, the Coupling sub-system, may comprise a fluid conditioning system, which may contain various electromechanical devices, systems, power, sensing, computing, pumping, filtering and control systems, etc. The reservoir may also be configured to receive signals that cause it to deform or change shape in a specific and controlled manner to allow the target point to be adjusted without moving the transducer.

Coupling support systems may include various mechanical support devices to interface the reservoir/container and medium to the patient, and the workspace (e.g., bed, floor, etc.). In some embodiments, the support system comprises a mechanical arm with 3 or more degrees of freedom. Said arm may have a proximal interface with one or more locations (and features) of the bed, including but not limited to, the frame, rails, customized rails or inserts, as well as one or more distal locations of the reservoir or container. The arm may also be a feature implemented on one or more Carts, wherein Carts may be configured in various unlimited permutations, in some cases where a Cart only comprises the role of supporting and providing the disclosed support structure.

In some embodiments, the support structure and arm may be a robotically-enabled arm, implemented as a stand-alone Cart, or integrated into a Cart further comprising two or more system sub-systems, or where in the robotically-enabled arm is an arm of another robot, of interventional, surgical or other type, and may further comprise various user input features to actuate/control the robotic arm (e.g., positioning into/within coupling medium) and/or Coupling solution features (e.g., filling, draining, etc.). In some examples, the support structure robotic arm positional encoders may be used to coordinate the manipulation of the second arm (e.g. comprising the therapy transducer/treatment head), such as to position the therapy transducer to a desired/known location and pose within the coupling support structure.

Overall, significant unmet needs exist in interventional and surgical medical procedures today, including those procedures utilizing minimally invasive devices and approaches to treat disease and/or injury, and across various types of procedures where the unmet needs may be solved with entirely new medical procedures. Today's medical system capabilities are often limited by access, wherein a less or non-invasive approach would be preferred, or wherein today's tools aren't capable to deliver preferred/required tissue effects (e.g., operate around/through critical structures without serious injury), or where the physical set up of the systems makes certain procedure approaches less desirable or not possible, and where a combination of approaches, along with enhanced tissue effecting treatments, may enable entirely new procedures and approaches, not possible today.

In addition, specific needs exist for enabling histotripsy delivery, including robotic histotripsy delivery, wherein one or more histotripsy therapy transducers may be configured to acoustically couple to a patient, using a completely sealed approach (e.g., no acoustic medium communication with the patient's skin) and allowing the one or more histotripsy transducers to be moved within the coupling solution without impeding the motion/movement of the robotic arm or interfering/disturbing the coupling interface, which could affect the intended treatment and/or target location.

Disclosed herein are histotripsy acoustic and patient coupling systems and methods, to enable histotripsy therapy/treatment, as envisioned in any setting, from interventional suite, operating room, hybrid suites, imaging centers, medical centers, office settings, mobile treatment centers, and/or others, as non-limiting examples. The following disclosure further describes novel systems used to create, control, maintain, modify/enhance, monitor and setup/takedown acoustic and patient coupling systems, in a variety of approaches, methods, environments, architectures and work-flows. In general, the disclosed novel systems may allow for a coupling medium, in some examples degassed water, to be interfaced between a histotripsy therapy transducer and a patient, wherein the acoustic medium provides sufficient acoustic coupling to said patient, allowing the delivery of histotripsy pulses through a user desired treatment location (and volume), where the delivery may require physically moving the histotripsy therapy transducer within a defined work-space comprising the coupling medium, and also where the coupling system is configured to allow said movement of the therapy transducer (and positioning system, e.g., robot) freely and unencumbered from by the coupling support system (e.g., a frame or manifold holding the coupling medium).

Coupling System and Sub-Systems/Components

Figure 2:
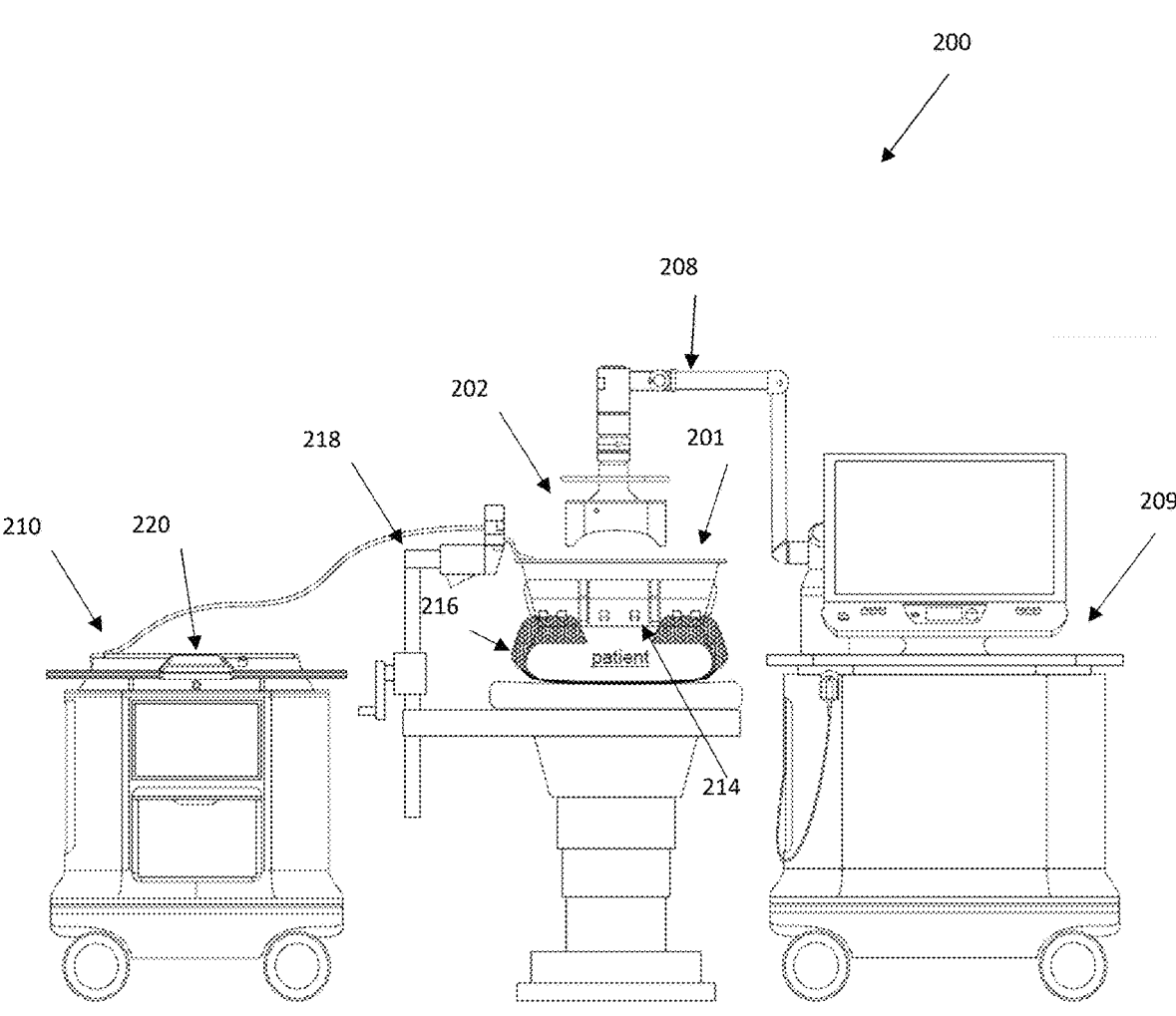
FIG. 2 is one embodiment of a histotripsy therapy and imaging system with a coupling system.

The disclosed histotripsy acoustic and patient coupling systems, in general, may comprise one or more of the following sub-systems and components, an example of which is depicted in FIG. 2, including but not limited to 1) a membrane/barrier film to provide an enclosed, sealed and conformal patient coupling and histotripsy system interface, 2) a frame and assembly to retain the membrane and provide sufficient work and head space for a histotripsy therapy transducers required range of motion (x, y and z, pitch, roll and yaw), 3) a sufficient volume of ultrasound medium to afford acoustic coupling and interfaces to a histotripsy therapy transducer and robotic arm, 4) one or more mechanical support arms to allow placement, positioning and load support of the frame, assembly and medium and 5) a fluidics system to prepare, provide and remove ultrasound medium(s) from the frame and assembly.

In some embodiments, the coupling system may be fully sealed, and in other embodiments and configurations, it may be partially open to afford immediate access (physical and/or visual).

The acoustic and patient coupling systems and sub-systems may further comprise various features and functionality, and associated work-flows, and may also be configured in a variety of ways to enable histotripsy procedures as detailed below.

FIG. 2 illustrates one embodiment of a histotripsy therapy and imaging system 200, including a coupling assembly 201. As described above, a histotripsy therapy and imaging system can include a therapy transducer 202, an imaging system, a robotic positioning arm 208, and a fluidics cart 210. The robotic positioning arm may be attached to a therapy cart, such as cart 209.

The therapy and/or imaging transducers can be disposed within in the coupling assembly 201 which can further include a coupling membrane 214 and a membrane constraint 216 configured to prevent the membrane from expanding too far from the transducer. The coupling membrane can be filled with an acoustic coupling medium such as a fluid or a gel. The membrane constraint can be, for example, a semi-rigid or rigid material as compared to the membrane, and configured to restrict expansion/movement of the membrane. In some embodiments, the membrane constraint is not used, and the elasticity and tensile strength of the membrane prevent over expansion. The coupling membrane can be a mineral-oil infused SEBS membrane to prevent direct fluid contact with the patient's skin. In the illustrated embodiment, the coupling assembly 201 is supported by a mechanical support arm 218 which can be load bearing in the x-y plane but allow for manual or automated z-axis adjustment. The mechanical support arm can be attached to the floor, the patient table, or the fluidics cart 210. The mechanical support is designed and configured to conform and hold the coupling membrane 214 in place against the patient's skin while still allowing movement of the therapy/imaging transducer relative to the patient and also relative to the coupling membrane 214 with the robotic positioning arm 208.

The fluidics cart 210 can include additional features, including a fluid tank 220, a cooling and degassing system, and a programmable control system. The fluidics cart is configured for external loading of the coupling membrane with automated control of fluidic sequences. Further details on the fluidics cart are provided below.

Membranes/Barrier Films and Related Architectures

Membranes and barrier films may be composed of various biocompatible materials which allow conformal coupling to patient anatomy with minimal or no entrapped bubbles capable of interfering with ultrasound imaging and histotripsy therapy, and that are capable of providing a sealed barrier layer between said patient anatomy and the ultrasound medium, of which is contained within the work-space provided by the frame and assembly.

Membrane and barrier film materials may comprise flexible and elastomeric biocompatible materials/polymers, such as various thermoplastic and thermoset materials, as well as permanent or bioresorbable polymers. Additionally, the frame of the UMC can also comprise the same materials. In some examples, the membrane may be rigid or semi-rigid polymers which are pre-shaped or flat.

Ultrasound Medium

As previously described, the ultrasound medium may comprise any applicable medium capable of providing sufficient and useful acoustic coupling to allow histotripsy treatments and enable sufficient clinical imaging (e.g., ultrasound). Ultrasound mediums, as a part of this disclosure and system, may comprise, but are not limited to, various aqueous solutions/mediums, including mixtures with other co-soluble fluids, of which may have preferred or more preferred acoustic qualities, including ability to match speed of sound, etc. Example mediums may comprise degassed water and/or mixtures/co-solutions of degassed water and various alcohols, such as ethanol.

Mechanical Support Arms and Arm Architectures

In order to support the acoustic and patient coupling system, including providing efficient and ergonomic workflows for users, various designs and configurations of mechanical support arms (and arm architectures) may be employed. Support arms may be configured with a range of degrees of freedom, including but not limited to allowing, x, y, z, pitch, roll and yaw, as well additional interfacing features that may allow additional height adjustment or translation.

Arms may comprise a varied number and type of joints and segments. Typically, arms may comprise a minimum of 2 segments. In some configurations, arms may comprise 3 to 5 segments.

Arms are also be configured to interface proximally to a main support base or base interface (e.g., robot, table, table/bed rail, cart, floor mount, etc.) and distally to the frame/assembly and overall "UMC" or "coupling solution". This specific distal interface may further include features for controlling position/orientation of the frame/assembly, at the frame/assembly interface.

For example, in some embodiments, the arm/frame interface may comprise a ball joint wrist. In another example, the interface may include use of a gimbal wrist or an adjustable pitch and roll controlled wrist. These interfaces may be further employed with specific user interfaces and inputs, to assist with interacting with the various wrists, of which may include additional handles or knobs (as an unlimited example), to further enable positioning the UMC/coupling solution. For example, a gimbal wrist may benefit from allowing the frame/assembly to have 3 degrees of freedom (independent of the arm degrees of freedom), including pitch, roll and yaw adjustments.

Support arms, configured with arm wrists, further interfaced with frames/assemblies, may comprise features such as brakes, including cable or electronic actuated brakes, and quick releases, which may interact with one or more axis, individually, or in groupings. They may also include electronic lift systems and base supports. In some embodiments, these lift systems/base supports are co-located with robot arm bases, wherein said robot arm is equipped with the histotripsy therapy transducer configured to fit/work within the enclosed coupling solution. In other embodiments, the support arm is located on a separate cart. In some cases, the separate cart may comprise a fluidics system or user console. In other embodiments, it is interfaced to a bed/table, including but not limited to a rail, side surface, and/or bed/table base. In other examples/embodiments, it's interfaced to a floor-based structure/footing, capable of managing weight and tipping requirements.

Fluidics Systems, Control Systems and System Architectures

As a part of overall fluidics management, histotripsy systems including acoustic/patient coupling systems, may be configured to include an automated fluidics system, which primarily is responsible for providing a reservoir for preparation and use of coupling medium, where preparation may include the ability to degas, temperature adjust, monitor, adjust, dispense/fill, and retrieve/drain coupling medium to/from the frame/assembly. The fluidics system may include an emergency high flow rate system for rapid draining of the coupling medium from the UMC. In some embodiments, the fluidics system can be configured for a single use of the coupling medium, or alternatively, for re-use of the medium. In some embodiments, the fluidics system can implement positive air pressure or vacuum to carry out leak tests of the UMC and membrane prior to filling with a coupling medium. Vacuum assist can also be used for removal of air from the UMC during the filling process. The fluidics system can further include filters configured to prevent particulate contamination from reaching the UMC.

The fluidics system may implemented in the form of a mobile fluidics cart. The cart may comprise an input tank, drain tank, degassing module, fill pump, drain pump, inert gas tank, air compressor, tubing/connectors/lines, electronic and manual controls systems and input devices, power supplies and one or more batteries. The cart in some cases may also comprise a system check vessel/reservoir for evaluating histotripsy system performance and related system diagnostics (configured to accommodate a required water volume and work-space for a therapy transducer).

Treatment Planning, Tissue Volume Packing, and Navigation/Pathway Patterns Through Tissue Volume The systems and methods described herein may further employ software, algorithms, or other automated processes for treatment planning which can include identifying or determining a target tissue volume within a subject, packing or filling the target tissue volume with a plurality of discrete treatment locations, and establishing a treatment pathway for systematically navigating the treatment head/therapeutic transducer array of the histotripsy system through the target tissue volume to complete a given therapeutic procedure of the target tissue volume.

Tissue Volume Packing

Prior to a histotripsy procedure, the system and/or user must first identify the size and/or shape of a target tissue volume/target lesion to be treated. The size and shape of the target tissue volume may depend based on the type of procedure being performed, the specific location of the lesion or target tissue, type of tissue/lesion, and other factors including the depth of the target tissue, the acoustic window to the target tissue, the nature of surrounding tissues, treatment constraints including a maximum treatment time and/or maximum energy dose to be delivered, and/or patient specific parameters including age, gender, prior treatment history, body composition, etc. Systems and methods, including hardware and software are provided herein for providing treatment planning and preparing a digital treatment plan for a histotripsy procedure, that can include identifying a tissue location to be treated, generating a target tissue volume corresponding to the tissue location, and placing a plurality of treatment locations within the target tissue volume. The digital treatment plan can be implemented or executed by a histotripsy therapy system to apply the digital treatment plan to the tissue location of the patient.

For example, if the tissue location to be treated includes a tumor in the subject (e.g., liver tumor, brain tumor, or other soft tissue tumor) then the system and/or the user can determine the target tissue volume size based on the size of the tumor plus any desired margins to ensure complete treatment. The margin size can be pre-configured in the system or determined by the user, and may vary depending on the tumor type and/or tumor location, surgeon preference, other patient risk factors, etc.

The target tissue volume shape may also be customized or modified depending on the tissue location to be treated. While the examples provided herein generally describe spherical or ellipsoidal target tissue volumes, it should be understood that other target tissue volume shapes are considered. The overall dimensions of the target tissue volume can be changed to ensure that the tissue location to be treated (e.g., a tumor) is fully treated according to a desired or pre-set treatment plan while limiting the amount of energy delivered to or through non-diseased or healthy surrounding tissues. In some aspects, a target tissue volume can be as small as a single bubble cloud (e.g., only a single discrete treatment location), and in other embodiments, the target tissue volume can be filled during treatment planning with a plurality of discrete treatment locations, with the volume of tissue treated at each discrete treatment location determined by the size of the bubble cloud. In some aspects, the size and shape of target tissue volume can be chosen based on pre-treatment diagnostics including medical imaging such as CT, MRI, or ultrasound.

Bubble cloud size is determined by many factors, including the overall pulse sequence used to generate and maintain cavitation bubble clouds (e.g., intrinsic threshold sequences, shock scattering sequences, etc.), frequency, pulse repetition frequency (PRF), driving voltage, tissue type, depth, intervening tissue type, etc. For a given pulse sequence and driving parameters, a bubble cloud generated by the histotripsy systems described herein will generally be the same size or within an acceptable threshold. However, it should be understood that the nature of cavitation or bubble clouds generated by histotripsy are dynamic and therefore bubble cloud locations and size can vary and can further be affected by other factors such as residual cavitation nuclei in a target tissue volume, particularly after therapy has started. For purposes of this disclosure, the term "target tissue volume" refers to the entire physical volume that is intended to be treated. Often, this target tissue volume is contoured to a specific target tissue (e.g., a tumor within the liver). The term "focal locations" or "treatment locations" can refer to points within the target tissue volume that the bubble cloud is to be generated at to treat a discrete portion of the overall treatment volume. "Bubble cloud size" can refer to the physical dimensions of a single bubble cloud with respect to each of the primary transducer dimensions (lateral "X" and "Y", and axially "Z"). Bubble cloud "spacing parameters" refer to the spacing parameters and logic used to pack a treatment volume up to the boundary of the target tissue volume. These parameters are also considered when determining the point spacing to achieve the desired overlap and/or margins. Similarly, "point spacing configuration parameters" (X,Y, and Z, xy, yz, and xz) refer to the desired (maximum) physical separation of adjacent bubble clouds in the primary transducer dimensions such that the desired treatment overlap is achieved. The desired overlap can be, for example, 100% overlap all the way to significant physical separation (e.g., no overlap) depending on what is desired for a specific treatment.

Figure 4A:
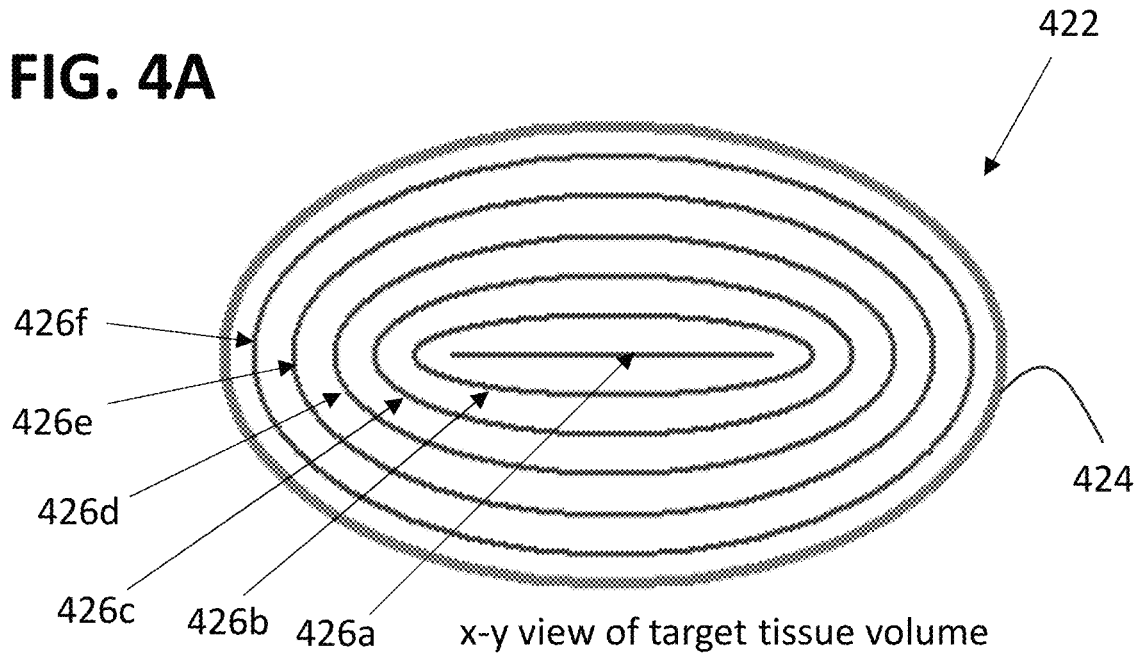
FIGS. 4A-4D illustrate one embodiment of a digital treatment plan that includes packing a target tissue volume with a plurality of treatment volumes.

FIG. 4A is a cross-sectional (x-y axis) view of an ellipsoidal target tissue volume 422 having diameters in each axis of Dx, Dy, and Dz. During a treatment planning aspect of a histotripsy procedure, the system can use the dimensions of the target tissue volume in combination with bubble cloud size parameters and desired spacing parameters (X point spacing configuration parameter, Y point spacing configuration parameter, Z point spacing configuration parameter) between discrete treatment locations to pack the target tissue volume with a plurality of discrete treatment locations to ensure complete treatment of the target tissue volume according to the treatment plan. As described above, the percentage of the target tissue volume treated can vary depending on the specific tissue type and disease state to be treated. In some examples, forming cavitation within 90-100% of the target tissue volume may be considered complete treatment, while in other embodiments as little as 10-20% treatment of the target tissue volume is desired. The bubble cloud size for a known transducer/sequence combination can include diameters in each axis of Bx, By, and Bz, and point spacing between treatment locations can be defined by spacing distances apart on each axis of Sx, Sy, and Sz. In some examples, the spacing parameters are defined as the distances between center-points of adjacent focal locations. The desired treatment size as configured by the user can further include a margin M that further increases the overall size of the target tissue volume to ensure complete ablation/liquefication/lysing of the diseased tissue in the target tissue volume.

In one aspect, the spacing parameters in the x-y axis, Sx and Sy, are the same, and the spacing parameter in the z axis, Sz, is different than Sx and Sy. This can account for ellipsoidal shaped bubble clouds that are longer in the z direction than they are wide in the x-y direction. However, it should be understood that if different sized or shaped bubble clouds are used, then the spacing parameters can be adjusted or changed. For example, with spherically or uniformly shaped bubble clouds, all the spacing parameters may be similar or the same.

In FIG. 4A, the target tissue volume 422 includes a margin contour 424 that, in the x-y view, is defined by diameters of Dx+M and Dy+M. In one embodiment, FIG. 4A represents a central slice in the x-y view of the target tissue volume (e.g., the largest diameter Dx and Dy in the target tissue volume). As described above, this figure shows an x-y slice of a three-dimensional target tissue volume. In one implementation, a treatment planning algorithm first packs margin contour 424 with concentric contours 426a-426f, spaced evenly between a central contour 426a of the volume and an outer contour 426f with major/minor axes of Dx/2+M-Bx and Dy/2+M-By. As shown in FIG. 4A, depending on the intended bubble cloud size and the overall target tissue volume size and shape, in some implementations the treatment planning algorithm the central contour 426a may be a row or linear contour instead of an ellipsoidal contour. In some embodiments, the number of ellipses may be set such that the radial spacing between them in the x-y dimensions is not greater than the x-y point spacing configuration parameters.

It should be understood that in FIG. 4A, since the overall target tissue volume is ellipsoidal, then the most efficient way to pack the volume is with concentric ellipses. However, other shaped target tissue volumes can be packed with shapes that better conform to the outer contour of the target tissue volume (e.g., circular pathways for spherical target tissue volumes, etc.). For example, linear segments between parallel edges could be packed into the target tissue volume. Alternatively, the target tissue volume could be packed with arbitrary shapes of using "shrunk" copies of the perimeter shape with progressive "smoothing" of turns to soften the resulting sharp corners that would result.

Figure 4B:
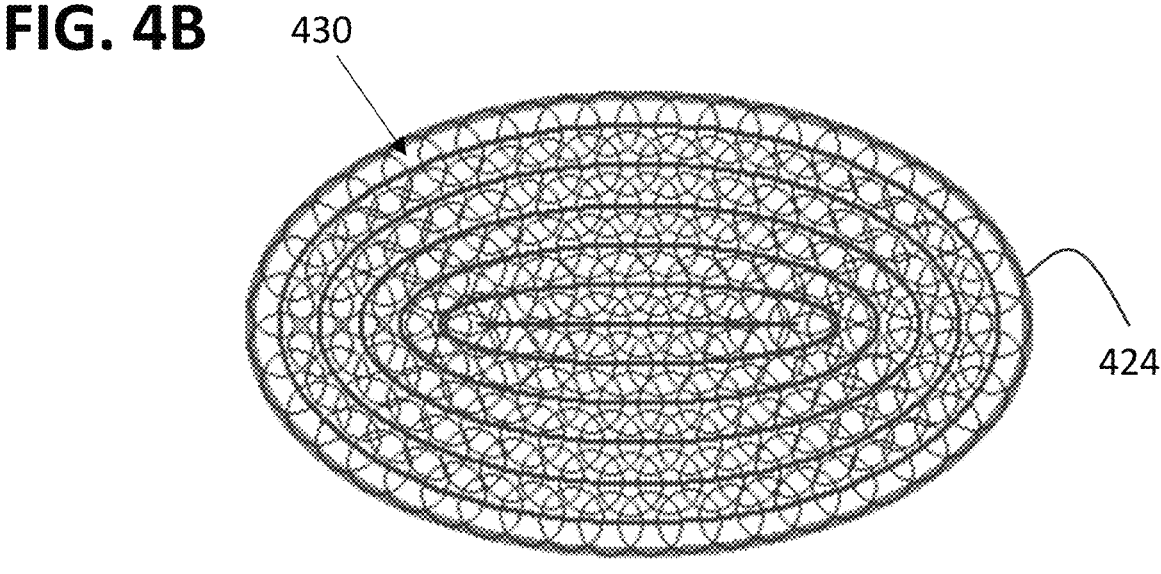
Figure 4C:
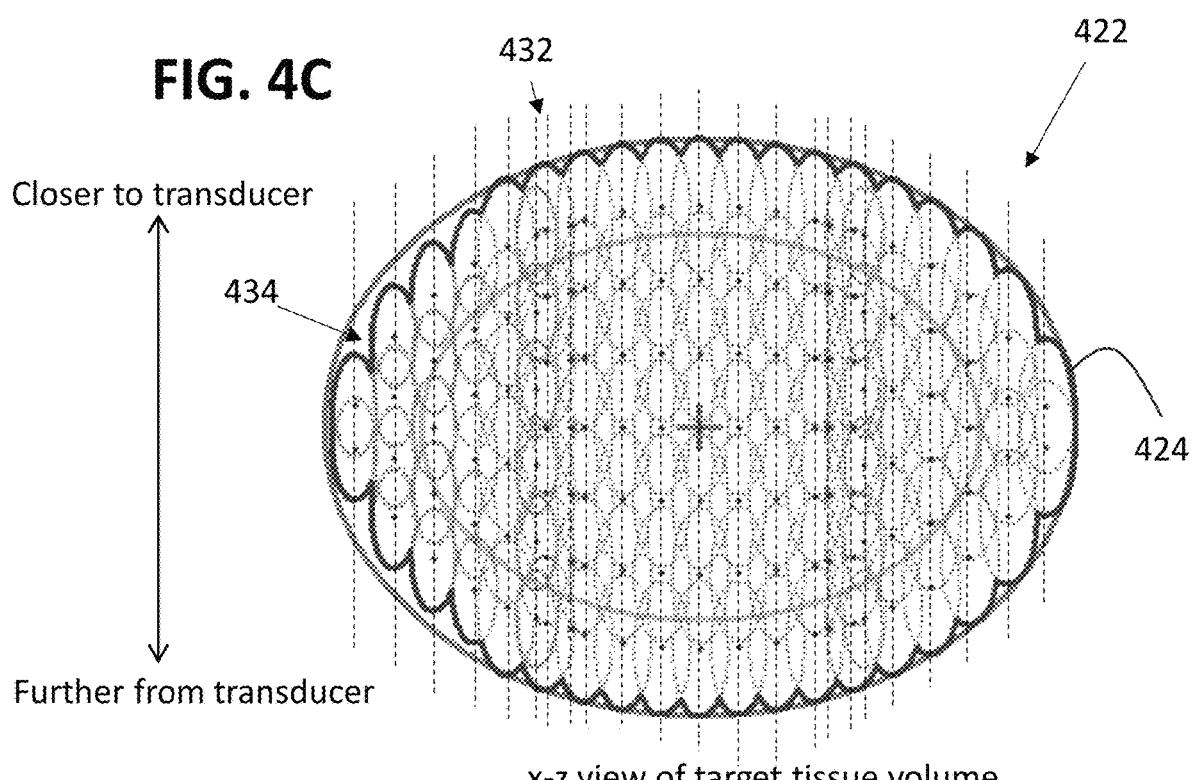

In one implementation of the treatment planning algorithm, referring to FIG. 4B, discrete treatment locations 430 are equally spaced with centers along these x-y contours (426a-426f in FIG. 4A) such that the spacing adjacent treatment locations does not exceed the average of the x-y point spacing configuration parameters. As shown, the outer contour 426f is the outermost pathway packed with discrete treatment locations, and the spacing between the outer contour 426f and the margin contour 424 is chosen such that the bubble cloud size for a given treatment location along the outer contour 426f does not extend beyond or outside of the margin contour. Due to complexities with spacing along the circumference of an ellipse, in some aspects the requirement that treatment location spacing does not exceed the average of the x-y point spacing configuration parameters may not be strictly enforced. Alternatively, a requirement on average speed of the treatment head/therapy transducer through each pathway/ellipse can be made to ensure that the appropriate dose of energy or number of histotripsy pulses is delivered to each of the treatment points along a given pathway. The average or pre-planned speed of the treatment head/therapy transducer can be applied to the digital treatment plan such that there is a desired or pre-planned speed associated with each contour and treatment location in the digital treatment plan.

Referring to FIGS. 4C-5D, after the discrete locations have been placed along each contour in the x-y plane, the treatment planning algorithm can extend a line 432 in the Z direction through each discrete treatment location from each x-y contour, and additional treatment locations can be added to the treatment plan in the target tissue volume in the Z-direction along each line 432 such that the outermost treatment locations of the target tissue volume (accounting for the bubble cloud size) do not extend outside the margin contour 424. Additional treatment locations can be spaced along each line such that the spacing between them does not exceed the Z point spacing configuration parameter.

It is important to note that in FIGS. 4A-4D, the target tissue volume is packed to account for an ellipsoidal bubble cloud shape to be produced at each discrete treatment location. In this embodiment, the bubble clouds produced at each treatment location are intended to have an elongated ellipsoidal shape that extends further in the Z dimension (i.e., away from the therapy transducer) than in the X and Y dimensions. However, it should be noted that advancements in transducer array construction, pulse generators, and optimization of pulse sequences can facilitate bubble clouds with more uniform (i.e., spherical) shapes. Therefore, while the illustrated embodiment describes the use of ellipsoidal bubble clouds, similar packing techniques can be implemented with more uniform spherical shapes. It should be understood that when the bubble clouds are more uniform in shape, the treatment planning algorithm may place more discrete treatment locations on each line 432 extending in the Z direction to compensate for reduced Z dimensions of uniform/spherical bubble clouds compared to ellipsoidal shaped bubble clouds.

Figure 4D:
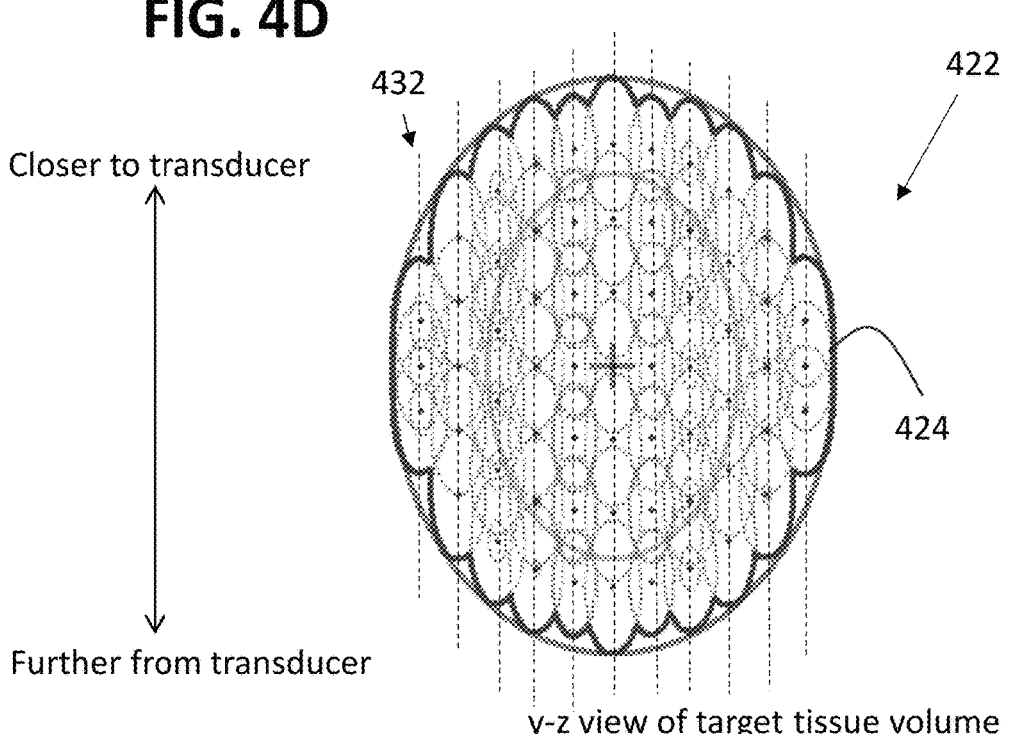

Referring to FIG. 4D, it should be understood that with a spherical/ellipsoidal target tissue volume that is filled with a plurality of spherical/ellipsoidal bubble clouds corresponding to each discrete treatment location, that there may be gaps 434 near the margin contour 424 of the target tissue volume that may not receive any therapeutic energy/bubble clouds. This is simply a function of the shape and size of the target tissue volume and the intended bubble cloud size/shape. Generally the desired margins are intended to ensure that the entirety of the diseased tissue is treated with a given treatment plan even with these gaps in coverage.

In the embodiments illustrated herein, the treatment planning algorithm is configured to pack the target tissue volume with a plurality of treatment locations based on a uniform bubble cloud size throughout the volume. However, other embodiments of the treatment planning algorithm can employ packing techniques that include two or more bubble cloud sizes and or shapes. For example, the target tissue volume can be divided into a plurality of sub-volumes with a different bubble cloud size/shape intended for each sub-volume. In some examples, the target tissue volume can be divided into a first sub-volume that comprises an outer shell or perimeter of the target tissue volume, with a second sub-volume that comprises an inner volume that is located entirely within the first sub-volume. In this configuration, it could then be desirable to pack the first/outer sub-volume with smaller bubble clouds to better conform to the outer margin and reduce or eliminate gaps, while the second/inner sub-volume could be packed with larger bubble clouds for more efficient treatment or fewer treatment locations. Other implementations are contemplated, including packing a sub-volume of the target tissue volume that is closer to the transducer array with a bubble cloud size/shape that is different than the sub-volume that is further or more distal from the transducer array. In other embodiments, pulse sequences with different tissue selectivity could be factored into a treatment plan to be used for different parts of a treatment volume. For example, sequences better suited to treat tumor vs. mostly healthy margin could be implemented into the treatment plan for a target tissue volume.

Navigation or Traversal Through the Treatment Pattern/Pathways

Figure 5A:
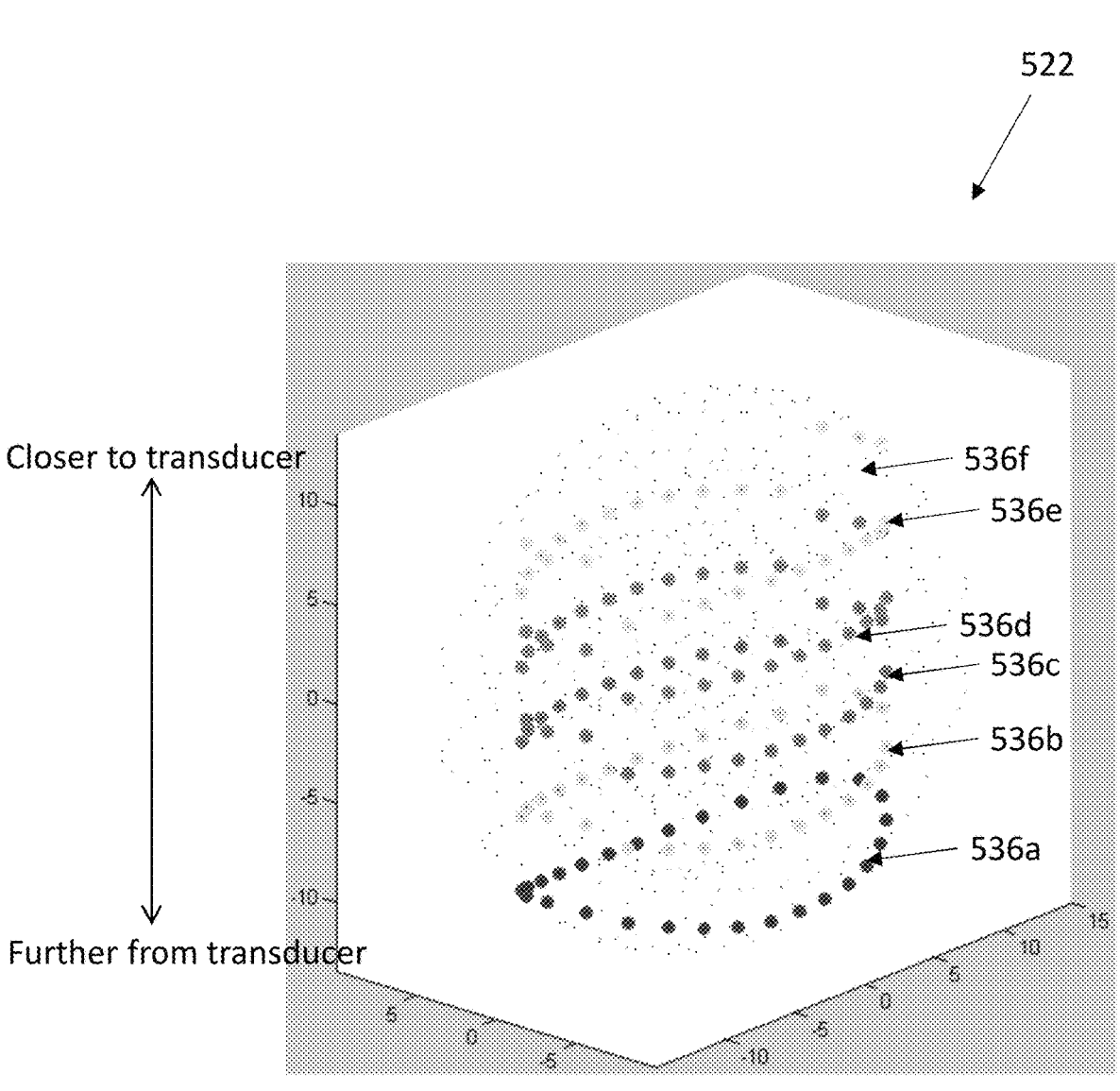
FIG. 5A-5C are examples of traversing a plurality of treatment volumes in a target tissue volume according to a digital treatment plan.

Referring now to FIG. 5A, with the target tissue volume 522 packed with a plurality of discrete treatment locations along the plurality of x-y contours and Z dimension lines, the treatment planning algorithm can then divide the discrete treatment locations into groups of treatment locations, where each group comprises a contiguous sequence of points that are desired to be treated consecutively without treatment stopping between (e.g. a single treatment point, a column of treatment points, a ring of treatment points, etc.). In some embodiments, the groupings are formed from a single Z position or line from each x-y location along a single x-y contour of the treatment plan. For a given x-y contour (e.g., a single contour from FIG. 4A such as 426f), the six groups may be formed, including 536a, 536b, 536c, 536d, 536e, and 536f, from all of the discrete treatment locations/points extending along Z lines originating from the x-y points of a single x-y contour. Notice that for this ellipsoidal treatment volume, the number of treatment locations in the Z direction at each of these x-y points can be different, and therefore the treatment planning algorithm does not always provide continuous, smooth rings like would be seen in a spherical treatment volume.

Figure 5B:
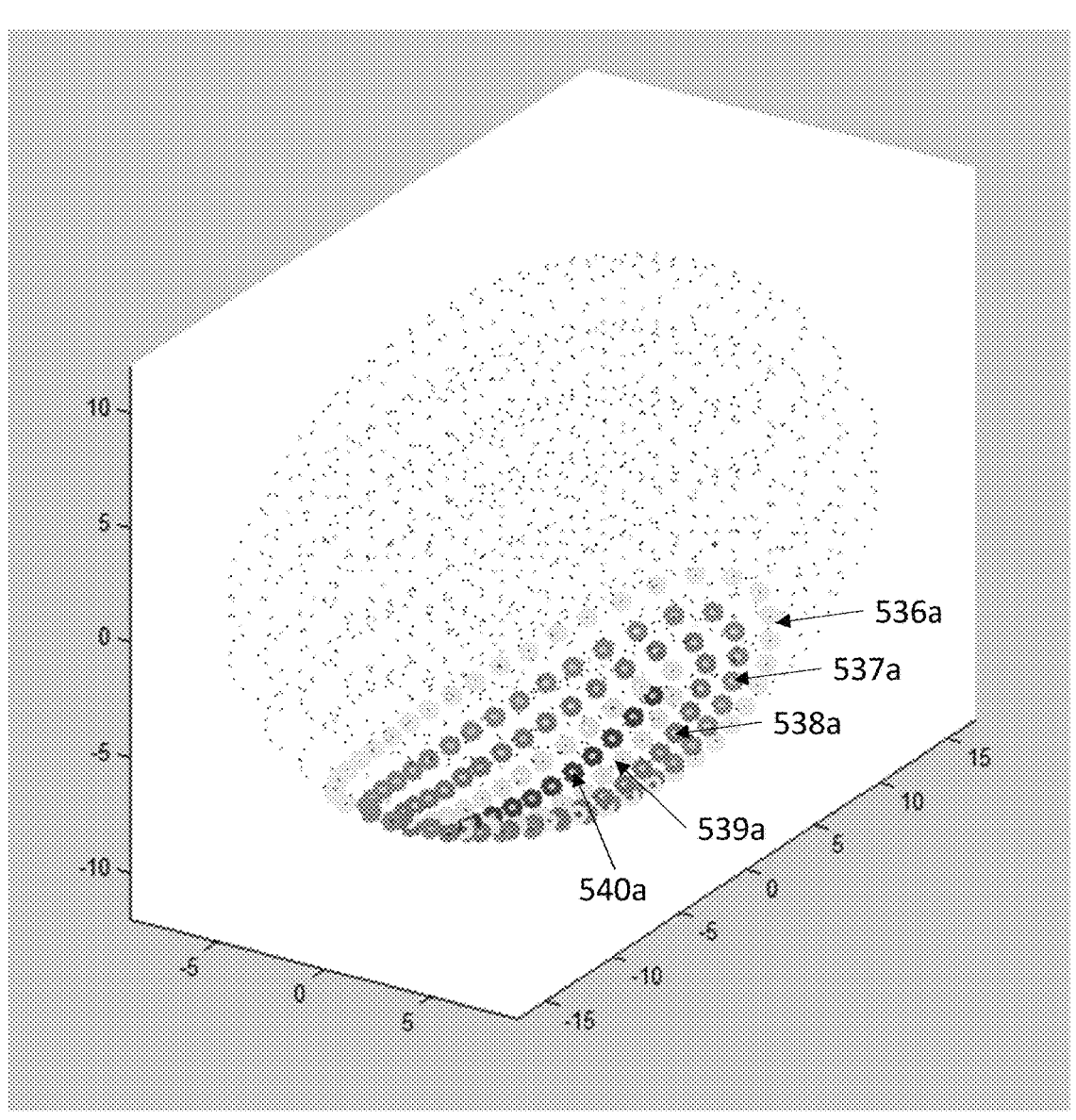
Figure 5C:
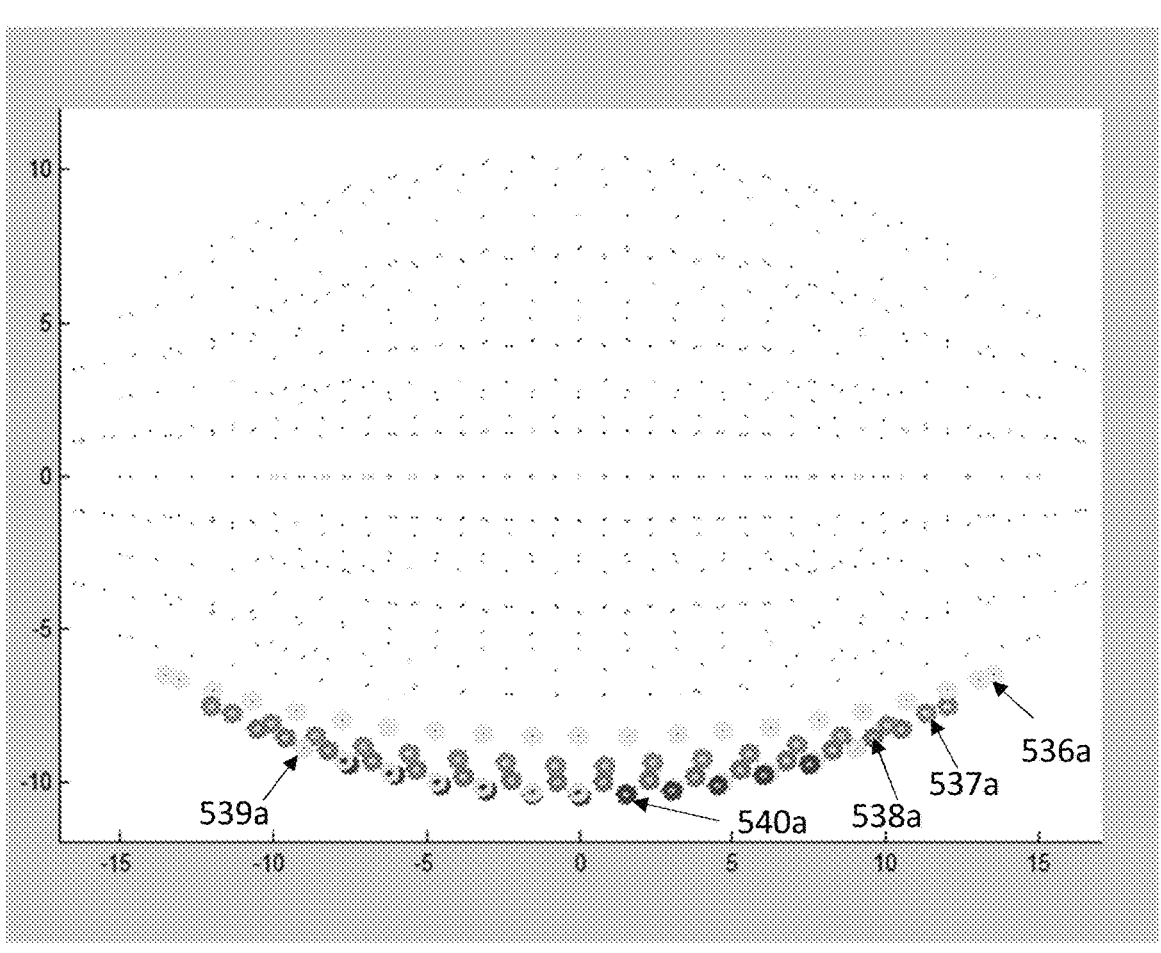

In FIG. 5A, various groupings along the Z-axis are shown for a single x-y contour. FIGS. 5B-5C, on the other hand, show groupings of treatment locations for a plurality of x-y contours near the distal (e.g., bottom) of the treatment volume. In one implementation, the treatment planning algorithm can organize the groups from lowest (distal-most) to highest (proximal-most) Z position relative to the therapy transducer array. Navigation or traversal through the collection of groups and treatment locations can then be determined by the treatment planning algorithm. In one implementation, navigation through the groups of treatment locations can start with the distal-most group (e.g., group 540*a*) and proceed proximally (towards the transducer array) to subsequent groups when the treatment locations in a given group are all treated. Traversal within a group can proceed directionally around the contour (e.g., counter-clockwise or clockwise when viewed along the x-y plane. In one implementation, the treatment planning algorithm uses the last treatment location in a given group to determine the first treatment location to be treated in the subsequent group (e.g., the next closest group above or proximal to/towards the transducer array). For example, referring to FIGS. 5B-5C, group 540*a* can be treated first by navigating the transducer array through the group of treatment locations. The treatment planning algorithm can then direct the next treatment location to be treated as the closest treatment location in group 539*a*, and treatment can resume until all the treatment locations in that group are treated. The treatment pathway can continue through groups 538*a*, 537*a*, 536*a*, and so forth. In general the guiding principles can be to treat through the treatment locations of a given group before traversing to the next closest grouping proximally in the Z-direction. It is noted that in this specific implementation, group 540*a* is the distal-most group in the treatment volume, while also being centrally located within the volume. Group 539*a* is the next most-distal grouping, while being positioned laterally in the x-y plane from group 540*a*. The result of this treatment pathway is a traversal that starts with the distal-most grouping and navigated both outwardly (in the x-y plane) and proximally (in the z-plane) through the remaining groupings of treatment locations. While other implementations for navigating between treatment groups are considered, the methodology described above provides the minimum z-travel distance between groups which can increase efficiency and reduce treatment times by limiting travel of the transducer without treating the remaining treatment locations.

Traversal Speed and Acceleration

In addition to the treatment planning/packing and traversal/navigation of a treatment volume described above, another aspect that the treatment planning algorithm may consider when preparing a treatment plan is the velocity the transducer array is moved through the target treatment volume by the robotic system, acceleration/deceleration values, and when and where therapy is turned on or off as the transducer array is navigating through the volume. All of these parameters can be optimized and pre-determined and/or adjusted during a given treatment to optimize treatment efficiency and outcomes.

In one implementation, the treatment planning algorithm can be adapted to configure or adjust the following parameters for a given target treatment volume: 1) Target treatment location (the desired location to move the transducer array focus to), 2) Acceleration/deceleration values, 3) Maximum Velocity, 4) Therapy on/off before move (flag to set therapy on/off before move), 5) Therapy on/off after move (flag to set therapy on/off after move), 6) $T_{on}$ (idle time after move while stationary with therapy on), 7) $T_{cool}$ (idle time after move with therapy off, happens after $T_{on}$), and 8) Dwell time at each treatment location (e.g., amount of time to remain at treatment location before moving to next treatment location). These parameters can be chosen to determine where the transducer array is to be moved, how fast the robotic positioning system accelerates/decelerates the transducer array between treatment locations, a maximum velocity that the robotics system can move the transducer array, whether or not therapy is on before, after, or during a move, and whether or not cooling periods (e.g., periods of no therapy) are to be implemented within a given treatment plan. Any combination of these parameters can be adjusted in the treatment plan to deliver a desired dose to each treatment location.

Figure 6:
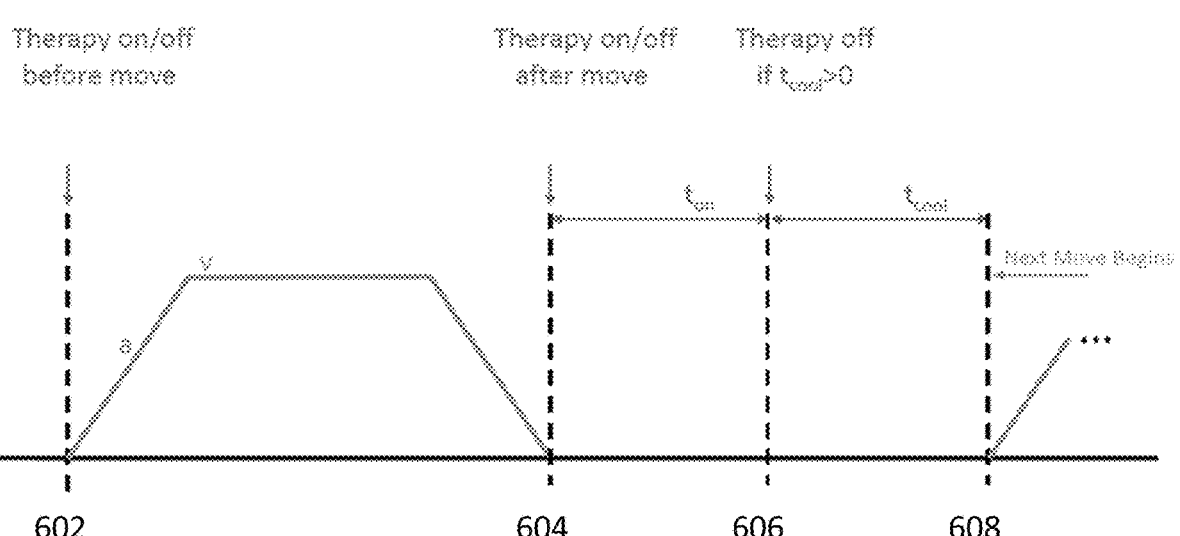
FIG. 6 illustrates one embodiment of a timing diagram that includes therapy on/off controls for traversing a digital treatment plan.

FIG. 6 is a general motion step diagram that shows one example of how these parameters may be used while navigating a treatment plan with a robotically controlled histotripsy system. At step 602, the system is positioned at a first location (perhaps a treatment location that has just been treated with histotripsy, or alternatively, at a staging location outside of the treatment volume and preparing to begin treatment) and is preparing to move to a subsequent treatment location. The system can refer to the treatment plan to determine if therapy is to be on or off before/during this move. In between steps 602 and 604, the robotic system moves the transducer array towards the target treatment location with an acceleration value "a" which maxes out at maximum velocity "v". The system then implements a deceleration value "d" to decelerate the transducer array such that the velocity is 0 when the transducer array focus arrives at the target treatment location. In some examples, this deceleration value can be a distinct value. In other embodiments, the deceleration value can comprise a symmetric deceleration (e.g., if the acceleration value is "a" then the deceleration value is "−a"). At step 604, the system refers to the treatment plan to determine if therapy is to be on or off after this move. In this example, therapy is turned on for a time $T_{on}$, followed at step 606 by a cooling period $T_{cool}$ where the transducer array focus is stationary with the therapy turned off. However, it should be understood that this timing diagram could include therapy/cooling in the on or off position for any of the illustrated segments. The process can then repeat at step 608 for the next or subsequent treatment location. In FIG. 6, the transducer array has a dwell time of $T_{on}+T_{cool}$ between moves.

Figure 7B:
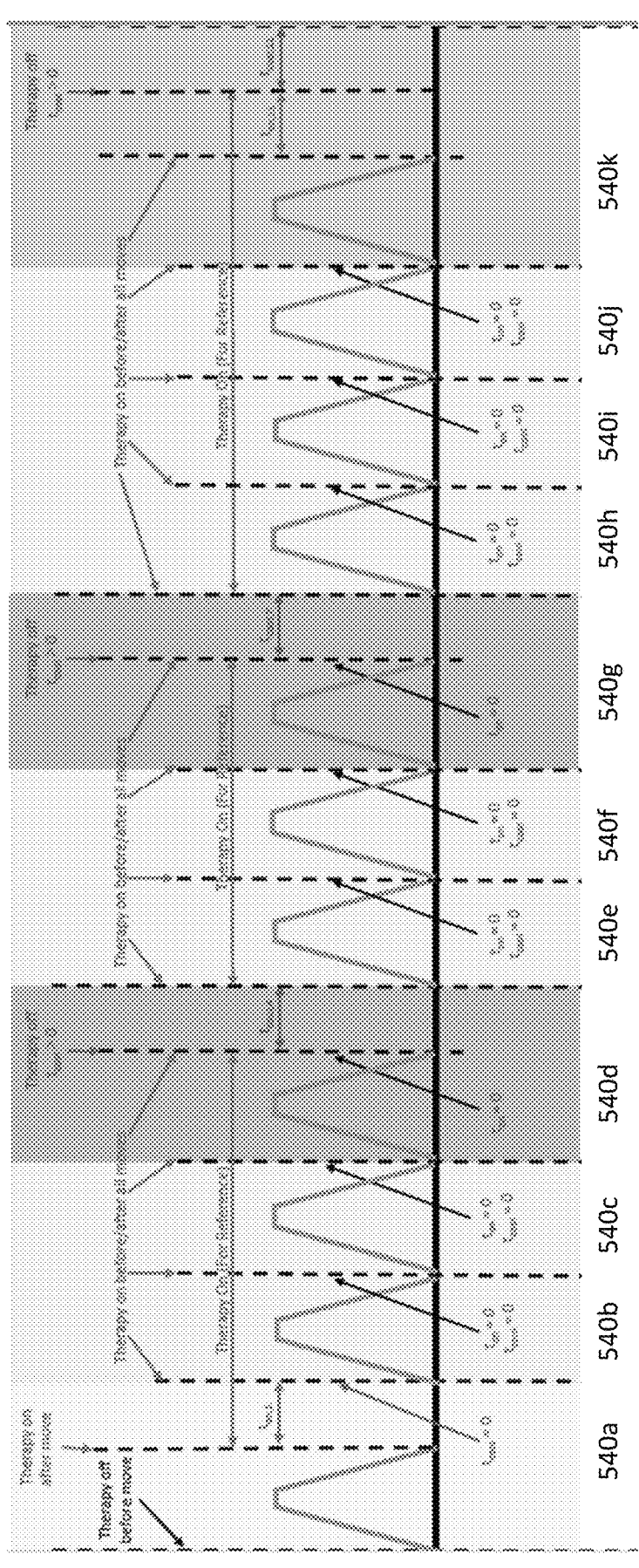

FIGS. 7A-7B is another example of how the parameters described above can be used during a given treatment (or partial treatment as shown). In this example, the system can implement different parameters for different treatment locations or sections of a treatment group. In this example, the partial ring or contour is broken up to end of cooling segments that terminate at treatment locations 540*d* and 540*g*. For purposes of this disclosure, a partial ring or contour can comprise a segment that ends at a point different from where it begins. Treatment location 540*a* represents the starting treatment location for a partial treatment ring or contour and treatment location 540*k* represents the end of the partial ring.

Referring to FIG. 7B, therapy can be turned off and the robotics system/transducer array can be moved to treatment location 540*a*. Next, the robotics system/transducer array can be moved to treatment locations 540*b*, 540*c*, and 540*d* with therapy on before/after/during moves between these treatment locations. Treatment location 540*d* is the end of a cooling segment within this treatment plan, so a cooling period is added at treatment location 540*d* where the robotics system/transducer array is not moving and therapy is turned off. Next, therapy can be turned on again and the robotics system/transducer array can be moved through treatment locations 540*e*, 540*f*, and 540*g* with therapy on before/after/during moves between these treatment locations. Once again, a cooling period is added with therapy turned off at treatment location 540g marking the end of a second treatment segment. The process repeats with treatment on during moves through treatment locations 540h, 540i, 540j, and 540k, with a final cooling period added at the end of the partial ring after treating treatment location 540k.

FIGS. 8A-8B show another example of treating complete contours or pathways within a treatment volume using the parameters and principles described above. In FIG. 8A, two contours 826a and 826b are shown, which can correspond, for example, to contours 540a and 539a of FIG. 5B. In this example, contour 826a has already been treated, and the system is preparing to treat contour 826b, starting with treatment location 842a. In this example, therapy is off for the move through treatment location 842a, and is turned on as the robotics system/transducer array is moved through treatment locations 842b, 842c, 842d, and 842e, with a cooling period added at the end of treatment location 842e. This process is repeated 4 more times, working around the contour, with cooling periods added after treating locations 842j, 842o, 842t, and 842a. With the entire contour treated, the next contour can be treated similar to as described above.

Other iterations of movement speed/velocity and therapy on/off are considered. For example, in some embodiments, movement between treatment locations may be performed with therapy turned off. Once the transducer focus is positioned at a target treatment location, movement can be paused or stopped and therapy can be turned on. Once the desired dose is delivered, the therapy can be turned off again and movement can be controlled to the next treatment location.

In another example, movement between treatment locations can be performed at a constant speed, with therapy turned on to deliver a known/precise dose across all treatment points within a target tissue volume.

The desired dose to be delivered to a target treatment volume for a given treatment plan can be factored into the movement and navigation between treatment locations. For example, To set the movement speed between two points in a ring so as to achieve a desired total dose comprised of:

some fraction of the treatment dose applied while approaching the point some fraction of the treatment dose applied while dwelling at the point some fraction of the treatment dose applied while moving away from the point One could fix the dwell time and then given the spacing between the points, calculate the acceleration and velocity such that the movement time towards and away from the point total up to the balance of required treatment time given the treatment rate (pulse repetition frequency, PRF). The point spacing we use are small enough that the robot doesn't have time to reach a reasonable velocity, so moves within treatment rings are accomplished by acceleration only (robot accelerates from start to halfway and then decelerates from halfway point on to finish point)

$$\text{Movement Time} = (\text{Desired Dose}/PRF) - \text{Dwell } Tim$$

$$\text{Acceleration} = 4 * \text{Spacing/Movement Time}\text{\textasciicircum}2$$

However, in our case where the spacing along the circumference of our treatment rings is variable, this would result in uneven treatment in different rings. If instead we set motion parameters to achieve a nominal average velocity over the treatment ring, the dose will be equivalent in all rings regardless of packing density of points along the circumference. This is how we set our robot motion parameters.

$$\text{Target Speed} = \text{Nominal Spacing} * PRF/\text{Desired Dose}$$

$$\text{Movement Time} = \text{Actual Spacing/Target Speed} - \text{Dwell Time} =$$

$$(\text{Actual Spacing/Nominal Spacing}) * (\text{Desired Does}/PRF) - \text{Dwell Time}$$

$$\text{Acceleration} = 4 * \text{Actual Spacing/Movement Time}\text{\textasciicircum}2$$

It should be understood that any feature described herein with respect to one embodiment can be substituted for or combined with any feature described with respect to another embodiment.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of preparing a treatment plan for a histotripsy procedure in a histotripsy system having one or more processors operatively coupled to a robotic positioning system and an ultrasound transducer array, and a non-transitory computing device readable medium having instructions stored thereon for generating the treatment plan, wherein the instructions are executable by the one or more processors to cause the histotripsy system to perform the method, comprising:

identifying, in one or more medical images of a patient, a tissue location to be treated;

generating, in a treatment planning software of the histotripsy system, a target tissue volume corresponding to the tissue location to be treated, the target tissue volume having an outermost margin contour;

dividing, in the treatment planning software, a lateral slice (xy axis) of the target tissue volume into a first plurality of concentric contours;

placing, in the treatment planning software, a first plurality of treatment locations along each of the first plurality of concentric contours according to predetermined xy spacing parameters;

for each of the first plurality of treatment locations, placing, in the treatment planning software, a second plurality of treatment locations in one or more axial directions (z axis) within the margin contour of the target tissue volume according to predetermined z spacing parameters;

organizing, in the treatment planning software, the second plurality of treatment locations into groups, wherein each group shares a common z position within the target tissue volume;

determining, in the treatment planning software, a navigation pathway that defines a sequential order through which a therapy focus of the histotripsy system is to navigate through the groups during the histotripsy procedure, the navigation pathway starting with a distal-most group, the navigation pathway traversing through each treatment location within the distal-most group, the navigation pathway traversing to a subsequent group that is proximally adjacent to the distal-most group, the navigation pathway traversing through each treatment location within that subsequent group, the navigation pathway repeating for all remaining groups in a distal to proximal direction through the treatment volume.

2. The method of claim 1, wherein the tissue location to be treated comprises a tumor.

3. The method of claim 1, wherein the target tissue volume is ellipsoidal/spherical.

4. The method of claim 1, wherein the xy spacing parameters are based in part on a bubble cloud size/shape of a histotripsy system.

5. The method of claim 1 or 4, wherein the z spacing parameters are based in part on a bubble cloud size/shape of a histotripsy system.

6. The method of claim 5, wherein the z spacing parameter are different than the xy spacing parameters.

7. The method of claim 6, wherein the z spacing parameter is chosen to account for an elongated ellipsoidal bubble cloud shape that extends further in the Z dimension than in the X and Y dimensions.

8. The method of claim 1, wherein the lateral slice comprises a central slice of the target tissue volume.

9. The method of claim 1, wherein the central slice is the largest lateral slice in the target tissue volume.

10. The method of claim 1, wherein the concentric contours are ellipsoidal.

11. The method of claim 1, wherein the first and second plurality of treatment locations provide for 90-100% cavitation of the target tissue volume based on a bubble cloud size/shape of a histotripsy system.

12. The method of claim 1, wherein the generating, providing, and placing steps are performed by a treatment planning system of the histotripsy system.

13. The method of claim 1, further comprising providing a linear contour central to the plurality of concentric contours.

14. The method of claim 1, further comprising associating a predetermined speed of a therapy transducer with each of the first and second plurality of treatment locations in the treatment plan.

* * * * *